(12) United States Patent
Xu

(10) Patent No.: US 9,540,692 B2
(45) Date of Patent: Jan. 10, 2017

(54) MIRNAS AS NOVEL THERAPEUTIC TARGETS AND DIAGNOSTIC BIOMARKERS FOR PARKINSONS DISEASE

(71) Applicant: Rush University Medical Center, Chicago, IL (US)

(72) Inventor: Shunbin Xu, Ferndale, MI (US)

(73) Assignee: Rush University Medical Center, Chicago, IL (US)

( * ) Notice: Subject to any disclaimer, the term of this patent is extended or adjusted under 35 U.S.C. 154(b) by 0 days.

(21) Appl. No.: 14/416,932

(22) PCT Filed: Jul. 24, 2013

(86) PCT No.: PCT/US2013/051849
§ 371 (c)(1),
(2) Date: Jan. 23, 2015

(87) PCT Pub. No.: WO2014/018650
PCT Pub. Date: Jan. 30, 2014

(65) Prior Publication Data
US 2015/0275299 A1    Oct. 1, 2015

Related U.S. Application Data

(60) Provisional application No. 61/675,603, filed on Jul. 25, 2012.

(51) Int. Cl.
| | | |
|---|---|---|
| C12Q 1/68 | (2006.01) | |
| C07H 21/02 | (2006.01) | |
| C07H 21/04 | (2006.01) | |
| C12N 15/113 | (2010.01) | |

(52) U.S. Cl.
CPC .......... C12Q 1/6883 (2013.01); C12N 15/113 (2013.01); *C12N 2310/113* (2013.01); *C12Q 2600/158* (2013.01); *C12Q 2600/16* (2013.01); *C12Q 2600/178* (2013.01)

(58) Field of Classification Search
CPC .......................... C12N 2310/11; C12N 15/113
See application file for complete search history.

(56) References Cited

FOREIGN PATENT DOCUMENTS

| WO | WO 2011/057003 A2 | 5/2011 |
| WO | WO 2011/117353 A1 | 9/2011 |

OTHER PUBLICATIONS

"Human target microRNA has-miR-590-3p SEQ ID No. 557"; Database Geneseq, retrieved from EBI accession No. GSN:AZM70753, Database accession No. AZM70753 sequence; retrieved on Sep. 25, 2013 at http://ibis.internal.epo.org/exam/dbfetch.jsp?id=GSN:AZM70753; XP-002713648; Oct. 27, 2011.

Anonymous; "TaqMan® Array Human MicroRNA Cards"; AB Applied Biosystems; retrieved on Sep. 25, 2013 at http://tools.lifetechnologies.com/content/sfs/brochures/cms_054742.pdf; XP002713649; Jan. 2010.

Maral Mouradian, M.; "MicroRNAs in Parkinson's disease"; Neurobiology of Disease, vol. 46, No. 2; pp. 279-284; XP055080842; Jan. 5, 2012.

Margis, Regina et al.; "Identification of blood microRNAs associated to Parkinson's disease"; Journal of Biotechnology, vol. 152, No. 3; Feb. 3, 2011; XP028156236.

Martins, Madalena et al.; "Convergence of miRNA Expression Profiling, α-Synuclein Interacton and GWAS in Parkinson's Disease"; Plos One, vol. 6, No. 10; pp. 1-11; Oct. 2011; XP055080919.

Miriones-Moyano, E. et al.; "MicroRNA profiling of Parkinson's disease brains identifies early downregulation of miR-34b/c which modulate mitochondrial function"; Human Molecular Genetics, vol. 20, No. 15; pp. 3067-3078; May 10, 2011; XP055080677.

Villa, Chiara et al.; "Role of hnRNP-A1 and miR-590-3p in Neuronal Death: Genetics and Expression Analysis in Patients with Alzheimer Disease and Frontotemporal Lobar Degeneration"; Rejuvenation Research, vol. 14, No. 3; pp. 275-281; Jun. 2011; XP055080714.

International Search Report for International Application No. PCT/US2013/051849 mailed Jan. 7, 2014.

*Primary Examiner* — Amy Bowman
(74) *Attorney, Agent, or Firm* — Brinks Gilson & Lione

(57) ABSTRACT

The disclosure provides pharmaceutical compositions including an oligonucleotide that down-regulates the overexpression of at least one miRNA of SEQ ID NOs: 1-283. The oligonucleotide may be complementary to the nucleotide sequence of at least one of SEQ ID NOs: 1-283, or hybridizes under stringent conditions to a nucleotide sequence of at least one of SEQ ID NOs: 1-283. Further provided are methods of diagnosing Parkinson's Disease (PD) in a subject. The methods may include detecting the level of expression of at least one miRNA of SEQ ID NOs: 1-283 in a biological sample from the subject, and comparing the level of expression in the sample to the level of expression in a reference. Further provided are methods for treating, preventing, or reducing the risk of PD. Kits are also provided.

6 Claims, 11 Drawing Sheets

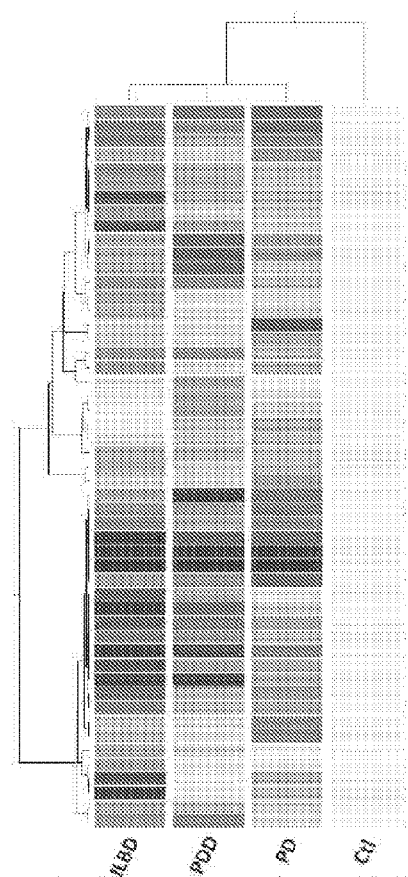
Figure 1. Heat-maps of miRNAs Differentially Expressed in the Putamen *By clinical diagnosis.*

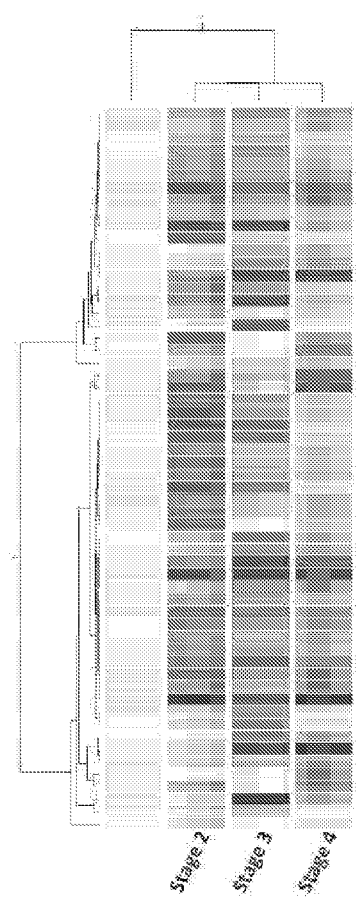
Figure 2. Heat-maps of miRNAs Differentially Expressed in the Putamen *By Unified staging system for LBD*.

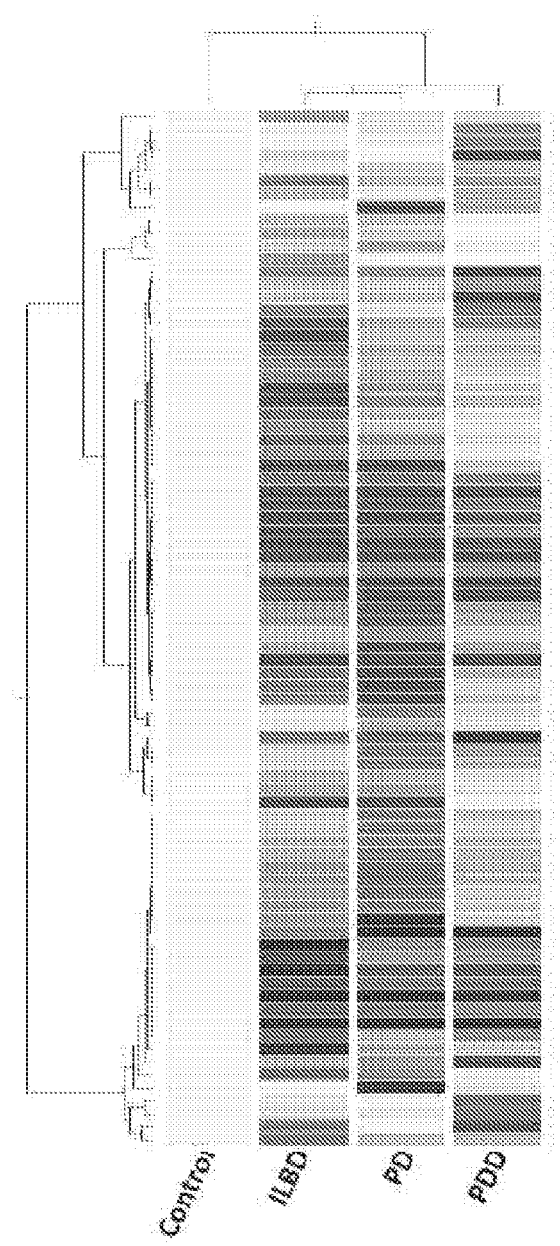
Figure 3. Heat-map of miRNAs Differentially Expressed in CSF *By clinical diagnosis.*

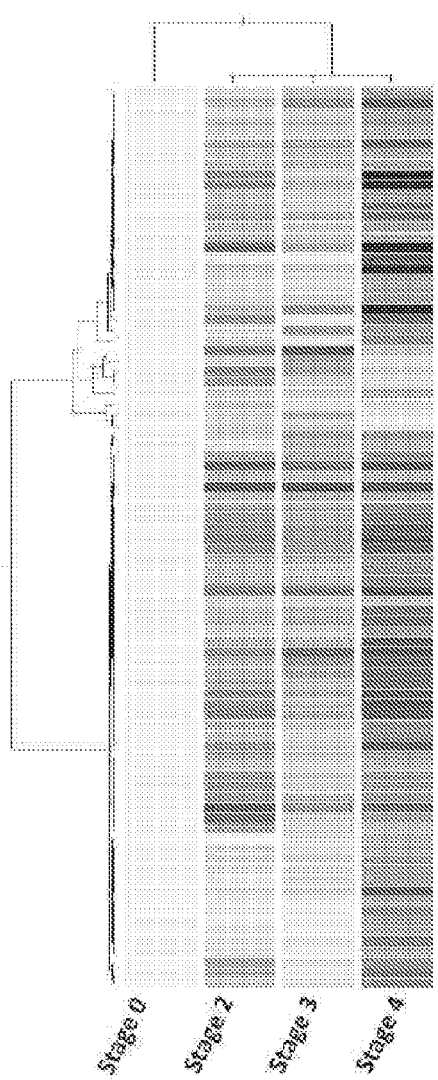
Figure 4. Heat-map of miRNAs Differentially Expressed in CSF by *Unified Staging System of LBDs*.

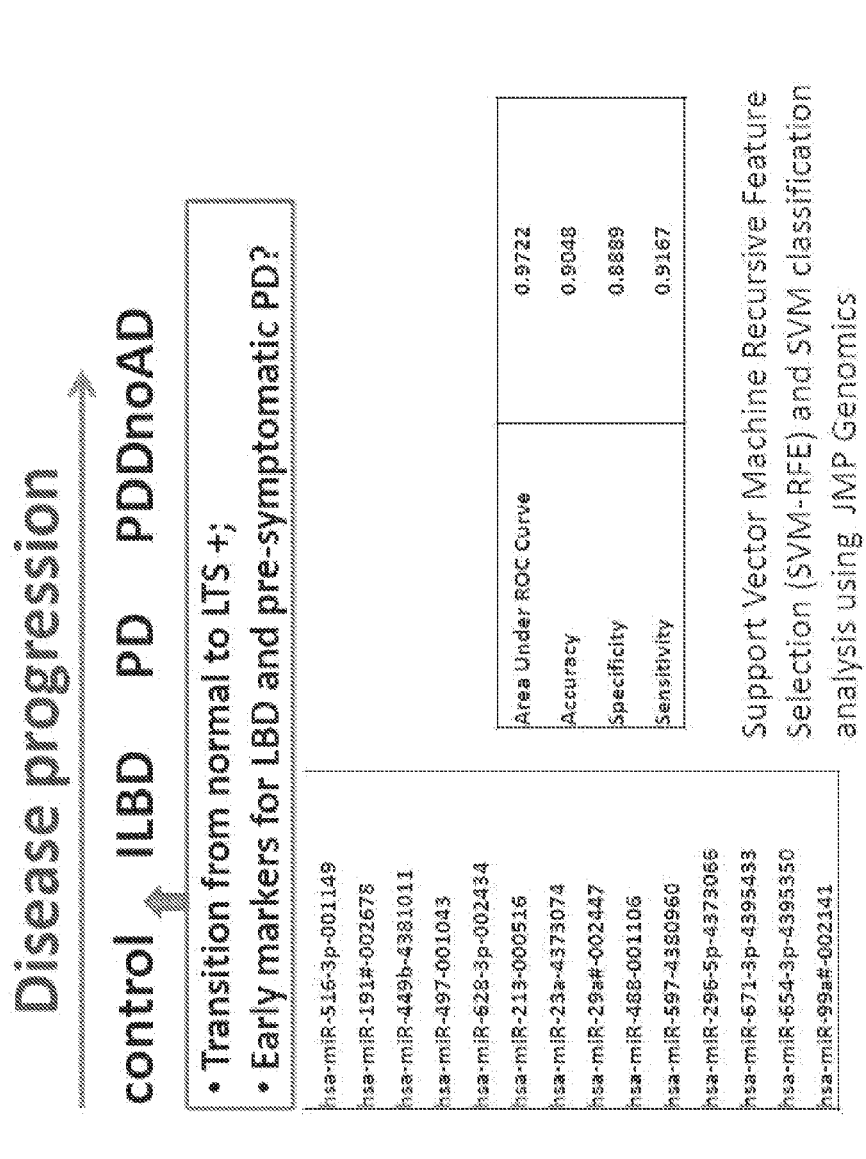
Figure 5. miRNA Signatures Which Reflect the Onset of LB Pathology

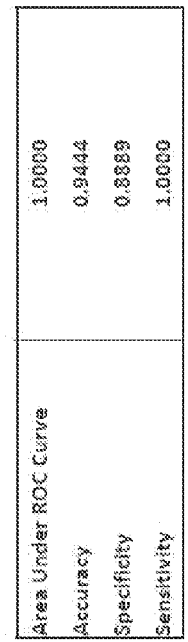
Figure 6. miRNA Signatures Which Reflect the Onset of LB Pathology

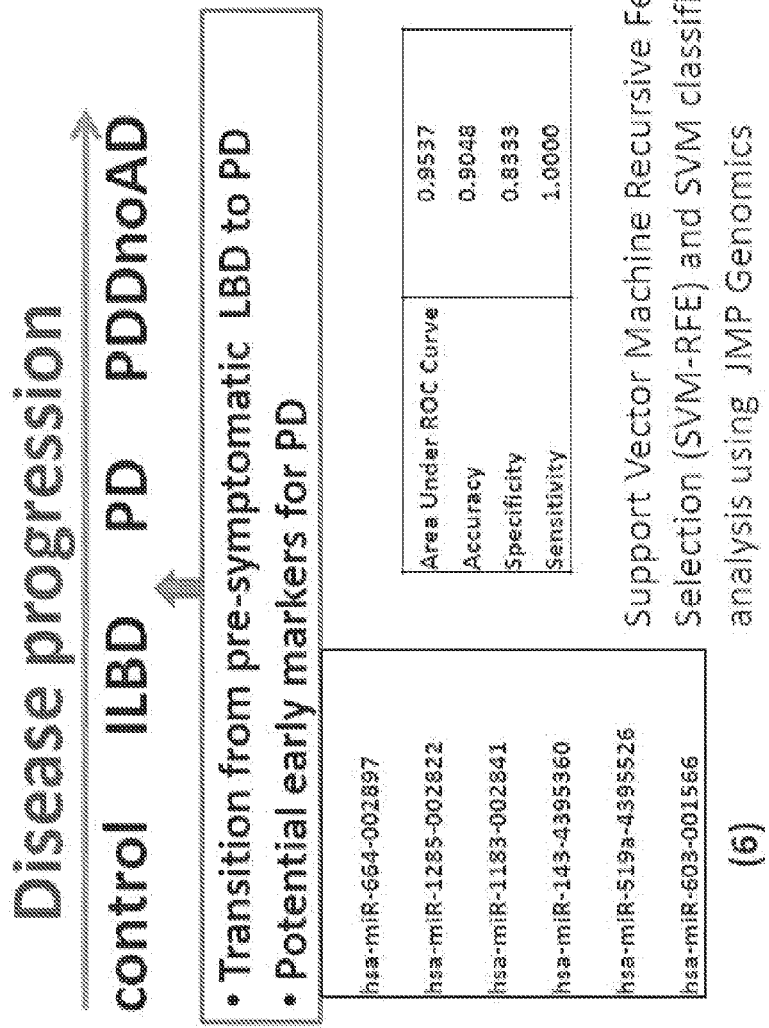
Figure 7. miRNA Signatures Which may Reflect the Onset of PD

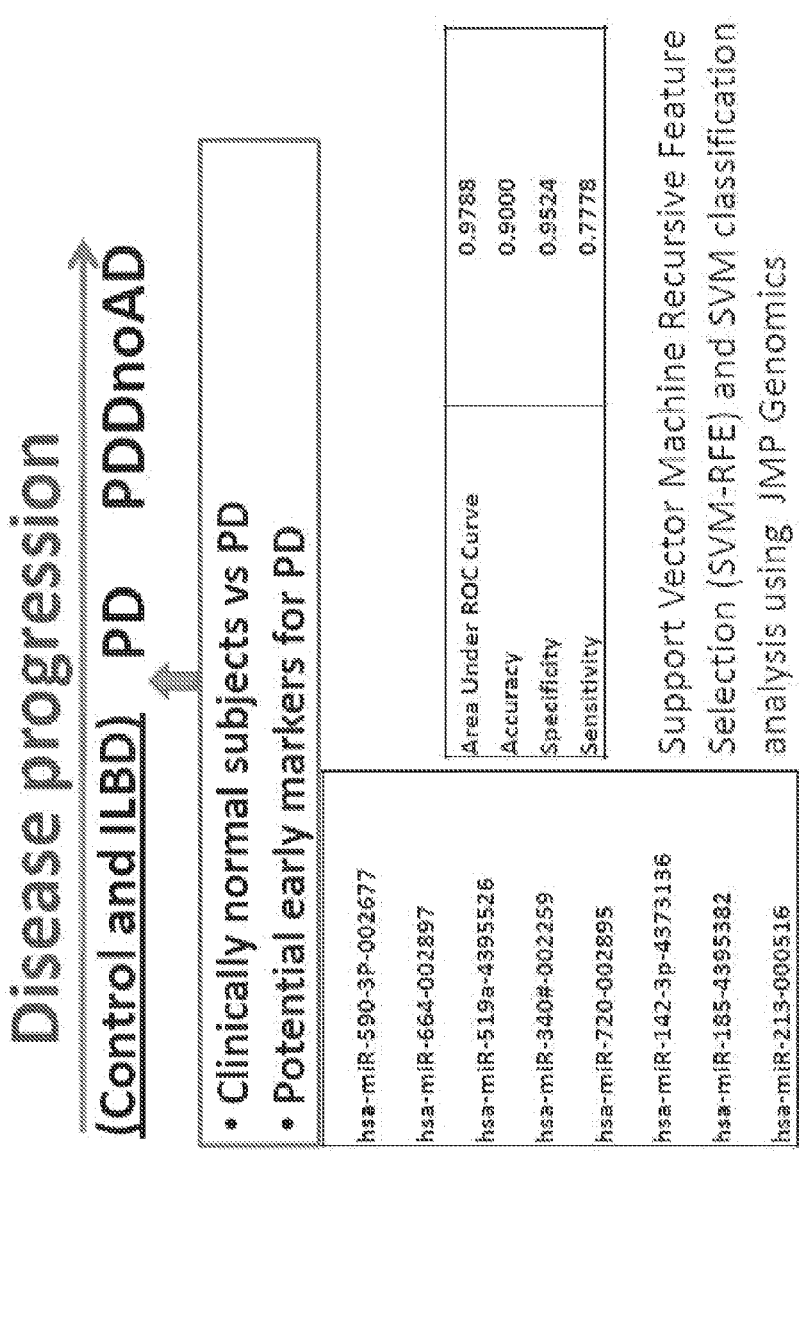
Figure 8. miRNA Signatures Which may Reflect the Onset of PD

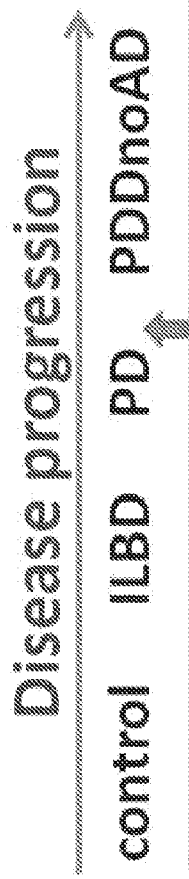
Figure 9. miRNA Signatures Reflecting the Onset of Cognitive Impairment in PD

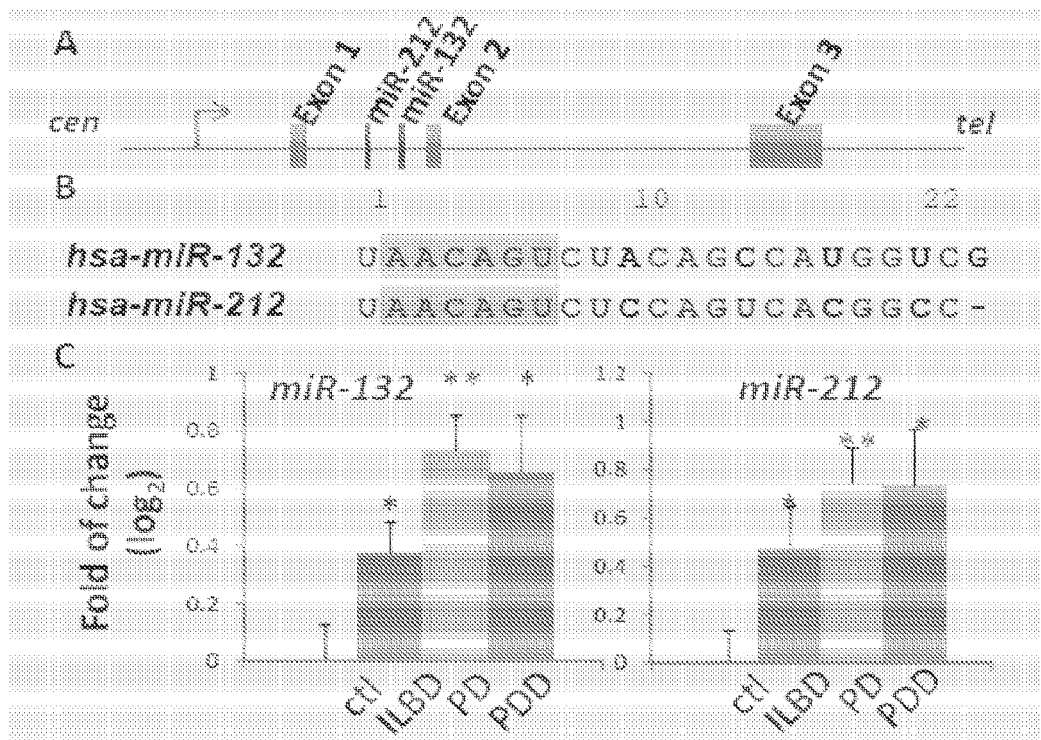

Figure 10. A. Genomic organization of miR-212/132 in the first intron of a non-coding RNA gene on human Chr1p13.3. B. Alignment of mature sequence of human miR-132 and miR-212, which share the same seed sequences (in green rectangular box). C. Relative expression levels of miR-132 and miR-212 in the putamen of normal control (Ctl), ILBD, PD and PDD subjects. The y-axis is in $\log_2$ phase. *: $p<0.05$; **: $p<0.01$ when compared to controls.

miR-132 (SEQ ID NO: 79); miR212 (SEQ ID NO: 124)

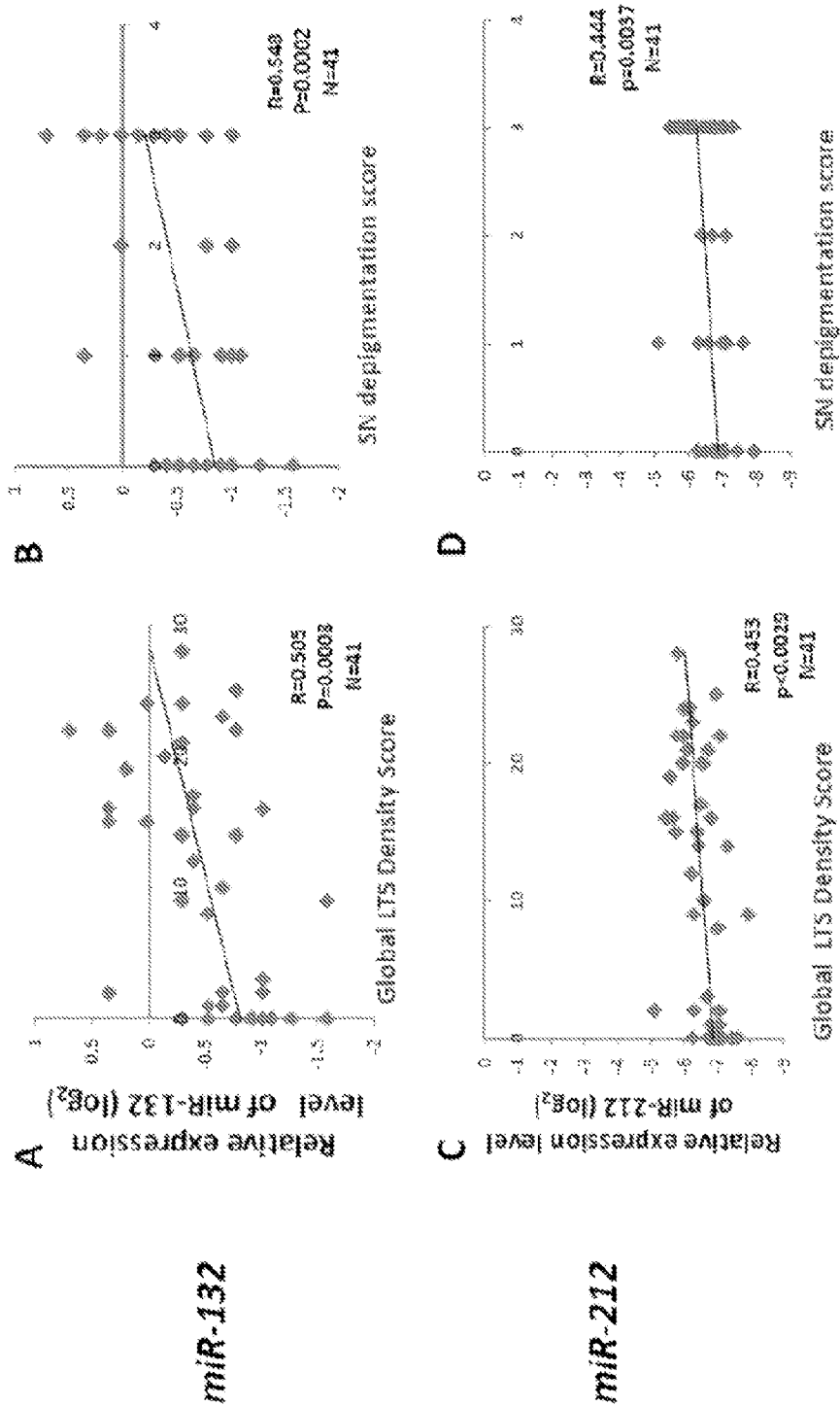
Figure 11. Expression of miR-132 and miR-212 are Positively Correlated with Global Lewy-type α-synucleinopathy (LTS) Density Scores and SN Depigmentation.

MIRNAS AS NOVEL THERAPEUTIC TARGETS AND DIAGNOSTIC BIOMARKERS FOR PARKINSONS DISEASE

This application claims the benefit under 35 U.S.C. §371 of International Application No. PCT/US2013/051849, filed Jul. 24, 2013, which claims the benefit of U.S. Provisional Application No. 61/675,603, filed Jul. 25, 2012, which are incorporated by reference herein in their entirety.

RELATED APPLICATIONS

This application claims the benefit of U.S. Provisional Application No. 61/675,603, filed Jul. 25, 2012, which is incorporated by reference herein in its entirety.

FIELD

This disclosure relates to therapeutic and diagnostic markers for Parkinson's Disease.

INTRODUCTION

MicroRNAs (miRNAs) are small, non-coding, regulatory RNAs of 18-24 nucleotides in length. Mature miRNAs regulate messenger RNAs (mRNAs) of their downstream target genes by base-pairing to their target sites to specify cleavage of the target mRNAs or to destabilize the mRNA and/or repress translation of the targeted mRNA. miRNAs are expressed in the nervous system and modulate large numbers of neuronal genes, playing important roles in neurogenesis and neurodegenerative diseases. Besides being a major level of gene expression regulation, miRNAs also are recognized as excellent biomarkers for various diseases, especially in the diagnosis and prognosis of cancer. However, the roles of miRNAs in the pathogenesis of Parkinson's Disease and their potential as biomarkers for Parkinson's Disease have not being fully studied.

SUMMARY

In some aspects, the disclosure relates to pharmaceutical compositions including an oligonucleotide that down-regulates the over-expression of at least one miRNA of SEQ ID NOs: 1-283. The oligonucleotide may be a) complementary to the nucleotide sequence of at least one of SEQ ID NOs: 1-283, or b) hybridizes under stringent conditions to a nucleotide sequence of at least one of SEQ ID NOs: 1-283.

In further aspects, the disclosure relates to methods of diagnosing Parkinson's Disease (PD) in a subject. The methods may include detecting the level of expression of at least one miRNA of SEQ ID NOs: 1-283 in a biological sample from the subject, and comparing the level of expression in the sample to the level of expression in a reference. An increased or decreased level of expression in the sample compared to the level of expression in the reference may identify the subject as having PD or who is at risk of developing PD. In some aspects, a miRNA signature may be used to diagnose a subject at risk for developing or having PD.

Another aspect of the disclosure provides methods for treating, preventing, or reducing the risk of PD associated with aberrant expression of a miRNA in a cell, tissue, or animal, the method comprising contacting the cell, tissue, or animal with a pharmaceutical composition including an oligonucleotide that down-regulates the over-expression of at least one miRNA of SEQ ID NOs: 1-283. The oligonucleotide may be a) complementary to the nucleotide sequence of at least one of SEQ ID NOs: 1-283, or b) hybridizes under stringent conditions to a nucleotide sequence of at least one of SEQ ID NOs: 1-283.

In yet another aspect of the disclosure, kits are provided for performing measurement of a miRNA signature, the miRNA signature comprising at least one miRNA of SEQ ID NOs: 1-283, wherein the kit comprises reagents for measuring an expression level of at least one miRNA of SEQ ID NOs: 1-283.

The disclosure provides for other aspects and embodiments that will be apparent in light of the following detailed description and accompanying Figures.

BRIEF DESCRIPTION OF THE DRAWINGS

FIG. 1 is a heat-map of miRNAs differentially expressed in the putamen by clinical diagnosis.

FIG. 2 is a heat-map of miRNAs differentially expressed in the putamen by unified staging system for Lewy-body disorders (LBDs).

FIG. 3 is a heat-map of miRNAs differentially expressed in cerebrospinal fluid (CSF) by clinical diagnosis.

FIG. 4 is a heat-map of miRNAs differentially expressed in CSF by unified staging system of LBDs.

FIG. 5 is a diagram of miRNA signatures that may be used to reflect the onset of Lewy body (LB) pathology.

FIG. 6 is a diagram of miRNA signatures that may be used to reflect the onset of LB pathology.

FIG. 7 is a diagram of miRNA signatures that may be used to reflect the onset of PD.

FIG. 8 is a diagram of miRNA signatures that may be used to reflect the onset of PD.

FIG. 9 is a diagram of miRNA signatures that may be used to reflect the onset of cognitive impairment in PD.

FIG. 10 is a diagram of the genomic organization of miR-212/132 in the first intron of a non-coding RNA gene on human Chr1p13.3.

FIGS. 11A-D are graphs of the expression of miR-132 and miR-212.

DETAILED DESCRIPTION

In a broad sense, the disclosure relates to therapeutic and diagnostic markers for Parkinson's Disease (PD). The present invention relates to the discovery of differential expression levels of various miRNAs in PD compared to normal tissue.

miRNAs are newly recognized, small, regulatory RNAs, which regulate gene expression by repressing translation and/or break down mRNAs of their downstream target genes. Misregulation of miRNAs in the central nervous system contributes to neurodegenerative disorders. To identify miRNAs involved in the pathogenesis of PD, fresh frozen putamen and cerebrospinal fluid (CSF) samples of 10 normal control, 12 (ILBD), 10 PD, and 10 PD with dementia but no Alzheimer's disease (AD) (PDDnoAD) cases were obtained from the Sun Health Research Institute (SHRI) (Table 1 and Table 2). By Unified Staging System for Lewy body diseases (LBDs), besides 9 normal controls, these samples include 12 Stage 2, 9 Stage 3, and 11 Stage 4 samples, representing increasing severity of the diseases.

TABLE 1

Subjects Classified by Clinical Diagnosis and Unified Staging System for LBDs (USSLBD)

| Diagnosis | Stages | | | | |
|---|---|---|---|---|---|
| | Stage 0 | Stage 2 | Stage 3 | Stage 4 | total |
| Control | 9 | | | | 9 |
| ILBD | | 7 | 5 | | 12 |
| PD | | 3 | 2 | 5 | 10 |
| PDD no AD | | 2 | 2 | 6 | 10 |
| Total | 9 | 12 | 9 | 11 | 41 |

Beach T G et al. Unified staging system for Lewy body disorders (LBDs): correlation with nigrostriatal degeneration, cognitive impairment and motor dysfunction. Acta Neuropathol. 2009, 117; 613-634.
Classification of subjects with LBDs by Lewy-type α-synucleinopathy (LTS) distributions:
Stage 0: No LTS. Control group.
Stage 1: Olfactory bulb only;
Stage 2: Brainstem or Limbic predominant;
Stage 3: Brainstem and Limbic;
Stage 4: Neocortical.

Subsequently, miRNA-proof total RNA from all putamen and CSF samples was isolated using a mirVana™ miRNA isolation system (Life Technologies). On average, 0.69+/−0.06 μg of total RNA/mg putamen tissue (n=41); and 2.74+/−0.21 μg of total RNA/mL CSF samples (n=41) was obtained. There was no significant difference in quantity of total RNA isolated from different diagnostic groups. Subsequently, miRNA profiling in all putamen (n=41) and CSF total RNA (n=41) was performed using the Taqman miRNA microarrays (Applied Biosystem), which detected 754 known human miRNAs in total, to establish miRNA transcriptomes of the putamen and CSF of all 41 cases.

By comparison of these miRNA-expression profiles, miRNAs differentially expressed in the putamen and CSF among different groups classified by clinical diagnosis, by Unified Staging System for LBD, and by the extent of Substantia Nigra (SN) neuron depigmentation were identifed. As further detailed in the Examples, expression profiles were analyzed using a two-tailed t test between two groups. Significant differential expression was identified as p<0.05 and ≥2 fold changes, including both increased and decreased expression levels by ≥2 folds. Exemplary miRNAs (SEQ ID NOs: 1-283) are shown in Table 39. In some embodiments, at least one miRNA selected from SEQ ID NOs: 1-283 may have increased or decreased expression relative to a reference, control, or normal sample by at least about 1.5-fold, at least about 1.6-fold, at least about 1.7-fold, at least about 1.8-fold, at least about 1.9-fold, at least about 2.0-fold, at least about 2.1-fold, at least about 2.2-fold, at least about 2.3-fold, at least about 2.4-fold, at least about 2.5-fold, at least about 2.6-fold, at least about 2.7-fold, at least about 2.8-fold, at least about 2.9-fold, at least about 3.0-fold, at least about 3.1-fold, at least about 3.2-fold, at least about 3.3-fold, at least about 3.4-fold, at least about 3.5-fold, at least about 3.6-fold, at least about 3.7-fold, at least about 3.8-fold, at least about 3.9-fold, or at least about 4.0-fold.

TABLE 2

Main basic characteristics of the study subjects classified by clinical diagnosis.

| | No. | age* | gender (% M) | ApoE-s4 (%) | PMI (mean +/− SD) | MMSE** | UPDRS*** | SN pigmented neuron loss score**** | α-Synuclein density score (average +/− SD) |
|---|---|---|---|---|---|---|---|---|---|
| control | 9 | 82.1 +/− 6.8 (73-97) | 60 | 22.0 | 2.4 +/− 0.6 | 29.0 (1.3) (9) | 7.0 (5.4) (9) | none (6), mild (3) | 0 |
| ILBD | 12 | 86.3 +/− 4.85 (73-91) | 67 | 16.7 | 2.7 +/− 0.6 | 28.0 (1.7) (8) | 7.0 (5.1) (7) | none (5), mild (3), mod (1), severe (3) | 8.6 +/− 8.1 |
| PD | 10 | 79.4 +/− 5.9 (72-90) | 55 | 18.2 | 6.2 +/− 4.2 | 26.8 (3.3) (4) | 9.6 (14.9) (6) | mile (1), mod (2), severe (8) | 18.0 +/− 5.3 |
| PDD (no AD) | 10 | 76.1 +/− 5.9 (69-84) | 60 | 20.0 | 3.0 +/− 1.4 | 17.1 (10.0) (7) | 25.3 (39.3) (6) | none (1), severe (9) | 19.1 +/− 5.2 |

*age is presented by average +/− standard deviation (range);

**MMSE is presented by, average (standard deviation) (number of objects with MMSE data);

***UPDRS is presented by average (standard deviation) (number of objects with MMSE data), and was obtained from subjects who were in the "off state" with respect to dopaminergic therapeutic effects.

TABLE 39

Sequences of exemplary miRNAs.

| | miRNA | Sequences | SEQ ID NO |
|---|---|---|---|
| miRNA signature distinguishing control vs PD | hsa_miR_590_3P_002677 | UAAUUUUAUGUAUAAGCUAGU | 1 |
| | hsa_miR_213_000516 | ACCAUCGACCGUUGAUUGUACC | 2 |
| | hsa_miR_9#_002231 | AUAAAGCUAGAUAACCGAAAGU | 3 |
| | hsa_miR_191#_002678 | GCUGCGCUUGGAUUUCGUCCCC | 4 |
| | hsa_miR_497_001043 | CAGCAGCACACUGUGGUUUGU | 5 |
| | hsa_miR_664_002897 | UAUUCAUUUAUCCCCAGCCUACA | 6 |
| | hsa_miR_99a#_002141 | CAAGCUCGCUUCUAUGGGUCUG | 7 |
| | hsa_miR_1183_002841 | CACUGUAGGUGAUGGUGAGAGUGGGCA | 8 |
| | hsa_miR_340#_002259 | UCCGUCUCAGUUACUUUAUAGC | 9 |
| | hsa_miR_628_3p_002434 | UCUAGUAAGAGUGGCAGUCGA | 10 |
| | rno_miR_7#_001338 | CAACAAAUCACAGUCUGCCAUA | 11 |
| | hsa_miR_29a#_002447 | ACUGAUUUCUUUUGGUGUUCAG | 12 |
| | hsa_miR_142_3p_4373136 | UGUAGUGUUUCCUACUUUAUGGA | 13 |
| miRNA signature distinguishing (Control + ILBD) vs PD | hsa-miR-590-3P-002677 | UAAUUUUAUGUAUAAGCUAGU | 14 |
| | hsa-miR-664-002897 | UAUUCAUUUAUCCCCAGCCUACA | 15 |
| | hsa-miR-519a-4395526 | AAAGUGCAUCCUUUUAGAGUGU | 16 |
| | hsa-miR-340#-002259 | UCCGUCUCAGUUACUUUAUAGC | 17 |
| | hsa-miR-720-002895 | UCUCGCUGGGGCCUCCA | 18 |
| | hsa-miR-142-3p-4373136 | UGUAGUGUUUCCUACUUUAUGGA | 19 |
| | hsa-miR-185-4395382 | UGGAGAGAAAGGCAGUUCCUGA | 20 |
| | hsa-miR-213-000516 | ACCAUCGACCGUUGAUUGUACC | 21 |
| miRNA signature distinguishing ILBD vs PD | hsa-miR-664-002897 | UAUUCAUUUAUCCCCAGCCUACA | 22 |
| | hsa-miR-1285-002822 | UCUGGGCAACAAAGUGAGACCU | 23 |
| | hsa-miR-1183-002841 | CACUGUAGGUGAUGGUGAGAGUGGGCA | 24 |
| | hsa-miR-143-4395360 | UGAGAUGAAGCACUGUAGCUCA | 25 |
| | hsa-miR-519a-4395526 | AAAGUGCAUCCUUUUAGAGUGU | 26 |
| | hsa-miR-603-001566 | CACACACUGCAAUUACUUUUGC | 27 |
| miRNA signature distinguishing PD vs PDDnoAD | hsa_miR_590_3P_002677 | UAAUUUUAUGUAUAAGCUAGU | 28 |
| | hsa_miR_213_000516 | ACCAUCGACCGUUGAUUGUACC | 29 |
| | hsa_miR_409_3p_002332 | GAAUGUUGCUCGGUGAACCCCU | 30 |
| | hsa_miR_500_4395539 | UAAUCCUUGCUACCUGGGUGAGA | 31 |
| | dme_miR_7_000268 | UGGAAGACUAGUGAUUUUGUUGU | 32 |
| | hsa_miR_206_000510 | UGGAAUGUAAGGAAGUGUGUGG | 33 |
| | hsa_miR_629_001562 | GUUCUCCCAACGUAAGCCCAGC | 34 |
| All miRNA differentially expressed and/or correlated with clinical/pathological findings | dme-miR-7-000268 | UGGAAGACUAGUGAUUUUGUUGU | 35 |
| | hsa-let-7c-4373167 | UGAGGUAGUAGGUUGUAUGGUU | 36 |
| | hsa-let-7d-4395394 | AGAGGUAGUAGGUUGCAUAGU | 37 |
| | hsa-let-7f-1#-002417 | CUAUACAAUCUAUUGCCUUCCC | 38 |
| | hsa-miR-100#-002142 | CAAGCUUGUAUCUAUAGGUAUG | 39 |
| | hsa-miR-101#-002143 | UACAGUACUGUGAUAACUGAA | 40 |
| | hsa-miR-101-4395364 | CAGUUAUCACAGUGCUGAUGCU | 41 |
| | hsa-miR-105-4395278 | UCAAAUGCUCAGACUCCUGUGGU | 42 |
| | hsa-miR-106b#-002380 | CCGCACUGUGGGUACUUGCUGC | 43 |
| | hsa-miR-107-4373154 | AGCAGCAUUGUACAGGGCUAUCA | 44 |
| | hsa-miR-10b-4395329 | UACCCUGUAGAACCGAAUUUGUG | 45 |
| | hsa-miR-1183-002841 | CACUGUAGGUGAUGGUGAGAGUGGGCA | 46 |
| | hsa-miR-1201-002781 | AGCCUGAUUAAACACAUGCUCUGA | 47 |
| | hsa-miR-122-4395356 | UGGAGUGUGACAAUGGUGUUUG | 48 |
| | hsa-miR-1224-3P-002752 | CCCCACCUCCUCUCUCCUCAG | 49 |
| | hsa-miR-1226#-002758 | GUGAGGGCAUGCAGGCCUGGAUGGGG | 50 |
| | hsa-miR-1227-002769 | CGUGCCACCCUUUUCCCCAG | 51 |
| | hsa-miR-1233-002768 | UGAGCCCUGUCCUCCCGCAG | 52 |
| | hsa-miR-1238-002927 | CUUCCUCGUCUGUCUGCCCC | 53 |
| | hsa-miR-1244-002791 | AAGUAGUUGGUUUGUAUGAGAUGGUU | 54 |
| | hsa-miR-124-4373295 | UUAAGGCACGCGGUGAAUGCCA | 55 |
| | hsa-miR-1248-002870 | ACCUUCUUGUAUAAGCACUGUGCUAAA | 56 |
| | hsa-miR-1255B-002801 | CGGAUGAGCAAAGAAAGUGGUU | 57 |
| | hsa-miR-1256-002850 | AGGCAUUGACUUCUCACUAGCU | 58 |
| | hsa-miR-125a-5p-4395309 | UCCCUGAGACCCUUUAACCUGUGA | 59 |
| | hsa-miR-125b2#-002158 | UCACAAGUCAGGCUCUUGGGAC | 60 |
| | hsa-miR-125b-4373148 | UCCCUGAGACCCUAACUUGUGA | 61 |
| | hsa-miR-126#-000451 | CAUUAUUACUUUUGGUACGCG | 62 |
| | hsa-miR-1260-002896 | AUCCCACCUCUGCCACCA | 63 |
| | hsa-miR-1264-002799 | CAAGUCUUAUUUGAGCACCUGUU | 64 |
| | hsa-miR-1269-002789 | CUGGACUGAGCCGUGCUACUGG | 65 |
| | hsa-miR-1270-002807 | CUGGAGAUAUGGAAGAGCUGUGU | 66 |
| | hsa-miR-1271-002779 | CUUGGCACUUAGCAAGCACUCA | 67 |
| | hsa-miR-127-5p-4395340 | CUGAAGCUCAGAGGGCUCUGAU | 68 |
| | hsa-miR-1282-002803 | UCGUUUGCCUUUUUCUGCUU | 69 |
| | hsa-miR-1290-002863 | UGGAUUUUUGGAUCAGGGA | 70 |
| | hsa-miR-1291-002838 | UGGCCCUGACUGAAGACCAGCAGU | 71 |

TABLE 39-continued

Sequences of exemplary miRNAs.

| miRNA | Sequences | SEQ ID NO |
|---|---|---|
| hsa-miR-129-3p-4373297 | AAGCCCUUACCCCAAAAAGUAU | 72 |
| hsa-miR-1298-002861 | UUCAUUCGGCUGUCCAGAUGUA | 73 |
| hsa-miR-1300-002902 | UUGAGAAGGAGGCUGCUG | 74 |
| hsa-miR-1301-002827 | UUGCAGCUGCCUGGGAGUGACUUC | 75 |
| hsa-miR-1303-002792 | UUUAGAGACGGGGUCUUGCUCU | 76 |
| hsa-miR-130a-4373145 | CAGUGCAAUGUUAAAAGGGCAU | 77 |
| hsa-miR-130b-4373144 | CAGUGCAAUGAUGAAAGGGCAU | 78 |
| hsa-miR-132-4373143 | UAACAGUCUACAGCCAUGGUCG | 79 |
| hsa-miR-135a-4373140 | UAUGGCUUUUUAUUCCUAUGUGA | 80 |
| hsa-miR-135b#-002159 | AUGUAGGGCUAAAAGCCAUGGG | 81 |
| hsa-miR-135b-4395372 | UAUGGCUUUUCAUUCCUAUGUGA | 82 |
| hsa-miR-136#-002100 | CAUCAUCGUCUCAAAUGAGUCU | 83 |
| hsa-miR-137-4373301 | UAUUGCUUAAGAAUACGCGUAG | 84 |
| hsa-miR-138-2#-002144 | AGCUGGUGUUGUGAAUCAGGCCG | 85 |
| hsa-miR-138-4395395 | GCUAUUUCACGACACCAGGGUU | 86 |
| hsa-miR-141-4373137 | UAACACUGUCUGGUAAAGAUGG | 87 |
| hsa-miR-142-3p-4373136 | UGUAGUGUUUCCUACUUUAUGGA | 88 |
| hsa-miR-143-4395360 | UGAGAUGAAGCACUGUAGCUC | 89 |
| hsa-miR-14395333 | UGGAAUGUAAAGAAGUAUGUA | 90 |
| hsa-miR-144#-002148 | GGAUAUCAUCAUAUACUGUAAG | 91 |
| hsa-miR-144-002676 | UACAGUAUAGAUGAUGUACU | 92 |
| hsa-miR-145#-002149 | GGAUUCCUGGAAAUACUGUUCU | 93 |
| hsa-miR-145-4395389 | GUCCAGUUUUCCCAGGAAUCCCU | 94 |
| hsa-miR-146a#-002163 | CCUCUGAAAUUCAGUUCUUCAG | 95 |
| hsa-miR-146b-5p-4373178 | UGAGAACUGAAUUCCAUAGGCU | 96 |
| hsa-miR-148a-4373130 | UCAGUGCACUACAGAACUUUGU | 97 |
| hsa-miR-148b#-002160 | AAGUUCUGUUAUACACUCAGGC | 98 |
| hsa-miR-149#-002164 | AGGGAGGGACGGGGGCUGUGC | 99 |
| hsa-miR-151-5P-002642 | UCGAGGAGCUCACAGUCUAGU | 100 |
| hsa-miR-153-4373305 | UUGCAUAGUCACAAAAGUGA | 101 |
| hsa-miR-154#-000478 | AAUCAUACACGGUUGACCUAUU | 102 |
| hsa-miR-15a-4373123 | UAGCAGCACAUAAUGGUUUGUG | 103 |
| hsa-miR-181a2#-002317 | ACCACUGACCGUUGACUGUACC | 104 |
| hsa-miR-181a-4373117 | AACAUUCAACGCUGUCGGUGAGU | 105 |
| hsa-miR-183#-002270 | UAUGGCACUGGUAGAAUUCACU | 106 |
| hsa-miR-183-4395380 | GUGAAUUACCGAAGGGCCAUAA | 107 |
| hsa-miR-184-4373113 | UGGACGGAGAACUGAUAAGGGU | 108 |
| hsa-miR-18a-4395533 | UAAGGUGCAUCUAGUGCAGAUAG | 109 |
| hsa-miR-191#-002678 | GCUGCGCUUGGAUUUCGUCCCC | 110 |
| hsa-miR-192-4373108 | CUGACCUAUGAAUUGACAGCC | 111 |
| hsa-miR-193a-5p-4395392 | UGGGUCUUUGCGGGCGAGAUGA | 112 |
| hsa-miR-195-4373105 | UAGCAGCACAGAAAUAUUGGC | 113 |
| hsa-miR-196b-4395326 | UAGGUAGUUUCCUGUUGUUGGG | 114 |
| hsa-miR-197-4373102 | UUCACCACCUUCUCCACCCAGC | 115 |
| hsa-miR-198-4395384 | GGUCCAGAGGGGAGAUAGGUUC | 116 |
| hsa-miR-199a-5p-4373272 | CCCAGUGUUCAGACUACCUGUUC | 117 |
| hsa-miR-19b-4373098 | UGUGCAAAUCCAUGCAAAACUGA | 118 |
| hsa-miR-200b-4395362 | UAAUACUGCCUGGUAAUGAUGA | 119 |
| hsa-miR-202-4395474 | AGAGGUAUAGGGCAUGGGAA | 120 |
| hsa-miR-203-4373095 | GUGAAAUGUUUAGGACCACUAG | 121 |
| hsa-miR-206-000510 | UGGAAUGUAAGGAAGUGUGUGG | 122 |
| hsa-miR-211-4373088 | UUCCCUUUGUCAUCCUUCGCCU | 123 |
| hsa-miR-212-4373087 | UAACAGUCUCCAGUCACGGCC | 124 |
| hsa-miR-213-000516 | ACCAUCGACCGUUGAUUGUACC | 125 |
| hsa-miR-21-4373090 | UAGCUUAUCAGACUGAUGUUGA | 126 |
| hsa-miR-217-4395448 | UACUGCAUCAGGAACUGAUUGGA | 127 |
| hsa-miR-218-4373081 | UUGUGCUUGAUCUAACCAUGU | 128 |
| hsa-miR-219-2-3p-4395501 | AGAAUUGUGGCUGGACAUCUGU | 129 |
| hsa-miR-22#-002301 | AGUUCUUCAGUGGCAAGCUUUA | 130 |
| hsa-miR-220b-4395317 | CCACCACCGUGUCUGACACUU | 131 |
| hsa-miR-222#-002097 | CUCAGUAGCCAGUGUAGAUCCU | 132 |
| hsa-miR-223-4395406 | UGUCAGUUUGUCAAAUACCCCA | 133 |
| hsa-miR-23a-4373074 | AUCACAUUGCCAGGGAUUUCC | 134 |
| hsa-miR-24-1#-002440 | UGCCUACUGAGCUGAUAUCAGU | 135 |
| hsa-miR-25-4373071 | CAUUGCACUUGUCUCGGUCUGA | 136 |
| hsa-miR-26a-2#-002115 | CCUAUUCUUGAUUACUUGUUUC | 137 |
| hsa-miR-26b#-002444 | CCUGUUCUCCAUUACUUGGCUC | 138 |
| hsa-miR-27a#-002445 | AGGGCUUAGCUGCUUGUGAGCA | 139 |
| hsa-miR-27b-4373068 | UUCACAGUGGCUAAGUUCUGC | 140 |
| hsa-miR-28-3p-4395557 | CACUAGAUUGUGAGCUCCUGGA | 141 |
| hsa-miR-296-3p-4395212 | GAGGGUUGGGUGGAGGCUCUCC | 142 |
| hsa-miR-296-5p-4373066 | AGGGCCCCCCCUCAAUCCUGU | 143 |
| hsa-miR-29a#-002447 | ACUGAUUUCUUUUGGUGUUCAG | 144 |
| hsa-miR-29a-4395223 | UAGCACCAUCUGAAAUCGGUUA | 145 |
| hsa-miR-29c-4395171 | UAGCACCAUUUGAAAUCGGUUA | 146 |

TABLE 39-continued

Sequences of exemplary miRNAs.

| miRNA | Sequences | SEQ ID NO |
|---|---|---|
| hsa-miR-302a-4378070 | UAAGUGCUUCCAUGUUUUGGUGA | 147 |
| hsa-miR-302d-000535 | UAAGUGCUUCCAUGUUUGAGUGU | 148 |
| hsa-miR-30a-3p-000416 | CUUUCAGUCGGAUGUUUGCAGC | 149 |
| hsa-miR-30b-4373290 | UGUAAACAUCCUACACUCAGCU | 150 |
| hsa-miR-30c-1#-002108 | CUGGGAGAGGGUUGUUUACUCC | 151 |
| hsa-miR-30e-3p-000422 | CUUUCAGUCGGAUGUUUACAGC | 152 |
| hsa-miR-31#-002113 | UGCUAUGCCAACAUAUUGCCAU | 153 |
| hsa-miR-31-4395390 | AGGCAAGAUGCUGGCAUAGCU | 154 |
| hsa-miR-320B-002844 | AAAAGCUGGGUUGAGAGGGCAA | 155 |
| hsa-miR-324-5p-4373052 | CGCAUCCCCUAGGGCAUUGGUGU | 156 |
| hsa-miR-326-4373050 | CCUCUGGGCCCUUCCUCCAG | 157 |
| hsa-miR-328-4373049 | CUGGCCCUCUCUGCCCUUCCGU | 158 |
| hsa-miR-330-5p-4395341 | UCUCUGGGCCUGUGUCUUAGGC | 159 |
| hsa-miR-337-3p-002157 | CUCCUAUAUGAUGCCUUUCUUC | 160 |
| hsa-miR-338-3p-4395363 | UCCAGCAUCAGUGAUUUUGUUG | 161 |
| hsa-miR-339-5p-4395368 | UCCCUGUCCUCCAGGAGCUCACG | 162 |
| hsa-miR-33b-4395196 | GUGCAUUGCUGUUGCAUUGC | 163 |
| hsa-miR-340#-002259 | UCCGUCUCAGUUACUUUAUAGC | 164 |
| hsa-miR-340-4395369 | UUAUAAAGCAAUGAGACUGAUU | 165 |
| hsa-miR-345-4395297 | GCUGACUCCUAGUCCAGGGCUC | 166 |
| hsa-miR-34a#-002316 | CAAUCAGCAAGUAUACUGCCCU | 167 |
| hsa-miR-34a-4395168 | UGGCAGUGUCUUAGCUGGUUGU | 168 |
| hsa-miR-34b-000427 | UAGGCAGUGUCAUUAGCUGAUUG | 169 |
| hsa-miR-34c-5p-4373036 | AGGCAGUGUAGUUAGCUGAUUGC | 170 |
| hsa-miR-362-5p-4378092 | AAUCCUUGGAACCUAGGUGUGAGU | 171 |
| hsa-miR-363#-001283 | CGGGUGGAUCACGAUGCAAUUU | 172 |
| hsa-miR-363-4378090 | AAUUGCACGGUAUCCAUCUGUA | 173 |
| hsa-miR-365-4373194 | UAAUGCCCCUAAAAAUCCUUAU | 174 |
| hsa-miR-367-4373034 | AAUUGCACUUUAGCAAUGGUGA | 175 |
| hsa-miR-373-4378073 | GAAGUGCUUCGAUUUUGGGGUGU | 176 |
| hsa-miR-374b#-002391 | CUUAGCAGGUUGUAUUAUCAUU | 177 |
| hsa-miR-374b-4381045 | AUAUAAUACAACCUGCUAAGUG | 178 |
| hsa-miR-376c-4395233 | AACAUAGAGGAAAUUCCACGU | 179 |
| hsa-miR-378-000567 | CUCCUGACUCCAGGUCCUGUGU | 180 |
| hsa-miR-380-5p-000570 | UGGUUGACCAUAGAACAUGCGC | 181 |
| hsa-miR-381-4373020 | UAUACAAGGGCAAGCUCUCUGU | 182 |
| hsa-miR-382-4373019 | GAAGUUGUUCGUGGUGGAUUCG | 183 |
| hsa-miR-383-4373018 | AGAUCAGAAGGUGAUUGUGGCU | 184 |
| hsa-miR-409-3p-002332 | GAAUGUUGCUCGGUGAACCCCU | 185 |
| hsa-miR-411-4381013 | UAGUAGACCGUAUAGCGUACG | 186 |
| hsa-miR-424#-002309 | CAAAACGUGAGGCGCUGCUAU | 187 |
| hsa-miR-424-4373201 | CAGCAGCAAUUCAUGUUUUGAA | 188 |
| hsa-miR-431-4395173 | UGUCUUGCAGGCCGUCAUGCA | 189 |
| hsa-miR-432-001026 | UCUUGGAGUAGGUCAUUGGGUGG | 190 |
| hsa-miR-448-4373206 | UUGCAUAUGUAGGAUGUCCCAU | 191 |
| hsa-miR-449b-4381011 | AGGCAGUGUAUUGUUAGCUGGC | 192 |
| hsa-miR-450a-4395414 | UUUUGCGAUGUGUUCCUAAUAU | 193 |
| hsa-miR-454-4395434 | UAGUGCAAUAUUGCUUAUAGGGU | 194 |
| hsa-miR-483-3p-002339 | UCACUCCUCUCCUCCCGUCUU | 195 |
| hsa-miR-484-4381032 | UCAGGCUCAGUCCCCUCCCGAU | 196 |
| hsa-miR-486-5p-4378096 | UCCUGUACUGAGCUGCCCCGAG | 197 |
| hsa-miR-488-4395468 | UUGAAAGGCUAUUUCUUGGUC | 198 |
| hsa-miR-489-4395469 | GUGACAUCACAUAUACGGCAGC | 199 |
| hsa-miR-497-001043 | CAGCAGCACACUGUGGUUUGU | 200 |
| hsa-miR-499-5p-4381047 | UUAAGACUUGCAGUGAUGUUUAA | 201 |
| hsa-miR-500-001046 | AUGCACCUGGGCAAGGAUUCUG | 202 |
| hsa-miR-511-4373236 | GUGUCUUUUGCUCUGCAGUCA | 203 |
| hsa-miR-516-3p-001149 | UGCUUCCUUUCAGAGGGU | 204 |
| hsa-miR-516b-4395172 | AUCUGGAGGUAAGAAGCACUUU | 205 |
| hsa-miR-517#-001113 | CCUCUAGAUGGAAGCACUGUCU | 206 |
| hsa-miR-518a-3p-4395508 | GAAAGCGCUUCCCUUUGCUGGA | 207 |
| hsa-miR-518b-4373246 | CAAAGCGCUCCCCUUUAGAGGU | 208 |
| hsa-miR-519a-4395526 | AAAGUGCAUCCUUUUAGAGUGU | 209 |
| hsa-miR-520c-3p-002400 | AAAGUGCUUCCUUUUAGAGGGU | 210 |
| hsa-miR-520D-3P-002743 | AAAGUGCUUCUCUUUGGUGGGU | 211 |
| hsa-miR-520g-4373257 | ACAAAGUGCUUCCCUUUAGAGUGU | 212 |
| hsa-miR-521-4373259 | AACGCACUUCCCUUUAGAGUGU | 213 |
| hsa-miR-539-4378103 | GGAGAAAUUAUCCUUGGUGUGU | 214 |
| hsa-miR-541-4395312 | UGGUGGGCACAGAAUCUGGACU | 215 |
| hsa-miR-543-002376 | AAACAUUCGGCGUGCACUUCUU | 216 |
| hsa-miR-545-4395378 | UCAGCAAACAUUUAUUGUGUGC | 217 |
| hsa-miR-548b-5p-4395519 | AAAAGUAAUUGUGGUUUUGGCC | 218 |
| hsa-miR-548c-5p-4395540 | AAAAGUAAUUGCGGUUUUUGCC | 219 |
| hsa-miR-548I-002909 | AAAAGUAAUUGCGGAUUUUGCC | 220 |
| hsa-miR-551b#-002346 | GAAAUCAAGCGUGGGUGAGACC | 221 |

TABLE 39-continued

Sequences of exemplary miRNAs.

| miRNA | Sequences | SEQ ID NO |
|---|---|---|
| hsa-miR-552-001520 | AACAGGUGACUGGUUAGACAA | 222 |
| hsa-miR-559-001527 | UAAAGUAAAUAUGCACCAAAA | 223 |
| hsa-miR-566-001533 | GGGCGCCUGUGAUCCCAAC | 224 |
| hsa-miR-571-001613 | UGAGUUGGCCAUCUGAGUGAG | 225 |
| hsa-miR-574-3p-4395460 | CACGCUCAUGCACACACCCACA | 226 |
| hsa-miR-577-002675 | UAGAUAAAAUAUUGGUACCUG | 227 |
| hsa-miR-582-3p-4395510 | UAACUGGUUGAACAACUGAACC | 228 |
| hsa-miR-589-001543 | UCAGAACAAAUGCCGGUUCCCAGA | 229 |
| hsa-miR-590-3P-002677 | UAAUUUUAUGUAUAAGCUAGU | 230 |
| hsa-miR-590-5p-4395176 | GAGCUUAUUCAUAAAAGUGCAG | 231 |
| hsa-miR-592-001546 | UUGUGUCAAUAUGCGAUGAUGU | 232 |
| hsa-miR-593-001547 | AGGCACCAGCCAGGCAUUGCUCAGC | 233 |
| hsa-miR-597-4380960 | UGUGUCACUCGAUGACCACUGU | 234 |
| hsa-miR-601-001558 | UGGUCUAGGAUUGUUGGAGGAG | 235 |
| hsa-miR-604-001567 | AGGCUGCGGAAUUCAGGAC | 236 |
| hsa-miR-608-001571 | AGGGGUGGUGUUGGGACAGCUCCGU | 237 |
| hsa-miR-616-4395525 | AGUCAUUGGAGGGUUUGAGCAG | 238 |
| hsa-miR-617-001591 | AGACUUCCCAUUUGAAGGUGGC | 239 |
| hsa-miR-618-4380996 | AAACUCUACUUGUCCUUCUGAGU | 240 |
| hsa-miR-622-001553 | ACAGUCUGCUGAGGUUGGAGC | 241 |
| hsa-miR-625#-002432 | GACUAUAGAACUUUCCCCCUCA | 242 |
| hsa-miR-626-001559 | AGCUGUCUGAAAAUGUCUU | 243 |
| hsa-miR-628-3p-002434 | UCUAGUAAGAGUGGCAGUCGA | 244 |
| hsa-miR-628-5p-4395544 | AUGCUGACAUAUUUACUAGAGG | 245 |
| hsa-miR-629-001562 | UGGGUUUACGUUGGGAGAACU | 246 |
| hsa-miR-630-001563 | AGUAUUCUGUACCAGGGAAGGU | 247 |
| hsa-miR-635-001578 | ACUUGGGCACUGAAACAAUGUCC | 248 |
| hsa-miR-638-001582 | AGGGAUCGCGGGCGGGUGGCGGCCU | 249 |
| hsa-miR-639-001583 | AUCGCUGCGGUUGCGAGCGCUGU | 250 |
| hsa-miR-641-001585 | AAAGACAUAGGAUAGAGUCACCUC | 251 |
| hsa-miR-644-001596 | AGUGUGGCUUUCUUAGAGC | 252 |
| hsa-miR-649-001602 | AAACCUGUGUUGUUCAAGAGUC | 253 |
| hsa-miR-652-4395463 | AAUGGCGCCACUAGGGUUGUG | 254 |
| hsa-miR-654-3p-4395350 | UAUGUCUGCUGACCAUCACCUU | 255 |
| hsa-miR-659-001514 | CUUGGUUCAGGGAGGGUCCCCA | 256 |
| hsa-miR-660-4380925 | UACCCAUUGCAUAUCGGAGUUG | 257 |
| hsa-miR-661-001606 | UGCCUGGGUCUCUGGCCUGCGCGU | 258 |
| hsa-miR-663B-002857 | GGUGGCCCGGCCGUGCCUGAGG | 259 |
| hsa-miR-664-002897 | UAUUCAUUUAUCCCCAGCCUACA | 260 |
| hsa-miR-671-3p-4395433 | UCCGGUUCUCAGGGCUCCACC | 261 |
| hsa-miR-708-4395452 | AAGGAGCUUACAAUCUAGCUGGG | 262 |
| hsa-miR-720-002895 | UCUCGCUGGGGCCUCCA | 263 |
| hsa-miR-758-4395180 | UUUGUGACCUGGUCCACUAACC | 264 |
| hsa-miR-767-5p-001993 | UGCACCAUGGUUGUCUGAGCAUG | 265 |
| hsa-miR-769-5p-001998 | UGAGACCUCUGGGUUCUGAGCU | 266 |
| hsa-miR-873-4395467 | GCAGGAACUUGUGAGUCUCCU | 267 |
| hsa-miR-876-3p-4395336 | UGGUGGUUUACAAAGUAAUUCA | 268 |
| hsa-miR-885-5p-4395407 | UCCAUUACACUACCCUGCCUCU | 269 |
| hsa-miR-886-3p-4395305 | CGCGGGUGCUUACUGACCCUU | 270 |
| hsa-miR-886-5p-4395304 | CGGGUCGGAGUUAGCUCAAGCGG | 271 |
| hsa-miR-9#-002231 | AUAAAGCUAGAUAACCGAAAGU | 272 |
| hsa-miR-920-002150 | GGGGAGCUGUGGAAGCAGUA | 273 |
| hsa-miR-922-002152 | GCAGCAGAGAAUAGGACUACGUC | 274 |
| hsa-miR-92a-1#-002137 | AGGUUGGGAUCGGUUGCAAUGCU | 275 |
| hsa-miR-92a-4395169 | UAUUGCACUUGUCCCGGCCUGU | 276 |
| hsa-miR-9-4373285 | UCUUUGGUUAUCUAGCUGUAUGA | 277 |
| hsa-miR-98-4373009 | UGAGGUAGUAAGUUGUAUUGUU | 278 |
| hsa-miR-99a#-002141 | CAAGCUCGCUUCUAUGGGUCUG | 279 |
| hsa-miR-99b-4373007 | CACCCGUAGAACCGACCUUGCG | 280 |
| mmu-let-7d#-001178 | CUAUACGACCUGCUGCCUUUCU | 281 |
| rno-miR-29c#-001818 | UGACCGAUUUCUCCUGGUGUUC | 282 |
| rno-miR-7#-001338 | CAACAAAUCACAGUCUGCCAUA | 283 |

As shown in the Examples discovered are miRNAs that are useful as diagnostic markers and therapeutic targets for the treatment and prevention of Parkinson's Disease and related disorders. As used herein, disorders related to Parkinson's Disease may include, but are not limited to, Alzheimer's, dementia, cognitive impairment, pre-symptomatic Parkinson's Disease, and Lewis Body disease.

miRNA or microRNA refer to 19-25 nucleotide (nt) non-coding RNAs derived from endogenous genes that act as post-transcriptional regulators of gene expression. They are processed from longer (ca 70-80 nt) hairpin-like precursors termed pre-miRNAs by the RNAse III enzyme Dicer. miRNAs assemble in ribonucleoprotein complexes termed miRNPs and recognise their target sites by antisense complementarity thereby mediating down-regulation of their target genes. Near-perfect or perfect complementarity between the miRNA and its target site results in target mRNA cleavage, whereas limited complementarity between the miRNA and the target site results in translational inhibition of the target gene.

Compositions

In certain aspects, provided are pharmaceutical compositions. The pharmaceutical compositions may include an oligonucleotide that down-regulates the over-expression of at least one miRNA of SEQ ID NOs: 1-283. The oligonucleotide may be complementary to the nucleotide sequence of at least one of SEQ ID NOs: 1-283. The oligonucleotide may hybridize under stringent conditions to a nucleotide sequence of at least one of SEQ ID NOs: 1-283. The oligonucleotide may comprise any nucleic acid. "Nucleic acid" includes double- and single-stranded DNA of different lengths, as well as double- and single stranded RNA of different lengths, or synthetic variants thereof. Thus, the nucleic acid may be, for example, DNA, cDNA, RNA, sRNA, locked nucleotide acid (LNA), HNA, peptide nucleic acid (PNA), or any other variant hereof.

As used herein, "complementary" or "substantially complementary" refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 80% of the nucleotides of the other strand, usually at least about 90% to 95%, and more preferably from about 98 to 100%

The oligonucleotide may be at least about 10 nucleotides (nt), at least about 11 nt, at least about 12 nt, at least about 13 nt, at least about 14 nt, at least about 15 nt, at least about 16 nt, at least about 17 nt, at least about 18 nt, at least about 19 nt, or at least about 20 nt in length. The oligonucleotide may be less than about 100 nt, less than about 90 nt, less than about 80 nt, less than about 70 nt, less than about 60 nt, or less than about 50 nt in length. This may include ranges of about 10 nt to about 50 nt, about 12 nt to about 40 nt, or about 15 nt to about 30 nt in length.

The oligonucleotide may be capable of reducing expression of the miRNA by at least about 10%, at least about 20%, at least about 30%, at least about 40%, at least about 50%, or at least about 60%. The oligonucleotide may be capable of reducing expression of the miRNA by less than about 99%, less than about 98%, less than about 95%, less than about 90%, less than about 85%, less than about 80%, or less than about 75%. This may include ranges of about 10% to about 99%, about 20% to about 98%, about 30% to about 90%, or about 40% to about 80%.

The oligonucleotide may be chemically modified. Chemical modifications may include addition of an imaging agent or reporter molecule. As used herein, an "imaging agent" or "reporter molecule" is any entity which enhances visualization or detection of the oligonucleotide. Any type of detectable reporter molecule/imaging agent can be used in the methods disclosed herein. Such detectable molecules are known in the art and include, for example, magnetic beads, fluorophores, radionuclides, nuclear stains (e.g., DAPI). For example, an imaging agent can include a compound that comprises an unstable isotope (i.e., a radionuclide) or a fluorescent moiety, such as Cy-5, Alexa 647, Alexa 555, Alexa 488, fluorescein, rhodamine, and the like. Suitable radionuclides include both alpha- and beta-emitters. In some embodiments, the targeting vehicle is labeled. In other embodiments, suitable radioactive moieties include labeled polynucleotides and polypeptides which can be coupled to the targeting vehicle.

In some embodiments, the imaging agent comprises a radionuclide such as, for example, a radionuclide that emits low-energy electrons (e.g., those that emit photons with energies as low as 20 keV). Such nuclides can irradiate the cell to which they are delivered without irradiating surrounding cells or tissues. Non-limiting examples of radionuclides that are can be delivered to cells include $^{137}$Cs, $^{103}$Pd, $^{111}$In, $^{125}$I, $^{211}$At, $^{212}$Bi and $^{213}$Bi, among others known in the art. Further imaging agents suitable for delivery to a cell in accordance with some embodiments include paramagnetic species for use in MRI imaging, echogenic entities for use in ultrasound imaging, fluorescent entities for use in fluorescence imaging (including quantum dots), and light-active entities for use in optical imaging. A suitable species for MRI imaging is a gadolinium complex of diethylenetriamine pentacetic acid (DTPA). For positron emission tomography (PET), $^{18}$F or $^{11}$C may be delivered.

Methods

In further aspects, the disclosure relates to methods of diagnosing Parkinson's Disease (PD) in a subject. The methods may include detecting the level of expression of at least one miRNA of SEQ ID NOs: 1-283 in a biological sample from the subject, and comparing the level of expression in the sample to the level of expression in a reference. An increased or decreased level of expression in the sample compared to the level of expression in the reference may identify the subject as having PD or who is at risk of developing PD.

Various detection methods that can be employed for the methods described herein, and the present invention includes all the mentioned methods, but is not limited to any of these. Detection methods may include use of a probe. A probe is a specific sequence of a nucleic acid used to detect nucleic acids by hybridization. A probe may be labelled, tagged or immobilized or otherwise modified according to the requirements of the detection method chosen. A label or a tag is an entity making it possible to identify a compound to which it is associated. It is within the scope of the present invention to employ probes that are labelled or tagged by any means known in the art such as but not limited to: radioactive labelling, fluorescent labelling and enzymatic labelling. Furthermore the probe, labeled or not, may be immobilized to facilitate detection according to the detection method of choice and this may be accomplished according to the preferred method of the particular detection method. Detection methods may also include in situ hybridization, PCR, microarrays, Northern blot analysis, and affinity matrices.

In some embodiments, RT-PCR may be used as the detection method. In some embodiments, the detection method may include quantitative real-time RT-PCR, for example, the TaqMan® MicroRNA assay (Applied Biosystems) may be used for detection of expression of the miRNAs described herein.

In some embodiments, a kit may be provided with reagents to measure at least one of the miRNAs. In some embodiments, a kit may be provided to measure a miRNA signature. By way of non-limiting example, the kit may include reagents to measure a miRNA signature where the miRNA signature includes at least one of SEQ ID NOs: 204, 110, 192, 200, 244, 21, 134, 144, 198, 234, 143, 261, 255, and 179 (miR-516-3p, miR-191#, miR-449b, miR-497, miR-628-3p, miR-213, miR-23a, miR-29a#, miR-488, miR-597, miR-296-5p, miR-671-3p, miR-654-3p, and miR-99a#)

or a combination thereof and in some embodiments includes all 14. An embodiment of the kit may include reagents to measure a miRNA signature where the miRNA signature includes at least one of SEQ ID NOs: 1-13, (miR-590-3p, miR-213, miR-9#, miR-191#, miR-497, miR-664, miR-99a#, miR-1183, miR-340#, miR-628-3p, miR-7#, miR-29a#, miR-142-3p) or combinations thereof and in some embodiments includes all 13. An embodiment of the kit may include reagents to measure a miRNA signature where the miRNA signature includes at least one of SEQ ID NOs: 14-21 (miR-590-3p, miR-664, miR-519a, miR-340#, miR-720, miR-142-3p, miR-185, and miR-213) or combinations thereof an in some embodiments includes all 8. An embodiment of the kit may include reagents to measure a miRNA signature where the miRNA signature includes at least one of SEQ ID NOs: 22-27 (miR-664, miR-1285, miR-1183, miR-143, miR-519a, miR-603) or combinations thereof an in some embodiments includes all 6. An embodiment of the kit may include reagents to measure a miRNA signature where the miRNA signature includes at least one of SEQ ID NOs: 28-34 (miR-590-3p, miR-213, miR-409-3p, miR-500, miR-7, miR-206, and miR-629) or combinations thereof an in some embodiments includes all 7. Additional combinations for the kit for measuring a miRNA signature are also possible.

In some embodiments, the expression level of one or more miRNAs of SEQ ID NOS 1-283 may be compared to a reference expression level using statistical analysis with a computer to implement the statistical analysis. In some embodiments Support Vector Machine Recursive Feature Selection (SVM-RFE) and SVM classification analysis from JMP Genomics (SAS Institute) is used to compare the miRNA expression levels. In some embodiments, the data for the array assays will be first analyzed using RQ manager 1.2 software (Applied Biosystems) to obtain raw expression levels of all the miRNAs in each sample, represented by $C^T$. In some embodiments, the miRNA expression profiles of ILBD, PD, and PDDnoAD patients may be compared to age-matched normal controls in the CSF or SNs. The miRNA profiles of ILBD, PD, and PDDnoAD patients may be compared to each other. Changes in the levels of miRNA expression in each pair will be evaluated by the DDCt or $\Delta(\Delta C^T)$. In some embodiments, StatMiner software (Integromics) may be used for bioinformatic and statistical analysis.

The subject may be any mammal. Mammals include including humans, mice, rats, rabbits, cats, and dogs. The subject is preferably human. The subject may be predisposed for a disease or suffering from a disease.

A sample may be a small part of a subject, representative of the whole, and may be constituted by a biopsy or a body fluid sample. Biopsies are small pieces of tissue and may be fresh, frozen or fixed, such as formalin-fixed and paraffin embedded (FFPE). Body fluid samples may be blood, plasma, serum, urine, sputum, cerebrospinal fluid, milk, or ductal fluid samples and may likewise be fresh, frozen or fixed. Suitably, the sample comprises blood. Samples may be removed surgically, by extraction, i.e. by hypodermic or other types of needles, by microdissection, or laser capture.

The reference may be any suitable control sample known in the art, such as, for example, a sample from a normal, healthy subject. The reference may be a sample from the same subject prior to demonstration of disease symptoms or prior to diagnosis with Parkinson's Disease. The reference may be a "standardized" sample, such as a sample comprising material or data from several samples, preferably also from several individuals. A standardized sample may comprise either normal or diseased sample material or data.

Before analyzing the sample, it may be desirable to perform one or more sample preparation operations upon the sample. Typically, these sample preparation operations will include such manipulations as concentration, suspension, extraction of intracellular material, e.g., nucleic acids from tissue/whole cell samples and the like, amplification of nucleic acids, fragmentation, transcription, labeling and/or extension reactions. Nucleic acids, especially RNA and specifically miRNA can be isolated using any techniques known in the art. There are two main methods for isolating RNA: phenol-based extraction and silica matrix or glass fiber filter (GFF)-based binding. Phenol-based reagents contain a combination of denaturants and RNase inhibitors for cell and tissue disruption and subsequent separation of RNA from contaminants. Phenol-based isolation procedures can recover RNA species in the 10-200-nucleotide range e.g., miRNAs, 5S rRNA, 5.8S rRNA, and U1 snRNA. If a sample of "total" RNA was purified by the popular silica matrix column or GFF procedure, it may be depleted in small RNAs. Extraction procedures such as those using Trizol or TriReagent, however will purify all RNAs, large and small, and are the recommended methods for isolating total RNA from biological samples that will contain miRNAs/siRNAs. Any method required for the processing of a sample prior to detection by any of the herein mentioned methods falls within the scope of the present invention. These methods are typically well known by a person skilled in the art.

Other aspects of the disclosure provide methods for treating, preventing, or reducing the risk of PD associated with aberrant expression of a miRNA in a cell, tissue, or animal. The methods may include contacting the cell, tissue, or animal with a pharmaceutical composition as detailed above. Aberrant expression includes up-regulation and down-regulation of the miRNA. In some embodiments, miRNA is up-regulated.

"Administration" or "administering," as used herein, refers to providing, contacting, and/or delivery of a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional or intracranial injection), transdermal, topical, buccal, rectal, vaginal, nasal, ophthalmic, via inhalation, and implants.

"Contacting," as used herein as in "contacting a cell," refers to contacting a cell directly or indirectly in vitro, ex vivo, or in vivo (i.e. within a subject, such as a mammal). Contacting a cell, which also includes "reacting" a cell, can occur as a result of administration to a subject. Contacting encompasses administration to a cell, tissue, mammal, subject, patient, or human. Further, contacting a cell includes adding an agent to a cell culture. Other suitable methods may include introducing or administering an agent to a cell, tissue, mammal, subject, or patient using appropriate procedures and routes of administration as defined herein.

As used herein, the term "treat" or "treating" a subject having a disorder refers to administering a regimen to the subject, such that at least one symptom of the disorder is cured, healed, alleviated, relieved, altered, remedied, ameliorated, or improved. Treating includes administering an amount effective to alleviate, relieve, alter, remedy, ameliorate, improve, or affect the disorder or the symptoms of the disorder. The treatment may inhibit deterioration or worsening of a symptom of a disorder.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including but not limited to") unless otherwise noted. All methods described herein can be performed in any suitable order unless otherwise indicated herein or otherwise clearly contradicted by context. The use of any and all examples, or exemplary language (e.g., "such as") provided herein, is intended merely to illustrate aspects and embodiments of the disclosure and does not limit the scope of the claims.

EXAMPLES

Example 1

Putamen miRNAs are Involved in the Pathogenesis of PD and are Novel Therapeutic Targets for Treatment of PD Among the differentially expressed miRNAs in the putamen, we identified 51 miRNAs that are dysregulated among ILBD, PD and PDD, and normal controls (Tables 3-9; FIG. 1); 59 miRNAs that are dysregulated in Stages 2, 3, and 4 of Lewy Body diseases when compared to normal controls (Tables 10-16; FIG. 2).

TABLE 3 miRNAs Differentially Expressed in Putamen among Different Diagnostic Groups (p < 0.05; at least 2 fold change) (51 in total)

| Diagnosis | Control | ILBD | PD | PDDnoAD |
|---|---|---|---|---|
| Control |  | 27 (11, 16) | 16 (7, 9) | 11 (3, 8) |
| ILBD | 27 (11, 16) |  | 14 (8, 6) | 18 (10, 8) |
| PD | 16 (7, 9) | 14 (8, 6) |  | 12 (6, 6) |
| PDDnoAD | 11 (3, 8) | 18 (10, 8) | 12 (6, 6) |  |

*Numbers in parentheses are numbers of (upregulated, downregulated) miRNAs.

TABLE 4 miRNAs differentially expressed in ILBD compared to normal controls (corrected p value < 0.05, fold change > 2 folds)

| miRNAs | p-value | Fold change (ILBD/Ctl) |
|---|---|---|
| hsa-miR-1224-3P-002752 | 0.007 | 10.69 |
| hsa-miR-767-5p-001993 | 0.008 | 5.31 |
| hsa-miR-431-4395173 | 0.009 | 4.25 |
| mmu-let-7d#-001178 | 0.013 | 3.46 |
| hsa-miR-183-4395380 | 0.000 | 3.37 |
| hsa-miR-873-4395467 | 0.015 | 2.68 |
| hsa-miR-33b-4395196 | 0.040 | 2.55 |
| hsa-miR-516b-4395172 | 0.015 | 2.53 |
| hsa-miR-127-5p-4395340 | 0.030 | 2.32 |
| hsa-miR-489-4395469 | 0.001 | 2.08 |
| hsa-miR-1270-002807 | 0.029 | 2.06 |
| hsa-miR-34b-000427 | 0.008 | 0.20 |
| hsa-miR-26a-2#-002115 | 0.002 | 0.22 |
| hsa-miR-638-001582 | 0.000 | 0.22 |
| hsa-miR-1290-002863 | 0.002 | 0.23 |
| hsa-miR-302d-000535 | 0.016 | 0.23 |
| hsa-miR-1248-002870 | 0.020 | 0.24 |
| hsa-miR-922-002152 | 0.024 | 0.26 |
| hsa-miR-30c-1#-002108 | 0.000 | 0.30 |
| hsa-miR-92a-1#-002137 | 0.002 | 0.31 |
| hsa-miR-497-001043 | 0.000 | 0.34 |

TABLE 4-continued miRNAs differentially expressed in ILBD compared to normal controls (corrected p value < 0.05, fold change > 2 folds)

| miRNAs | p-value | Fold change (ILBD/Ctl) |
|---|---|---|
| hsa-miR-1291-002838 | 0.005 | 0.36 |
| hsa-miR-1244-002791 | 0.009 | 0.40 |
| hsa-miR-635-001578 | 0.009 | 0.43 |
| hsa-miR-601-001558 | 0.009 | 0.44 |
| hsa-miR-1226#-002758 | 0.043 | 0.47 |
| hsa-miR-106b#-002380 | 0.002 | 0.47 |

TABLE 5 miRNAs differentially expressed in PD compared to normal controls (corrected p value < 0.05, fold change > 2 folds)

| miRNAs | p-value | Fold change (PD/Ctl) |
|---|---|---|
| hsa-miR-566-001533 | 0.01 | 15.96 |
| hsa-miR-767-5p-001993 | 0.01 | 7.39 |
| hsa-miR-1-4395333 | 0.01 | 2.94 |
| hsa-miR-33b-4395196 | 0.03 | 2.88 |
| hsa-miR-217-4395448 | 0.01 | 2.17 |
| hsa-miR-424-4373201 | 0.04 | 2.17 |
| hsa-miR-876-3p-4395336 | 0.02 | 2.12 |
| hsa-miR-516-3p-001149 | 0.05 | 0.11 |
| hsa-miR-644-001596 | 0.02 | 0.15 |
| dme-miR-7-000268 | 0.05 | 0.27 |
| hsa-miR-30c-1#-002108 | 0.01 | 0.38 |
| hsa-miR-720-002895 | 0.04 | 0.39 |
| hsa-miR-106b#-002380 | 0.00 | 0.42 |
| hsa-miR-551b#-002346 | 0.02 | 0.46 |
| hsa-miR-125b-2#-002158 | 0.02 | 0.48 |
| hsa-miR-1256-002850 | 0.01 | 0.48 |

TABLE 6 miRNAs differentially expressed in PDD compared to normal controls (corrected p value < 0.05, fold change > 2 folds)

| miRNAs | p-value | Fold change (PDD/Ctl) |
|---|---|---|
| hsa-miR-518a-3p-4395508 | 0.011 | 2.910 |
| hsa-miR-520g-4373257 | 0.045 | 2.891 |
| hsa-miR-337-3p-002157 | 0.015 | 2.851 |
| hsa-miR-516-3p-001149 | 0.042 | 0.090 |
| hsa-miR-644-001596 | 0.042 | 0.183 |
| hsa-miR-922-002152 | 0.013 | 0.286 |
| hsa-miR-193a-3p-4395361 | 0.017 | 0.300 |
| hsa-miR-92a-1#-002137 | 0.038 | 0.371 |
| hsa-miR-30c-1#-002108 | 0.004 | 0.373 |
| hsa-miR-1291-002838 | 0.017 | 0.415 |
| hsa-miR-15a-4373123 | 0.039 | 0.472 |

TABLE 7 miRNAs differentially expressed in PD compared to ILBD (corrected p value < 0.05, fold change > 2 folds)

| miRNAs | p-value | Fold change (PD/ILBD) |
|---|---|---|
| hsa-miR-302d-000535 | 0.004 | 6.208 |
| hsa-miR-23a-4373074 | 0.037 | 4.953 |
| hsa-miR-1290-002863 | 0.018 | 3.974 |
| hsa-miR-26a-2#-002115 | 0.025 | 3.090 |
| hsa-miR-638-001582 | 0.005 | 3.028 |
| hsa-miR-886-3p-4395305 | 0.049 | 2.740 |
| hsa-miR-548c-5p-4395540 | 0.040 | 2.241 |
| hsa-miR-92a-1#-002137 | 0.010 | 2.141 |
| hsa-miR-1224-3P-002752 | 0.049 | 0.273 |
| hsa-miR-122-4395356 | 0.019 | 0.308 |
| hsa-miR-302a-4378070 | 0.009 | 0.357 |

TABLE 7-continued miRNAs differentially expressed in PD compared to ILBD (corrected p value < 0.05, fold change > 2 folds)

| miRNAs | p-value | Fold change (PD/ILBD) |
|---|---|---|
| hsa-miR-424#-002309 | 0.032 | 0.380 |
| hsa-miR-486-5p-4378096 | 0.010 | 0.409 |
| hsa-miR-541-4395312 | 0.004 | 0.455 |

TABLE 8 miRNAs differentially expressed in PDD compared to ILBD (corrected p value < 0.05, fold change > 2 folds)

| miRNAs | p-value | fold change (PDD/ILBD) |
|---|---|---|
| hsa-miR-302d-000535 | 0.008 | 5.830 |
| hsa-miR-26a-2#-002115 | 0.002 | 4.415 |
| hsa-miR-630-001563 | 0.046 | 3.232 |
| hsa-miR-659-001514 | 0.030 | 3.229 |
| hsa-miR-641-001585 | 0.006 | 2.826 |
| hsa-miR-638-001582 | 0.011 | 2.586 |
| hsa-miR-125b-2#-002158 | 0.044 | 2.458 |
| hsa-miR-1255B-002801 | 0.010 | 2.387 |
| hsa-miR-337-3p-002157 | 0.048 | 2.190 |
| hsa-miR-380-5p-000570 | 0.009 | 2.058 |
| hsa-miR-202-4395474 | 0.005 | 0.260 |
| hsa-miR-873-4395467 | 0.001 | 0.279 |
| hsa-miR-767-5p-001993 | 0.040 | 0.298 |
| hsa-miR-431-4395173 | 0.010 | 0.317 |
| hsa-miR-1224-3P-002752 | 0.050 | 0.371 |
| hsa-miR-24-1#-002440 | 0.034 | 0.408 |
| hsa-miR-15a-4373123 | 0.002 | 0.455 |
| hsa-miR-339-5p-4395368 | 0.001 | 0.494 |

TABLE 9 miRNAs differentially expressed in PDD compared to PD (corrected p value < 0.05, fold change > 2 folds)

| miRNAs | p-value | Fold Change (PDD/PD) |
|---|---|---|
| dme-miR-7-000268 | 0.031 | 4.086 |
| hsa-miR-135b#-002159 | 0.049 | 2.608 |
| hsa-miR-641-001585 | 0.003 | 2.553 |
| hsa-miR-149#-002164 | 0.006 | 2.490 |
| hsa-miR-154#-000478 | 0.007 | 2.291 |
| hsa-miR-521-4373259 | 0.028 | 2.192 |
| hsa-miR-566-001533 | 0.035 | 0.115 |
| hsa-miR-767-5p-001993 | 0.025 | 0.214 |
| hsa-miR-202-4395474 | 0.008 | 0.321 |
| hsa-miR-548b-5p-4395519 | 0.025 | 0.356 |
| hsa-miR-217-4395448 | 0.011 | 0.414 |
| hsa-miR-326-4373050 | 0.042 | 0.463 |

TABLE 10 miRNAs Differentially Expressed in Putamen among Different Stage Groups by the Unified Staging System for LBD (p < 0.05; at least 2 fold change). (59 in total)

| Stages | 0 | 2 | 3 | 4 |
|---|---|---|---|---|
| 0 |  | 29 (9, 20) | 24 (11, 13) | 10 (3/7) |
| 2 | 29 (9, 20) |  | 9 (4, 5) | 13 (7, 6) |
| 3 | 24 (11, 13) | 9 (4, 5) |  | 7 (3, 4) |
| 4 | 10 (3/7) | 13 (7, 6) | 7 (3, 4) |  |

*Numbers in parentheses are numbers of (upregulated, downregulated) miRNAs.

TABLE 11 miRNAs differentially expressed in the putamen of Stage II compared to controls (corrected p value < 0.05, fold change > 2 folds)

| miRNAs | p-value | Fold change (Stage2/0) |
|---|---|---|
| hsa-miR-1224-3P-002752 | 0.016 | 8.494 |
| hsa-miR-767-5p-001993 | 0.027 | 5.601 |
| mmu-let-7d#-001178 | 0.008 | 3.631 |
| hsa-miR-33b-4395196 | 0.035 | 2.762 |
| hsa-miR-516b-4395172 | 0.033 | 2.435 |
| hsa-miR-183-4395380 | 0.006 | 2.427 |
| hsa-miR-1-4395333 | 0.031 | 2.393 |
| hsa-miR-127-5p-4395340 | 0.048 | 2.089 |
| hsa-miR-489-4395469 | 0.001 | 2.031 |
| hsa-miR-644-001596 | 0.015 | 0.157 |
| hsa-miR-1290-002863 | 0.003 | 0.250 |
| hsa-miR-1248-002870 | 0.015 | 0.254 |
| hsa-miR-638-001582 | 0.001 | 0.269 |
| hsa-miR-639-001583 | 0.017 | 0.274 |
| hsa-miR-1303-002792 | 0.025 | 0.284 |
| hsa-miR-30c-1#-002108 | 0.000 | 0.310 |
| hsa-miR-378-000567 | 0.041 | 0.318 |
| hsa-miR-26a-2#-002115 | 0.036 | 0.326 |
| hsa-miR-1291-002838 | 0.002 | 0.328 |
| hsa-miR-616-4395525 | 0.015 | 0.342 |
| hsa-miR-922-002152 | 0.028 | 0.346 |
| hsa-miR-1244-002791 | 0.000 | 0.358 |
| hsa-miR-548c-5p-4395540 | 0.037 | 0.366 |
| hsa-miR-92a-1#-002137 | 0.015 | 0.385 |
| hsa-miR-497-001043 | 0.000 | 0.392 |
| hsa-miR-601-001558 | 0.012 | 0.399 |
| hsa-miR-720-002895 | 0.046 | 0.430 |
| hsa-miR-1260-002896 | 0.004 | 0.452 |
| hsa-miR-635-001578 | 0.041 | 0.495 |

TABLE 12 miRNAs differentially expressed in the putamen of Stage III compared to controls (corrected p value < 0.05, fold change > 2 folds)

| miRNAs | p-value | Fold change (Stage 3/0) |
|---|---|---|
| hsa-miR-566-001533 | 0.037 | 13.485 |
| hsa-miR-1224-3P-002752 | 0.016 | 10.196 |
| hsa-miR-98-4373009 | 0.046 | 4.805 |
| hsa-miR-767-5p-001993 | 0.006 | 3.802 |
| hsa-miR-1-4395333 | 0.039 | 3.115 |
| hsa-miR-516b-4395172 | 0.018 | 2.728 |
| hsa-miR-33b-4395196 | 0.049 | 2.448 |
| hsa-miR-183-4395380 | 0.017 | 2.382 |
| hsa-miR-424-4373201 | 0.017 | 2.288 |
| hsa-miR-127-5p-4395340 | 0.033 | 2.144 |
| hsa-miR-1270-002807 | 0.049 | 2.080 |
| hsa-miR-34b-000427 | 0.031 | 0.231 |
| hsa-miR-922-002152 | 0.037 | 0.286 |
| hsa-miR-30c-1#-002108 | 0.001 | 0.323 |
| hsa-miR-106b#-002380 | 0.000 | 0.353 |
| hsa-miR-199a-5p-4373272 | 0.047 | 0.357 |
| hsa-miR-520D-3P-002743 | 0.005 | 0.370 |
| hsa-miR-100#-002142 | 0.000 | 0.400 |
| hsa-miR-638-001582 | 0.022 | 0.401 |
| hsa-miR-1226#-002758 | 0.023 | 0.408 |
| hsa-miR-92a-1#-002137 | 0.039 | 0.411 |
| hsa-miR-374b#-002391 | 0.005 | 0.436 |
| hsa-miR-497-001043 | 0.006 | 0.460 |
| hsa-miR-1260-002896 | 0.009 | 0.463 |

TABLE 13 miRNAs differentially expressed in the putamen of Stage IV compared to controls (corrected p value < 0.05, fold change > 2 folds)

| miRNAs | p-value | Fold change (Stage 4/0) |
|---|---|---|
| hsa-miR-518a-3p-4395508 | 0.027 | 2.605 |
| hsa-miR-1269-002789 | 0.043 | 2.424 |
| hsa-miR-876-3p-4395336 | 0.003 | 2.310 |
| hsa-miR-516-3p-001149 | 0.025 | 0.095 |
| hsa-miR-644-001596 | 0.038 | 0.192 |
| hsa-miR-639-001583 | 0.022 | 0.257 |
| hsa-miR-193a-3p-4395361 | 0.029 | 0.286 |
| hsa-miR-30c-1#-002108 | 0.016 | 0.412 |
| hsa-miR-635-001578 | 0.033 | 0.461 |
| hsa-miR-511-4373236 | 0.014 | 0.497 |

TABLE 14 miRNAs differentially expressed in the putamen of Stage III compared to Stage II (corrected p value < 0.05, fold change > 2 folds)

| miRNAs | p-value | Fold change (Stage 3/2) |
|---|---|---|
| hsa-miR-616-4395525 | 0.029 | 2.383 |
| hsa-miR-363#-001283 | 0.036 | 3.944 |
| hsa-miR-604-001567 | 0.046 | 2.567 |
| hsa-miR-639-001583 | 0.004 | 4.937 |
| hsa-miR-199a-5p-4373272 | 0.037 | 0.287 |
| hsa-let-7f-1#-002417 | 0.018 | 0.161 |
| hsa-miR-1201-002781 | 0.035 | 0.371 |
| hsa-miR-1301-002827 | 0.022 | 0.441 |
| hsa-miR-920-002150 | 0.040 | 0.372 |

TABLE 15 miRNAs differentially expressed in the putamen of Stage IV compared to Stage II (corrected p value < 0.05, fold change > 2 folds)

| miRNAs | p-value | Fold change (Stage 4/2) |
|---|---|---|
| hsa-miR-1290-002863 | 0.005 | 3.942 |
| hsa-miR-1248-002870 | 0.041 | 2.939 |
| hsa-miR-638-001582 | 0.005 | 2.776 |
| hsa-miR-1303-002792 | 0.036 | 2.440 |
| hsa-miR-296-3p-4395212 | 0.031 | 2.412 |
| hsa-miR-1255B-002801 | 0.004 | 2.314 |
| hsa-miR-378-000567 | 0.031 | 2.149 |
| hsa-let-7f-1#-002417 | 0.008 | 0.136 |
| hsa-miR-1224-3P-002752 | 0.014 | 0.210 |
| hsa-miR-571-001613 | 0.041 | 0.224 |
| mmu-let-7d#-001178 | 0.037 | 0.386 |
| hsa-miR-1227-002769 | 0.005 | 0.486 |
| hsa-miR-511-4373236 | 0.011 | 0.497 |

TABLE 16 miRNAs differentially expressed in the putamen of Stage IV compared to Stage III (corrected p value < 0.05, fold change > 2 folds)

| miRNAs | p-value | Fold change (Stage 4/3) |
|---|---|---|
| hsa-miR-211-4373088 | 0.029 | 50.755 |
| hsa-miR-876-3p-4395336 | 0.003 | 2.479 |
| hsa-miR-100#-002142 | 0.005 | 2.208 |
| hsa-miR-1224-3P-002752 | 0.008 | 0.175 |
| hsa-miR-639-001583 | 0.006 | 0.190 |
| hsa-miR-363#-001283 | 0.040 | 0.248 |
| hsa-miR-873-4395467 | 0.019 | 0.434 |

We also identified expressions of 29 miRNAs are correlated with the global Lewy-type asynucleinopathy (LTS) scores; 32 miRNAs are correlated with the degree of depigmentation of the neurons in Substantia Nigra; 33 miRNAs are correlated with the worsening of the motor functions, Unified PD Rating System (UPDRS) (Table 17-20).

TABLE 17

Disease-correlated miRNAs in the Putamen ($p < 0.05$)

|  | By LTS Score* | By SN depigmentation score | By UPDRS** |
|---|---|---|---|
| Positively correlated | 15 | 20 | 21 |
| Negatively correlated | 14 | 12 | 16 |

*LTS score: global Lewy-type α-synucleinopathy (LTS) scores.
**UPDRS: Unified PD Rating Scale.

TABLE 18 miRNAs whose expression levels are correlated with Lewy-type a-synucleinopathy (LTS) scores ($p \leq 0.05$)

| miRNAs | r |
|---|---|
| hsa-miR-132-4373143 | 0.505 |
| hsa-miR-212-4373087 | 0.453 |
| hsa-miR-383-4373018 | 0.449 |
| hsa-miR-885-5p-4395407 | 0.425 |
| hsa-miR-132#-002132 | 0.406 |
| hsa-miR-608-001571 | 0.401 |
| hsa-miR-183#-002270 | 0.391 |
| hsa-miR-587-001540 | 0.375 |
| hsa-miR-1269-002789 | 0.375 |
| hsa-miR-629-001562 | 0.370 |
| hsa-let-7c-4373167 | 0.350 |
| hsa-miR-559-001527 | 0.349 |
| hsa-miR-129-3p-4373297 | 0.345 |
| hsa-miR-130b#-002114 | 0.344 |
| hsa-miR-125a-5p-4395309 | 0.322 |
| hsa-miR-574-3p-4395460 | −0.317 |
| hsa-miR-374a-4373028 | −0.320 |
| hsa-miR-720-002895 | −0.322 |
| hsa-miR-1275-002840 | −0.323 |
| hsa-miR-142-5p-4395359 | −0.330 |
| hsa-miR-124-4373295 | −0.330 |
| hsa-miR-26b#-002444 | −0.331 |
| hsa-miR-1226#-002758 | −0.350 |
| hsa-miR-374b#-002391 | −0.350 |
| hsa-miR-193a-3p-4395361 | −0.364 |
| hsa-miR-590-5p-4395176 | −0.379 |
| hsa-miR-660-4380925 | −0.388 |
| hsa-miR-339-5p-4395368 | −0.458 |
| hsa-miR-106b#-002380 | −0.473 |

TABLE 19 miRNAs whose expression levels are correlated with SN depigmentation scores ($p \leq 0.05$)

| miRNAs | r |
|---|---|
| hsa-miR-132-4373143 | 0.548 |
| hsa-miR-212-4373087 | 0.444 |
| hsa-miR-1269-002789 | 0.410 |
| hsa-miR-455-5p-4378098 | 0.377 |
| hsa-miR-500-4395539 | 0.376 |
| hsa-miR-139-3p-4395424 | 0.371 |
| hsa-miR-183#-002270 | 0.366 |
| hsa-miR-518b-4373246 | 0.361 |
| hsa-miR-455-3p-4395355 | 0.348 |
| hsa-miR-629-001562 | 0.341 |
| hsa-miR-132#-002132 | 0.340 |
| hsa-miR-23a-4373074 | 0.337 |
| hsa-miR-335-4373045 | 0.320 |

TABLE 19-continued miRNAs whose expression levels are correlated with SN depigmentation scores (p < 0.05)

| miRNAs | r |
|---|---|
| hsa-miR-580-001621 | 0.315 |
| hsa-miR-383-4373018 | 0.312 |
| hsa-miR-608-001571 | 0.312 |
| hsa-miR-548l-002909 | 0.311 |
| hsa-miR-505#-002087 | 0.299 |
| hsa-let-7c-4373167 | 0.297 |
| hsa-miR-129-3p-4373297 | 0.291 |
| hsa-miR-17-4395419 | −0.314 |
| hsa-miR-503-4373228 | −0.315 |
| hsa-miR-193a-3p-435361 | −0.322 |
| hsa-miR-339-5p-4395368 | −0.327 |
| hsa-miR-140-5p-4373374 | −0.327 |
| hsa-miR-574-3p-4395460 | −0.347 |
| hsa-miR-302a-4378070 | −0.361 |
| hsa-miR-10b#-002315 | −0.366 |
| hsa-miR-93-4373302 | −0.374 |
| hsa-miR-590-5p-4395176 | −0.419 |
| hsa-miR-106b#-002380 | −0.461 |
| hsa-miR-124-4373295 | −0.500 |

TABLE 20 miRNAs whose expression levels are correlated with UPDRS (p < 0.05)

| miRNAs | r |
|---|---|
| hsa-miR-198-4395384 | 0.582 |
| hsa-miR-886-3p-4395305 | 0.528 |
| hsa-miR-450a-4395414 | 0.525 |
| hsa-miR-593-001547 | 0.523 |
| hsa-miR-920-002150 | 0.518 |
| hsa-miR-521-4373259 | 0.507 |
| hsa-miR-629-4395547 | 0.501 |
| hsa-miR-517#-001113 | 0.469 |
| hsa-miR-520c-3p-002400 | 0.461 |
| hsa-miR-125b-2#-002158 | 0.461 |
| hsa-miR-27a#-002445 | 0.456 |
| hsa-miR-559-001527 | 0.447 |
| hsa-miR-589-001543 | 0.442 |
| hsa-miR-886-5p-4395304 | 0.430 |
| hsa-miR-1282-002803 | 0.430 |
| hsa-miR-1270-002807 | 0.423 |
| hsa-miR-99a#-002141 | 0.422 |
| hsa-miR-181a-2#-002317 | 0.422 |
| hsa-miR-608-001571 | 0.380 |
| hsa-miR-211-4373088 | 0.378 |
| hsa-miR-500-001046 | 0.376 |
| hsa-miR-758-4395180 | −0.408 |
| hsa-miR-144-002676 | −0.415 |
| hsa-miR-138-4395395 | −0.415 |
| hsa-miR-92a-1#-002137 | −0.422 |
| hsa-miR-411-4381013 | −0.425 |
| hsa-miR-448-4373206 | −0.427 |
| hsa-miR-324-5p-4373052 | −0.432 |
| hsa-miR-203-4373095 | −0.439 |
| hsa-miR-107-4373154 | −0.440 |
| hsa-miR-488-4395468 | −0.462 |
| hsa-miR-137-4373301 | −0.469 |
| hsa-miR-148a-4373130 | −0.475 |
| hsa-miR-296-5p-4373066 | −0.477 |
| hsa-miR-218-4373081 | −0.479 |
| hsa-miR-153-4373305 | −0.507 |
| hsa-miR-552-001520 | −0.521 |

These miRNAs may be involved in the pathological changes in the putamen, contributing to the pathogenesis of Lewy body diseases, including PD; and therefore, they may be new therapeutic targets for treatment of PD at different stages of the diseases.

Example 2

CSF miRNAs as Diagnostic Biomarkers for Presymptomatic and Early PD, and Cognitive Impairment in PD Among the differentially expressed miRNAs in the CSF, we identified 80 miRNAs that are differentially expressed in ILBD, PD and PDD, when compared to normal controls (Tables 21-27; FIG. 3); and 87 miRNAs that are differentially expression in Stages 2, 3, and 4 of Lewy Body diseases when compared to normal controls (Table 28-34; FIG. 4).

TABLE 21 miRNAs Differentially Expressed in CSF Among Different Diagnostic Groups (p < 0.05; at least 2 fold change). (80 in total)

| Diagnosis | Control | ILBD | PD | PDDnoAD |
|---|---|---|---|---|
| Control |  | 35 (25, 10) | 27 (15, 12) | 15 (13, 2) |
| ILBD | 35 (25, 10) |  | 11 (5, 6) | 14 (8, 6) |
| PD | 27 (15, 12) | 11 (5, 6) |  | 20 (8, 12) |
| PDDnoAD | 15 (13, 2) | 14 (8, 6) | 20 (8, 12) |  |

*Numbers in parentheses are numbers of (upregulated, downregulated) miRNAs.

TABLE 22

CSF miRNAs differentially expressed in ILBD compared to control (corrected p value < 0.05, fold change > 2 folds)

| miRNAs | p-value | Fold Change (ILBD/ctl) |
|---|---|---|
| hsa-miR-497-001043 | 0.008 | 5.645 |
| hsa-miR-126#-000451 | 0.026 | 5.413 |
| hsa-miR-9#-002231 | 0.005 | 5.231 |
| hsa-miR-1300-002902 | 0.023 | 5.129 |
| hsa-miR-143-4395360 | 0.007 | 4.804 |
| hsa-miR-374b-4381045 | 0.027 | 4.747 |
| hsa-miR-660-4380925 | 0.005 | 4.465 |
| hsa-miR-432-001026 | 0.046 | 4.313 |
| hsa-miR-31#-002113 | 0.012 | 3.647 |
| hsa-miR-324-5p-4373052 | 0.007 | 3.367 |
| hsa-miR-99a#-002141 | 0.024 | 3.323 |
| hsa-miR-628-3p-002434 | 0.002 | 3.318 |
| hsa-miR-652-4395463 | 0.035 | 3.011 |
| hsa-miR-1271-002779 | 0.039 | 2.775 |
| hsa-miR-26b#-002444 | 0.016 | 2.706 |
| hsa-miR-195-4373105 | 0.000 | 2.680 |
| hsa-miR-340-4395369 | 0.031 | 2.568 |
| hsa-miR-213-000516 | 0.032 | 2.524 |
| hsa-miR-29a-4395223 | 0.003 | 2.483 |
| hsa-miR-449b-4381011 | 0.045 | 2.348 |
| hsa-miR-708-4395452 | 0.021 | 2.292 |
| hsa-miR-29c-4395171 | 0.006 | 2.248 |
| hsa-miR-218-4373081 | 0.016 | 2.223 |
| hsa-miR-488-001106 | 0.014 | 2.155 |
| hsa-miR-30e-3p-000422 | 0.035 | 2.154 |
| hsa-miR-516-3p-001149 | 0.040 | 0.068 |
| hsa-miR-296-5p-4373066 | 0.048 | 0.252 |
| hsa-miR-671-3p-4395433 | 0.021 | 0.274 |
| hsa-miR-145-4395389 | 0.016 | 0.289 |
| hsa-miR-597-4380960 | 0.012 | 0.309 |
| hsa-miR-328-4373049 | 0.025 | 0.362 |
| hsa-miR-197-4373102 | 0.039 | 0.382 |
| hsa-miR-92a-4395169 | 0.019 | 0.405 |
| hsa-miR-484-4381032 | 0.023 | 0.432 |
| hsa-miR-700-002895 | 0.044 | 0.449 |

TABLE 23

CSF miRNAs differentially expressed in PD compared to control (corrected p value < 0.05, fold change > 2 folds)

| miRNAs | p-value | Fold Change (PD/ctl) |
|---|---|---|
| hsa-miR-664-002897 | 0.001 | 18.334 |
| hsa-miR-590-3P-002677 | 0.000 | 5.568 |
| hsa-miR-577-002675 | 0.033 | 4.923 |
| hsa-miR-374b-4381045 | 0.032 | 4.850 |
| hsa-miR-9#-002231 | 0.006 | 4.755 |
| hsa-miR-213-000516 | 0.001 | 4.217 |
| rno-miR-7#-001338 | 0.044 | 3.712 |
| hsa-miR-340#-002259 | 0.033 | 3.561 |
| hsa-miR-497-001043 | 0.050 | 3.504 |
| hsa-miR-454-4395434 | 0.013 | 3.093 |
| hsa-miR-99a#-002141 | 0.049 | 3.050 |
| hsa-miR-191#-002678 | 0.005 | 2.907 |
| hsa-miR-1183-002841 | 0.038 | 2.387 |
| hsa-miR-29a#-002447 | 0.030 | 2.243 |
| hsa-miR-148b#-002160 | 0.014 | 2.137 |
| hsa-miR-142-3p-4373136 | 0.029 | 0.260 |
| hsa-miR-519a-4395526 | 0.016 | 0.318 |
| hsa-miR-511-4373236 | 0.043 | 0.319 |
| hsa-miR-486-5p-4378096 | 0.012 | 0.428 |
| hsa-miR-92a-4395169 | 0.046 | 0.435 |
| hsa-miR-381-4373020 | 0.037 | 0.435 |
| hsa-miR-545-4395378 | 0.010 | 0.439 |
| hsa-miR-196b-4395326 | 0.007 | 0.458 |
| hsa-miR-10b-4395329 | 0.007 | 0.463 |
| hsa-miR-98-4373009 | 0.006 | 0.465 |
| hsa-miR-18a-4395533 | 0.003 | 0.470 |
| hsa-miR-654-3p-4395350 | 0.008 | 0.473 |

TABLE 24

CSF miRNAs differentially expressed in PDDnoAD compared to control (corrected p value < 0.05, fold change > 2 folds)

| miRNAs | p-value | Fold Change (PDDnoAD/ctl) |
|---|---|---|
| hsa-miR-1300-002902 | 0.001 | 10.044 |
| hsa-miR-664-002897 | 0.040 | 6.381 |
| hsa-miR-374b-4381045 | 0.011 | 5.426 |
| hsa-miR-1298-002861 | 0.033 | 4.569 |
| hsa-miR-135b-4395372 | 0.003 | 3.592 |
| hsa-miR-363-4378090 | 0.002 | 3.357 |
| hsa-miR-660-4380925 | 0.032 | 3.189 |
| hsa-miR-9#-002231 | 0.029 | 2.793 |
| hsa-miR-362-5p-4378092 | 0.033 | 2.287 |
| hsa-miR-29a-4395223 | 0.005 | 2.209 |
| hsa-miR-1264-002799 | 0.028 | 2.090 |
| hsa-miR-29a#-002447 | 0.049 | 2.073 |
| hsa-miR-29c-4395171 | 0.003 | 2.043 |
| hsa-miR-146b-5p-4373178 | 0.010 | 0.430 |
| hsa-miR-518a-3p-4395508 | 0.020 | 0.372 |

TABLE 25

CSF miRNAs differentially expressed in PD compared to ILBD (corrected p value < 0.05, fold change > 2 folds)

| miRNAs | p-value | Fold Change (PD/ILBD) |
|---|---|---|
| hsa-miR-664-002897 | 0.028 | 4.750 |
| hsa-miR-720-002895 | 0.006 | 3.384 |
| hsa-miR-590-3P-002677 | 0.028 | 2.431 |
| hsa-miR-625#-002432 | 0.033 | 2.096 |
| hsa-miR-1183-002841 | 0.032 | 2.087 |
| hsa-miR-143-4395360 | 0.026 | 0.315 |
| hsa-miR-519a-4395526 | 0.005 | 0.334 |
| hsa-miR-130a-4373145 | 0.025 | 0.414 |
| hsa-miR-130b-4373144 | 0.037 | 0.422 |
| hsa-miR-500-4395539 | 0.041 | 0.424 |
| hsa-miR-145#-002149 | 0.036 | 0.426 |

TABLE 26

CSF miRNAs differentially expressed in PDDnoAD compared to ILBD (corrected p value < 0.05, fold change > 2 folds)

| miRNAs | p-value | Fold Change (PDDnoAD/ILBD) |
|---|---|---|
| hsa-miR-886-5p-4395304 | 0.024 | 4.734 |
| hsa-miR-886-3p-4395305 | 0.022 | 4.189 |
| hsa-miR-125a-3p-4395310 | 0.011 | 2.761 |
| hsa-miR-222#-002097 | 0.040 | 2.635 |
| hsa-miR-362-5p-4378092 | 0.006 | 2.392 |
| hsa-miR-105-4395278 | 0.048 | 2.358 |
| hsa-miR-363-4378090 | 0.036 | 2.203 |
| hsa-let-7d-4395394 | 0.032 | 2.128 |
| hsa-miR-143-4395360 | 0.011 | 0.329 |
| hsa-miR-543-002376 | 0.034 | 0.430 |
| hsa-miR-628-3p-002434 | 0.029 | 0.441 |
| hsa-miR-26b#-002444 | 0.011 | 0.460 |
| hsa-miR-146b-5p-4373178 | 0.035 | 0.494 |
| hsa-miR-376c-4395233 | 0.035 | 0.497 |

TABLE 27

CSF miRNAs differentially expressed in PDDnoAD compared to PD (corrected p value < 0.05, fold change > 2 folds)

| miRNAs | p-value | Fold Change (PDDnoAD/PD) |
|---|---|---|
| hsa-miR-148b-4373129 | 0.005 | 4.709 |
| hsa-miR-886-5p-4395304 | 0.013 | 3.754 |
| hsa-miR-500-4395539 | 0.006 | 3.002 |
| hsa-miR-886-3p-4395305 | 0.032 | 2.889 |
| hsa-miR-519a-4395526 | 0.045 | 2.654 |
| hsa-miR-511-4373236 | 0.035 | 2.279 |
| hsa-miR-363-4378090 | 0.037 | 2.114 |
| hsa-miR-99b-4373007 | 0.010 | 2.038 |
| dme-miR-7-000268 | 0.015 | 0.118 |
| hsa-miR-1233-002768 | 0.027 | 0.229 |
| hsa-miR-409-3p-002332 | 0.034 | 0.248 |
| hsa-miR-206-000510 | 0.027 | 0.263 |
| hsa-miR-590-3P-002677 | 0.001 | 0.275 |
| hsa-miR-213-000516 | 0.006 | 0.316 |
| hsa-miR-629-001562 | 0.041 | 0.357 |
| hsa-miR-539-4378103 | 0.037 | 0.385 |
| hsa-miR-543-002376 | 0.004 | 0.407 |
| hsa-miR-720-002895 | 0.014 | 0.438 |
| hsa-miR-146b-5p-4373178 | 0.022 | 0.453 |
| hsa-miR-136#-002100 | 0.013 | 0.465 |

TABLE 28 miRNAs Differentially Expressed in CSF Among Different Stages by the Unified Staging System for LBD (p < 0.05; at least 2 fold change) (87 in total).

| Stages | 0 | 2 | 3 | 4 |
|---|---|---|---|---|
| 0 | | 22 (18, 4) | 70 (46, 24) | 9 (5, 4) |
| 2 | 22 (18, 4) | | 20 (15, 5) | 2 (0, 2) |
| 3 | 70 (46, 24) | 20 (15, 5) | | 29 (7, 22) |
| 4 | 9 (5, 4) | 2 (0, 2) | 29 (7, 22) | |

*Numbers in parentheses: numbers of (upregulated, downregulated) miRNAs.

TABLE 29

CSF miRNAs differentially expressed in Stage II compared to controls (corrected p values < 0.05, fold change > 2 folds)

| miRNAs | p-value | Fold change (Stage 2/0) |
|---|---|---|
| hsa-miR-664-002897 | 0.035 | 7.145 |
| hsa-miR-126#-000451 | 0.041 | 6.557 |
| hsa-miR-374b-4381045 | 0.023 | 5.102 |
| hsa-miR-31-4395390 | 0.007 | 4.549 |
| hsa-miR-1300-002902 | 0.032 | 3.927 |
| hsa-miR-577-002675 | 0.032 | 3.690 |
| hsa-miR-9#-002231 | 0.006 | 3.655 |
| hsa-miR-497-001043 | 0.047 | 3.493 |
| hsa-miR-660-4380925 | 0.025 | 3.394 |
| hsa-miR-652-4395463 | 0.018 | 3.212 |
| hsa-miR-31#-002113 | 0.032 | 2.830 |
| hsa-miR-340-4395369 | 0.037 | 2.768 |
| hsa-miR-200b-4395362 | 0.034 | 2.719 |
| hsa-miR-26b#-002444 | 0.034 | 2.437 |
| hsa-miR-135b-4395372 | 0.049 | 2.391 |
| hsa-miR-195-4373105 | 0.003 | 2.243 |
| hsa-miR-628-3p-002434 | 0.027 | 2.081 |
| hsa-miR-29a#-002447 | 0.048 | 2.002 |
| hsa-miR-671-3p-4395433 | 0.023 | 0.282 |
| hsa-miR-142-3p-4373136 | 0.038 | 0.348 |
| hsa-miR-145-4395389 | 0.043 | 0.407 |
| hsa-miR-597-4380960 | 0.047 | 0.408 |

TABLE 30

CSF miRNAs differentially expressed in Stage III compared to controls (corrected p value < 0.05, fold change > 2 folds)

| miRNAs | p-value | Fold change (Stage 3/0) |
|---|---|---|
| hsa-miR-661-001606 | 0.008 | 35.493 |
| hsa-miR-1300-002902 | 0.002 | 14.271 |
| hsa-miR-497-001043 | 0.000 | 10.198 |
| hsa-miR-664-002897 | 0.023 | 7.823 |
| hsa-miR-577-002675 | 0.013 | 7.754 |
| hsa-miR-9#-002231 | 0.003 | 7.611 |
| hsa-miR-769-5p-001998 | 0.020 | 6.804 |
| hsa-miR-374b-4381045 | 0.014 | 5.960 |
| hsa-miR-31#-002113 | 0.004 | 5.909 |
| hsa-miR-99a#-002141 | 0.002 | 5.850 |
| hsa-miR-638-001582 | 0.014 | 5.810 |
| hsa-miR-660-4380925 | 0.005 | 5.749 |
| hsa-miR-1298-002861 | 0.037 | 5.389 |
| hsa-miR-592-001546 | 0.018 | 4.821 |
| rno-miR-29c#-001818 | 0.011 | 4.648 |
| hsa-miR-324-5p-4373052 | 0.001 | 4.592 |
| hsa-miR-590-3P-002677 | 0.001 | 4.436 |
| hsa-miR-213-000516 | 0.004 | 4.032 |
| hsa-miR-1271-002779 | 0.005 | 3.965 |
| hsa-miR-9-4373285 | 0.034 | 3.796 |
| hsa-miR-622-001553 | 0.017 | 3.549 |
| hsa-miR-340#-002259 | 0.037 | 3.533 |
| hsa-miR-151-5P-002642 | 0.035 | 3.373 |
| hsa-miR-628-3p-002434 | 0.006 | 3.265 |
| hsa-miR-29a-4395223 | 0.001 | 3.218 |
| hsa-miR-143-4395360 | 0.046 | 3.190 |
| hsa-miR-135b-4395372 | 0.013 | 3.045 |
| hsa-miR-652-4395463 | 0.031 | 2.942 |
| hsa-miR-129-3p-4373297 | 0.045 | 2.926 |
| hsa-miR-218-4373081 | 0.004 | 2.880 |
| hsa-miR-454-4395434 | 0.034 | 2.870 |
| hsa-miR-340-4395369 | 0.028 | 2.834 |
| hsa-miR-29c-4395171 | 0.001 | 2.802 |
| hsa-miR-1226#-002758 | 0.030 | 2.670 |
| hsa-miR-30a-3p-000416 | 0.012 | 2.617 |
| hsa-miR-639-001583 | 0.042 | 2.574 |
| hsa-miR-195-4373105 | 0.000 | 2.533 |
| hsa-miR-191#-002678 | 0.007 | 2.389 |
| hsa-miR-29a#-002447 | 0.030 | 2.254 |
| hsa-miR-148b#-002160 | 0.020 | 2.173 |
| hsa-miR-192-4373108 | 0.028 | 2.137 |
| hsa-miR-148a-4373130 | 0.003 | 2.135 |
| hsa-miR-548l-002909 | 0.036 | 2.055 |
| hsa-miR-1264-002799 | 0.004 | 2.052 |
| hsa-miR-19b-4373098 | 0.014 | 2.013 |
| hsa-miR-27a#-002445 | 0.021 | 2.007 |
| hsa-miR-483-3p-002339 | 0.005 | 0.081 |
| hsa-miR-1260-002896 | 0.026 | 0.122 |
| hsa-miR-296-5p-4373066 | 0.019 | 0.140 |
| hsa-miR-145-4395389 | 0.001 | 0.161 |
| hsa-miR-671-3p-4395433 | 0.009 | 0.166 |
| hsa-miR-125a-5p-4395309 | 0.011 | 0.243 |
| hsa-miR-197-4373102 | 0.005 | 0.257 |
| hsa-miR-92a-4395169 | 0.002 | 0.284 |
| hsa-miR-597-4380960 | 0.022 | 0.292 |
| hsa-miR-328-4373049 | 0.001 | 0.305 |
| hsa-miR-484-4381032 | 0.002 | 0.319 |
| hsa-miR-125b-4373148 | 0.009 | 0.363 |
| hsa-miR-345-4395297 | 0.019 | 0.413 |
| hsa-miR-10b-4395329 | 0.008 | 0.461 |
| hsa-miR-365-4373194 | 0.039 | 0.463 |
| hsa-miR-98-4373009 | 0.008 | 0.464 |
| hsa-miR-545-4395378 | 0.020 | 0.468 |
| hsa-miR-28-3p-4395557 | 0.000 | 0.469 |
| hsa-miR-25-4373071 | 0.006 | 0.472 |
| hsa-miR-654-3p-4395350 | 0.009 | 0.474 |
| hsa-miR-486-5p-4378096 | 0.033 | 0.475 |
| hsa-miR-196b-4395326 | 0.014 | 0.482 |
| hsa-miR-193a-5p-4395392 | 0.050 | 0.486 |
| hsa-miR-199a-5p-4373272 | 0.040 | 0.497 |

TABLE 31

CSF miRNAs differentially expressed in Stage IV compared to controls (corrected p value < 0.05, fold change > 2 folds)

| miRNAs | p-value | Fold change (Stage 4/0) |
|---|---|---|
| hsa-miR-664-002897 | 0.0267 | 6.6111 |
| hsa-miR-374b-4381045 | 0.0298 | 4.2124 |
| hsa-miR-1300-002902 | 0.0443 | 3.9213 |
| hsa-miR-9#-002231 | 0.0246 | 2.8799 |
| hsa-miR-191#-002678 | 0.0377 | 2.2135 |
| hsa-miR-142-3p-4373136 | 0.0103 | 0.2291 |
| hsa-miR-197-4373102 | 0.0326 | 0.4014 |
| hsa-miR-518a-3p-4395508 | 0.0247 | 0.4188 |
| hsa-miR-320B-002844 | 0.0210 | 0.4882 |

TABLE 32

CSF miRNAs differentially expressed in Stage III compared to Stage II (corrected p value < 0.05, fold change > 2 folds)

| miRNAs | p-value | Fold change (Stage 3/2) |
|---|---|---|
| hsa-miR-661-001606 | 0.014 | 10.926 |
| hsa-miR-638-001582 | 0.018 | 4.388 |
| hsa-miR-144#-002148 | 0.002 | 4.147 |
| hsa-miR-566-001533 | 0.010 | 3.230 |
| hsa-miR-622-001553 | 0.022 | 3.205 |
| hsa-miR-497-001043 | 0.031 | 2.919 |
| hsa-miR-663B-002857 | 0.024 | 2.748 |
| hsa-miR-1226#-002758 | 0.023 | 2.555 |
| hsa-miR-30a-3p-000416 | 0.002 | 2.417 |
| hsa-miR-324-5p-4373052 | 0.040 | 2.290 |
| hsa-miR-590-3P-002677 | 0.042 | 2.244 |
| rno-miR-29c#-001818 | 0.044 | 2.193 |
| hsa-miR-148a-4373130 | 0.015 | 2.140 |
| hsa-miR-31#-002113 | 0.023 | 2.088 |

TABLE 32-continued

CSF miRNAs differentially expressed in Stage III compared to Stage II (corrected p value < 0.05, fold change > 2 folds)

| miRNAs | p-value | Fold change (Stage 3/2) |
|---|---|---|
| hsa-miR-218-4373081 | 0.029 | 2.077 |
| hsa-miR-483-3p-002339 | 0.011 | 0.142 |
| hsa-miR-125b-4373148 | 0.001 | 0.251 |
| hsa-miR-125a-5p-4395309 | 0.013 | 0.272 |
| hsa-miR-145-4395389 | 0.015 | 0.395 |
| hsa-miR-130b-4373144 | 0.047 | 0.448 |

TABLE 33

CSF miRNAs differentially expressed in Stage IV compared to Stage II (corrected p value < 0.05, fold change > 2 folds)

| miRNAs | p-value | Fold change (Stage 4/2) |
|---|---|---|
| hsa-miR-181a-4373117 | 0.022 | 0.436 |
| hsa-miR-338-3p-4395363 | 0.049 | 0.459 |

TABLE 34

CSF miRNAs differentially expressed in Stage IV compared to Stage III (corrected p value < 0.05, fold change > 2 folds)

| miRNAs | p-value | Fold change (Stage 4/3) |
|---|---|---|
| hsa-miR-483-3p-002339 | 0.041 | 5.103 |
| hsa-miR-145-4395389 | 0.001 | 4.830 |
| hsa-miR-296-5p-4373066 | 0.033 | 4.172 |
| hsa-miR-125a-5p-4395309 | 0.010 | 3.893 |
| hsa-miR-671-3p-4395433 | 0.022 | 3.134 |
| hsa-miR-125b-4373148 | 0.001 | 2.949 |
| hsa-miR-484-4381032 | 0.014 | 2.231 |
| hsa-miR-661-001606 | 0.010 | 0.142 |
| hsa-miR-497-001043 | 0.007 | 0.216 |
| hsa-miR-1291-002838 | 0.004 | 0.240 |
| hsa-miR-638-001582 | 0.013 | 0.244 |
| hsa-miR-31#-002113 | 0.004 | 0.245 |
| hsa-miR-378-002243 | 0.013 | 0.267 |
| hsa-miR-1271-002779 | 0.002 | 0.267 |
| hsa-miR-219-2-3p-4395501 | 0.033 | 0.272 |
| hsa-miR-622-001553 | 0.010 | 0.289 |
| hsa-miR-99a#-002141 | 0.007 | 0.294 |
| hsa-miR-144#-002148 | 0.024 | 0.324 |
| hsa-miR-769-5p-001998 | 0.037 | 0.325 |
| hsa-miR-6638-002857 | 0.025 | 0.361 |
| hsa-miR-1226#-002758 | 0.011 | 0.363 |
| hsa-miR-142-3p-4373136 | 0.033 | 0.379 |
| hsa-miR-151-5P-002642 | 0.001 | 0.382 |
| hsa-miR-3208-002844 | 0.000 | 0.413 |
| hsa-miR-12558-002801 | 0.044 | 0.417 |
| hsa-miR-660-4380925 | 0.006 | 0.439 |
| hsa-miR-192-4373108 | 0.045 | 0.479 |
| hsa-miR-218-4373081 | 0.026 | 0.485 |
| hsa-miR-30a-3p-000416 | 0.026 | 0.493 |

We also identified expressions of 26 miRNAs are correlated with the global Lewy-type asynucleinopathy (LTS) scores; 36 miRNAs are correlated with the degree of depigmentation of the neurons in Substantia Nigra; 40 miRNAs are correlated with the worsening of the motor functions, Unified PD Rating System (UPDRS) (Tables 35-38).

TABLE 35

Disease-correlated miRNAs in CSF ($p < 0.05$)

| | By LTS Score* | By SN depigmentation score | By UPDRS** |
|---|---|---|---|
| Positively correlated | 23 | 19 | 9 |
| Negatively correlated | 3 | 17 | 31 |

*LTS score: global Lewy-type α-synucleinopathy (LTS) scores.
**UPDRS: Unified PD Rating Scale.

TABLE 36

CSF miRNAs whose expression levels are correlated with Lewy-type a-synucleinopathy (LTS) scores ($p < 0.05$)

| miRNAs | r |
|---|---|
| hsa-miR-664-002897 | 0.519 |
| hsa-miR-148b#-002160 | 0.496 |
| hsa-miR-29a#-002447 | 0.453 |
| hsa-miR-592-001546 | 0.403 |
| hsa-miR-363-4378090 | 0.400 |
| hsa-miR-135b-4395372 | 0.397 |
| hsa-miR-135a-4373140 | 0.390 |
| hsa-miR-1298-002861 | 0.389 |
| hsa-miR-34a#-002316 | 0.389 |
| hsa-miR-374b-4381045 | 0.384 |
| rno-miR-7#-001338 | 0.381 |
| hsa-miR-590-3P-002677 | 0.379 |
| rno-miR-29c#-001818 | 0.371 |
| hsa-miR-1264-002799 | 0.371 |
| hsa-miR-22#-002301 | 0.358 |
| hsa-miR-30a-3p-000416 | 0.353 |
| hsa-miR-650-001603 | 0.346 |
| hsa-miR-340-4395369 | 0.338 |
| hsa-miR-454-4395434 | 0.336 |
| hsa-miR-767-3p-001995 | 0.333 |
| hsa-miR-101#-002143 | 0.329 |
| hsa-miR-190-4373110 | 0.328 |
| hsa-miR-213-000516 | 0.320 |
| hsa-miR-486-5p-4378096 | −0.373 |
| hsa-miR-196b-4395326 | −0.435 |
| hsa-miR-518a-3p-4395508 | −0.439 |

TABLE 37

CSF miRNAs whose expression levels are correlated with SN depigmentation scores ($p < 0.05$)

| miRNAs | r |
|---|---|
| hsa-miR-363-4378090 | 0.443 |
| hsa-miR-374b-4381045 | 0.395 |
| hsa-miR-184-4373113 | 0.339 |
| hsa-miR-135b-4395372 | 0.325 |
| hsa-miR-628-5p-4395544 | 0.323 |
| hsa-miR-374a-4373028 | 0.309 |
| hsa-miR-331-3p-4373046 | 0.294 |
| hsa-miR-217-4395448 | 0.289 |
| hsa-miR-590-5p-4395176 | 0.286 |
| hsa-miR-664-002897 | 0.285 |
| hsa-let-7a-4373169 | 0.279 |
| hsa-miR-26b-4395167 | 0.272 |
| hsa-let-7f-4373164 | 0.263 |
| hsa-miR-362-5p-4378092 | 0.263 |
| hsa-miR-455-3p-4395355 | 0.262 |
| hsa-miR-449b-4381011 | 0.262 |
| hsa-miR-99a-4373008 | 0.255 |
| hsa-miR-135a-4373140 | 0.254 |
| hsa-miR-26a-4395166 | 0.253 |
| hsa-miR-218-2#-002294 | −0.227 |
| hsa-miR-139-3p-4395424 | −0.232 |
| hsa-miR-143#-002146 | −0.246 |
| hsa-miR-185-4395382 | −0.249 |
| hsa-miR-630-001563 | −0.255 |

TABLE 37-continued

CSF miRNAs whose expression levels are correlated with SN depigmentation scores (p < 0.05)

| miRNAs | r |
|---|---|
| hsa-miR-519a-4395526 | −0.255 |
| hsa-miR-376a#-002127 | −0.260 |
| hsa-let-7c-4373167 | −0.263 |
| hsa-miR-133b-4395358 | −0.271 |
| hsa-miR-145#-002149 | −0.282 |
| hsa-miR-181a-4373117 | −0.299 |
| hsa-miR-182#-000483 | −0.308 |
| hsa-miR-200a#-001011 | −0.313 |
| hsa-miR-197-4373102 | −0.315 |
| hsa-miR-146a#-002163 | −0.318 |
| hsa-miR-142-3p-4373136 | −0.354 |
| hsa-miR-518a-3p-4395508 | −0.363 |

TABLE 38

CSF miRNAs whose expression levels are correlated with UPDRS (p < 0.05)

| miRNAs | r |
|---|---|
| hsa-miR-101#-002143 | 0.572 |
| hsa-miR-222#-002097 | 0.565 |
| hsa-miR-626-001559 | 0.555 |
| hsa-miR-29a#-002447 | 0.503 |
| hsa-miR-1238-002927 | 0.469 |
| hsa-miR-1260-002896 | 0.453 |
| hsa-miR-363#-001283 | 0.393 |
| hsa-miR-1244-002791 | 0.388 |
| hsa-miR-567-001534 | 0.385 |
| hsa-miR-101-4395364 | −0.230 |
| hsa-miR-218-4373081 | −0.233 |
| hsa-miR-27a#-002445 | −0.234 |
| hsa-miR-330-3p-4373047 | −0.236 |
| hsa-miR-30e-3p-000422 | −0.237 |
| hsa-miR-29b-2#-002166 | −0.239 |
| hsa-miR-411-4381013 | −0.241 |
| hsa-miR-875-5p-002203 | −0.242 |
| hsa-miR-337-5p-4395267 | −0.244 |
| hsa-miR-130a-4373145 | −0.245 |
| hsa-miR-454#-001996 | −0.257 |
| dme-miR-7-000268 | −0.261 |
| hsa-miR-19b-1#-002425 | −0.263 |
| hsa-miR-32-4395220 | −0.263 |
| hsa-miR-137-4373301 | −0.265 |
| hsa-miR-122-4395356 | −0.268 |
| hsa-miR-518a-3p-4395508 | −0.269 |
| hsa-miR-219-5p-4373080 | −0.274 |
| hsa-let-7b-4395446 | −0.278 |
| hsa-miR-655-4381015 | −0.279 |
| hsa-miR-1264-002799 | −0.282 |
| hsa-miR-1262-002852 | −0.289 |
| hsa-miR-518b-4373246 | −0.290 |
| hsa-miR-152-4395170 | −0.292 |
| hsa-miR-338-3p-4395363 | −0.294 |
| hsa-miR-520D-3P-002743 | −0.316 |
| hsa-miR-488-4395468 | −0.354 |
| hsa-miR-551b-4380945 | −0.375 |
| hsa-miR-625-4395542 | −0.382 |
| hsa-miR-519a-4395526 | −0.419 |
| hsa-miR-21-4373090 | −0.429 |

More importantly, we identified a series of miRNA signatures as first generation of diagnostic biomarkers for PD and the progression of PD:

1) miRNA signature composed by 14 miRNAs that distinguishes ILBD to normal controls, which may be used as a diagnostic biomarker for pre-symptomatic PD (FIG. 5): miR-516, miR-191#, miR-449b, miR-497, miR-628-213, miR-23a, miR-29#, miR-488, miR-597, miR-296-5p, miR-671-3p, miR-654-3p, miR-99#;

2) miRNA signature composed of 13 miRNAs that distinguishes normal control subjects from PD, which may be used as a diagnostic biomarker for diagnosis of early PD (FIG. 6): miR-590-3p, miR-213, miR-9#, miR-191#, miR-497, miR-664, miR-99a#, miR-1183, miR-340#, miR-628-3p, miR-7#, miR-29a#, miR-142-3p;

3) miRNA signature composed by 6 miRNAs that distinguishes ILBD from PD, which may change from asymptomatic Lewis Body disease to symptomatic PD, and may be used as a diagnostic biomarker for diagnosis of early PD (FIG. 7): miR-664, miR-1285, miR-1183, miR-143, miR-519a, miR-603;

4) miRNA signature composed by 8 miRNAs that distinguish clinically normal subjects (including normal control and ILBD subjects), which may also be used early diagnostic biomarkers for PD (FIG. 8): miR-590-3p, miR-664, miR-519a, miR-340*, miR-720, miR-142-3p, miR-185, and miR-213; and 5) miRNA signature composed by 7 miRNAs which distinguish PD from PD with dementia, and may be used as a diagnostic biomarker for cognitive impairment in PD patients (FIG. 9): miR-590-3p, miR-213, miR-409-3p, miR-500, miR-7, miR-206 and miR-629.

Example 3 miR-212 and miR-132 Play Important Roles in Pathogenesis of PD and are Novel Therapeutic Targets for Treatment of PD and L-Dopa-Induced Dyskinesia Among the miRNAs in the putamen, which are correlated with the progression of disease, miR-212 and miR-132 are highly expressed the putamen, and are significantly increased (~1.6 fold) in the putamen of PD cases, compared to controls (FIG. 8). miR-212 and miR-132 are clustered in intron 1 of a highly-conserved, non-coding RNA gene on human chromosome 1p13.3, and have high sequence homology with the same seed sequences, therefore, share most of their downstream targets and functions (FIG. 10). Interestingly, mature miR-132 is expressed at a much higher level than miR-212 in the putamen (>60 fold), suggesting that miR-132 plays a major role in the putamen.

Correlation study with all cases regardless of their clinical diagnosis showed that levels of miR-212 and miR-132 expression in the putamen are significantly correlated to the global Lewy-type α-synucleinopathy (LTS) scores and the degree of substantia nigra (SN) pigmented neuron loss score (FIG. 11), with the highest correlation scores among all differentially expressed miRNAs, strongly suggesting that expression of miR-212 and/or miR-132 correlates with SN neurodegeneration and PD pathology, and that misregulation of miR-212 and/or miR-132 are involved in PD. Multiple lines of evidence support that miR-212 and/or miR-132 play important roles in pathogenesis of PD and are novel therapeutic targets for treatment of PD and L-Dopa-induced dyskinesia:

1) Our target prediction analysis showed that Nurr1, a member of nuclear receptor superfamily, is a predicted target of miR-212 and/or miR-132. Nurr1 is essential for the differentiation and survival of nigral dopaminergic neurons5-7. Mutations are associated with PD. Therefore, miR-212 and/or miR-132 may regulate the function and survival of dopaminergic (DA) neurons by modulating Nurr1.

2) Our functional annotation analysis of predicted target genes of miR-212 and miR-132 revealed significant enrichment of genes involved in neurotrophin signaling (p=0.01), MAPK signaling (p=0.008) and longterm potentiation (p=0.02), consistent with reports that miR-212 and miR-132 are neurotrophin- and activity-regulated miRNAs and are important for neural plasticity.

3) NMDA receptors (NMDA-Rs) are shown to mediate neurotrophin- and activity-induced induction of miR-212 and miR-132. In PD, depletion of nigrostriatal DA results in relative glutamatergic overactivity in the striatum, which plays central roles in PD as well as L-dopa induced dyskinesia. Therefore, upregulation of miR-212 and/or miR-132 in PD putamen may be a result of loss of dopamine input and relative overactivity through NMDA-R;

4) miR-212 and miR-132 are shown to target Methyl CpG-binding protein-2 (MeCP2), which promote the expression of brain-derived neurotrophic factor (BDNF), a potent trophic factor for DA neurons, which has been shown to be decreased in substantia nigra (SN) and striatum PD patients and animal models. Therefore, increased of expression of miR-212 and/or miR-132 may inhibit the expression of MeCP2 and BDNF, and contribute to the pathogenesis of PD;

5) miR-212 and miR-132 are shown to promote NF-κB- and p53-activation through repression of silent information regulator 1 (SIRT1), a NAD+-dependent deacetylase, which deacetylates and inactivates p53 and the p65 subunit of NF-κB29-32. Increased p53 and NF-κB activation in SN and striatum promote cellular senescence and apoptosis. Therefore, miR-212 and/or miR-132 may contribute to nigrostriatal neurodegeneration through modulating NF-κB and p53 activation.

Collectively, these data suggest that upregulation of miR-212 and/or miR-132 in the putamen may be a result of loss of nigrostriatal DA and overactivation of NMDA-Rs; miR-212 and/or miR-132 may mediate NMDAR overactivation-induced excitotoxicity and play important roles in the pathogenesis of PD through argeting MeCP2, SIRT1 and Nurr1, modulating Nurr1-, BDNF-, NF-κB- and p53-involved pathogenetic pathways. Therefore, prevention of loss of DA innervation-resulted upregulation of miR-212 and/or miR-132 may be neuroprotective for the nigrostriatal system and prevent the development of PD. miR-212 and/or miR-132 may be novel therapeutic targets for the treatment of PD.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

I claim:

1. A method of identifying a subject at risk of developing or having Parkinson's Disease (PD), the method comprising:
   a) isolating a biological sample from the subject;
   b) detecting a level of expression in a miRNA signature in the biological sample from the subject, the miRNA signature comprising a plurality of miRNAs;
   the plurality of miRNAs comprising:
      i) SEQ ID NOs: 204, 110, 192, 200, 244, 2, 134, 144, 198, 234, 143, 261, 255, and 179 (miR-516-3p, miR-191#, miR-449b, miR-497, miR-628-3p, miR-213, miR-23a, miR-29a#, miR-488, miR-597, miR-296-5p, miR-671-3p, miR-654-3p, and miR-99a#);
      ii) SEQ ID NOs: 1-13, (miR-590-3p, miR-213, miR-9#, miR-191#, miR-497, miR-664, miR-99a#, miR-1183, miR-340#, miR-628-3p, miR-7#, miR-29a#, miR-142-3p);
      iii) SEQ ID NOs: 14-20 and 2 (miR-590-3p, miR-664, miR-519a, miR-340#, miR-720, miR-142-3p, miR-185, and miR-213); or
      iv) SEQ ID NOs: 28, 2 and 30-34 (miR-590-3p, miR-213, miR-409-3p, miR-500, miR-7, miR-206, and miR-629);
   c) comparing the level of expression of the plurality of miRNAs in the sample to a level of expression of the plurality of miRNAs in a reference,
   wherein an increased or decreased level of expression in the sample compared to the level of expression in the reference for each of the plurality of miRNAs identifies the subject as having PD or who is at risk of developing PD.

2. The method of claim 1, wherein the reference is a sample from a normal, healthy subject.

3. The method of claim 1, wherein the plurality of miRNAs comprise SEQ ID NOs: 204, 110, 192, 200, 244, 2, 134, 144, 198, 234, 143, 261, 255, and 179 (miR-516-3p, miR-191#, miR-449b, miR-497, miR-628-3p, miR-213, miR-23a, miR-29a#, miR-488, miR-597, miR-296-5p, miR-671-3p, miR-654-3p, and miR-99a#) and the miRNA signature is indicative of pre-symptomatic PD.

4. The method of claim 1, wherein the plurality of miRNAs comprise SEQ ID NOs: 1-13, (miR-590-3p, miR-213, miR-9#, miR-191#, miR-497, miR-664, miR-99a#, miR-1183, miR-340#, miR-628-3p, miR-7#, miR-29a#, miR-142-3p) and the miRNA signature is indicative of early PD.

5. The method of claim 1, wherein the plurality of miRNAs comprise SEQ ID NOs: 14-20 and 2 (miR-590-3p, miR-664, miR-519a, miR-340#, miR-720, miR-142-3p, miR-185, and miR-213) and the miRNA signature is indicative of early PD.

6. The method of claim 1, wherein the plurality of miRNAs comprise SEQ ID NOs: 28, 2 and 30-34 (miR-590-3p, miR-213, miR-409-3p, miR-500, miR-7, miR-206, and miR-629) and the miRNA signature is indicative of cognitive impairment of PD.

* * * * *

```
                        SEQUENCE LISTING

<160> NUMBER OF SEQ ID NOS: 283

<210> SEQ ID NO 1
<211> LENGTH: 21
<212> TYPE: RNA
<213> ORGANISM: Artificial Sequence
<220> FEATURE:
<223> OTHER INFORMATION: Synthetic hsa_miR_590_3P_002677

<400> SEQUENCE: 1
uaauuuuaug uauaagcuag u                                               21

<210> SEQ ID NO 2
<211> LENGTH: 22
<212> TYPE: RNA
<213> ORGANISM: Artificial Sequence
<220> FEATURE:
<223> OTHER INFORMATION: Synthetic hsa_miR_213_000516

<400> SEQUENCE: 2
accaucgacc guugauugua cc                                              22

<210> SEQ ID NO 3
<211> LENGTH: 22
<212> TYPE: RNA
<213> ORGANISM: Artificial Sequence
<220> FEATURE:
<223> OTHER INFORMATION: Synthetic hsa_miR_9#__002231

<400> SEQUENCE: 3
auaaagcuag auaaccgaaa gu                                              22

<210> SEQ ID NO 4
<211> LENGTH: 22
<212> TYPE: RNA
<213> ORGANISM: Artificial Sequence
<220> FEATURE:
<223> OTHER INFORMATION: Synthetic hsa_miR_191#__002678
```

```
<400> SEQUENCE: 4
gcugcgcuug gauuucgucc cc                                            22

<210> SEQ ID NO 5
<211> LENGTH: 21
<212> TYPE: RNA
<213> ORGANISM: Artificial Sequence
<220> FEATURE:
<223> OTHER INFORMATION: Synthetic hsa_miR_497_001043

<400> SEQUENCE: 5
cagcagcaca cugugguuug u                                             21

<210> SEQ ID NO 6
<211> LENGTH: 23
<212> TYPE: RNA
<213> ORGANISM: Artificial Sequence
<220> FEATURE:
<223> OTHER INFORMATION: Synthetic hsa_miR_664_002897

<400> SEQUENCE: 6
uauucauuua uccccagccu aca                                           23

<210> SEQ ID NO 7
<211> LENGTH: 22
<212> TYPE: RNA
<213> ORGANISM: Artificial Sequence
<220> FEATURE:
<223> OTHER INFORMATION: Synthetic hsa_miR_99a#_002141

<400> SEQUENCE: 7
caagcucgcu ucuauggguc ug                                            22

<210> SEQ ID NO 8
<211> LENGTH: 27
<212> TYPE: RNA
<213> ORGANISM: Artificial Sequence
<220> FEATURE:
<223> OTHER INFORMATION: Synthetic hsa_miR_1183_002841

<400> SEQUENCE: 8
cacuguaggu gauggugaga gugggca                                       27

<210> SEQ ID NO 9
<211> LENGTH: 22
<212> TYPE: RNA
<213> ORGANISM: Artificial Sequence
<220> FEATURE:
<223> OTHER INFORMATION: Synthetic hsa_miR_340#_002259

<400> SEQUENCE: 9
uccgucucag uuacuuuaua gc                                            22

<210> SEQ ID NO 10
<211> LENGTH: 21
<212> TYPE: RNA
<213> ORGANISM: Artificial Sequence
<220> FEATURE:
<223> OTHER INFORMATION: Synthetic hsa_miR_628_3p_002434

<400> SEQUENCE: 10
ucuaguaaga guggcagucg a                                             21

<210> SEQ ID NO 11
<211> LENGTH: 22
```

```
<212> TYPE: RNA
<213> ORGANISM: Artificial Sequence
<220> FEATURE:
<223> OTHER INFORMATION: Synthetic rno_miR_7#__001338

<400> SEQUENCE: 11
caacaaauca cagucugcca ua                                              22

<210> SEQ ID NO 12
<211> LENGTH: 22
<212> TYPE: RNA
<213> ORGANISM: Artificial Sequence
<220> FEATURE:
<223> OTHER INFORMATION: Synthetic hsa_miR_29a#__002447

<400> SEQUENCE: 12
acugauuucu uuugguguuc ag                                              22

<210> SEQ ID NO 13
<211> LENGTH: 23
<212> TYPE: RNA
<213> ORGANISM: Artificial Sequence
<220> FEATURE:
<223> OTHER INFORMATION: Synthetic hsa_miR_142_3p_4373136

<400> SEQUENCE: 13
uguaguguuu ccuacuuuau gga                                             23

<210> SEQ ID NO 14
<211> LENGTH: 21
<212> TYPE: RNA
<213> ORGANISM: Artificial Sequence
<220> FEATURE:
<223> OTHER INFORMATION: Synthetic hsa-miR-590-3P-002677

<400> SEQUENCE: 14
uaauuuuaug uauaagcuag u                                               21

<210> SEQ ID NO 15
<211> LENGTH: 23
<212> TYPE: RNA
<213> ORGANISM: Artificial Sequence
<220> FEATURE:
<223> OTHER INFORMATION: Synthetic hsa-miR-664-002897

<400> SEQUENCE: 15
uauucauuua uccccagccu aca                                             23

<210> SEQ ID NO 16
<211> LENGTH: 22
<212> TYPE: RNA
<213> ORGANISM: Artificial Sequence
<220> FEATURE:
<223> OTHER INFORMATION: Synthetic hsa-miR-519a-4395526

<400> SEQUENCE: 16
aaagugcauc cuuuuagagu gu                                              22

<210> SEQ ID NO 17
<211> LENGTH: 22
<212> TYPE: RNA
<213> ORGANISM: Artificial Sequence
<220> FEATURE:
<223> OTHER INFORMATION: Synthetic hsa-miR-340#-002259

<400> SEQUENCE: 17
```
uccgucucag uuacuuuaua gc					22

<210> SEQ ID NO 18
<211> LENGTH: 17
<212> TYPE: RNA
<213> ORGANISM: Artificial Sequence
<220> FEATURE:
<223> OTHER INFORMATION: Synthetic hsa-miR-720-002895

<400> SEQUENCE: 18
ucucgcuggg gccucca					17

<210> SEQ ID NO 19
<211> LENGTH: 23
<212> TYPE: RNA
<213> ORGANISM: Artificial Sequence
<220> FEATURE:
<223> OTHER INFORMATION: Synthetic hsa-miR-142-3p-4373136

<400> SEQUENCE: 19
uguaguguuu ccuacuuuau gga					23

<210> SEQ ID NO 20
<211> LENGTH: 22
<212> TYPE: RNA
<213> ORGANISM: Artificial Sequence
<220> FEATURE:
<223> OTHER INFORMATION: Synthetic hsa-miR-185-4395382

<400> SEQUENCE: 20
uggagagaaa ggcaguuccu ga					22

<210> SEQ ID NO 21
<211> LENGTH: 22
<212> TYPE: RNA
<213> ORGANISM: Artificial Sequence
<220> FEATURE:
<223> OTHER INFORMATION: Synthetic hsa-miR-213-000516

<400> SEQUENCE: 21
accaucgacc guugauugua cc					22

<210> SEQ ID NO 22
<211> LENGTH: 23
<212> TYPE: RNA
<213> ORGANISM: Artificial Sequence
<220> FEATURE:
<223> OTHER INFORMATION: Synthetic hsa-miR-664-002897

<400> SEQUENCE: 22
uauucauuua uccccagccu aca					23

<210> SEQ ID NO 23
<211> LENGTH: 22
<212> TYPE: RNA
<213> ORGANISM: Artificial Sequence
<220> FEATURE:
<223> OTHER INFORMATION: Synthetic hsa-miR-1285-002822

<400> SEQUENCE: 23
ucugggcaac aaagugagac cu					22

<210> SEQ ID NO 24
<211> LENGTH: 27
<212> TYPE: RNA
<213> ORGANISM: Artificial Sequence

```
<220> FEATURE:
<223> OTHER INFORMATION: Synthetic hsa-miR-1183-002841

<400> SEQUENCE: 24
cacuguaggu gauggugaga gugggca                                          27

<210> SEQ ID NO 25
<211> LENGTH: 22
<212> TYPE: RNA
<213> ORGANISM: Artificial Sequence
<220> FEATURE:
<223> OTHER INFORMATION: Synthetic hsa-miR-143-4395360

<400> SEQUENCE: 25
ugagaugaag cacuguagcu ca                                               22

<210> SEQ ID NO 26
<211> LENGTH: 22
<212> TYPE: RNA
<213> ORGANISM: Artificial Sequence
<220> FEATURE:
<223> OTHER INFORMATION: Synthetic hsa-miR-519a-4395526

<400> SEQUENCE: 26
aaagugcauc cuuuuagagu gu                                               22

<210> SEQ ID NO 27
<211> LENGTH: 22
<212> TYPE: RNA
<213> ORGANISM: Artificial Sequence
<220> FEATURE:
<223> OTHER INFORMATION: Synthetic hsa-miR-603-001566

<400> SEQUENCE: 27
cacacacugc aauuacuuuu gc                                               22

<210> SEQ ID NO 28
<211> LENGTH: 21
<212> TYPE: RNA
<213> ORGANISM: Artificial Sequence
<220> FEATURE:
<223> OTHER INFORMATION: Synthetic hsa_miR_590_3P_002677

<400> SEQUENCE: 28
uaauuuuaug uauaagcuag u                                                21

<210> SEQ ID NO 29
<211> LENGTH: 22
<212> TYPE: RNA
<213> ORGANISM: Artificial Sequence
<220> FEATURE:
<223> OTHER INFORMATION: Synthetic hsa_miR_213_000516

<400> SEQUENCE: 29
accaucgacc guugauugua cc                                               22

<210> SEQ ID NO 30
<211> LENGTH: 22
<212> TYPE: RNA
<213> ORGANISM: Artificial Sequence
<220> FEATURE:
<223> OTHER INFORMATION: Synthetic hsa_miR_409_3p_002332

<400> SEQUENCE: 30
gaauguugcu cggugaaccc cu                                               22
```

```
<210> SEQ ID NO 31
<211> LENGTH: 23
<212> TYPE: RNA
<213> ORGANISM: Artificial Sequence
<220> FEATURE:
<223> OTHER INFORMATION: Synthetichsa_miR_500_4395539

<400> SEQUENCE: 31
uaauccuugc uaccugggug aga                                              23

<210> SEQ ID NO 32
<211> LENGTH: 23
<212> TYPE: RNA
<213> ORGANISM: Artificial Sequence
<220> FEATURE:
<223> OTHER INFORMATION: Synthetic dme_miR_7_000268

<400> SEQUENCE: 32
uggaagacua gugauuuugu ugu                                              23

<210> SEQ ID NO 33
<211> LENGTH: 22
<212> TYPE: RNA
<213> ORGANISM: Artificial Sequence
<220> FEATURE:
<223> OTHER INFORMATION: Synthetic hsa_miR_206_000510

<400> SEQUENCE: 33
uggaauguaa ggaagugugu gg                                               22

<210> SEQ ID NO 34
<211> LENGTH: 22
<212> TYPE: RNA
<213> ORGANISM: Artificial Sequence
<220> FEATURE:
<223> OTHER INFORMATION: Synthetic hsa_miR_629_001562

<400> SEQUENCE: 34
guucucccaa cguaagccca gc                                               22

<210> SEQ ID NO 35
<211> LENGTH: 23
<212> TYPE: RNA
<213> ORGANISM: Artificial Sequence
<220> FEATURE:
<223> OTHER INFORMATION: Synthetic dme-miR-7-000268

<400> SEQUENCE: 35
uggaagacua gugauuuugu ugu                                              23

<210> SEQ ID NO 36
<211> LENGTH: 22
<212> TYPE: RNA
<213> ORGANISM: Artificial Sequence
<220> FEATURE:
<223> OTHER INFORMATION: Synthetic hsa-let-7c-4373167

<400> SEQUENCE: 36
ugagguagua gguuguaugg uu                                               22

<210> SEQ ID NO 37
<211> LENGTH: 21
<212> TYPE: RNA
<213> ORGANISM: Artificial Sequence
<220> FEATURE:
<223> OTHER INFORMATION: Synthetic hsa-let-7d-4395394
```

<400> SEQUENCE: 37
agagguagua gguugcauag u                                      21

<210> SEQ ID NO 38
<211> LENGTH: 22
<212> TYPE: RNA
<213> ORGANISM: Artificial Sequence
<220> FEATURE:
<223> OTHER INFORMATION: Synthetic hsa-let-7f-1#-002417

<400> SEQUENCE: 38
cuauacaauc uauugccuuc cc                                     22

<210> SEQ ID NO 39
<211> LENGTH: 22
<212> TYPE: RNA
<213> ORGANISM: Artificial Sequence
<220> FEATURE:
<223> OTHER INFORMATION: Synthetic hsa-miR-100#-002142

<400> SEQUENCE: 39
caagcuugua ucuauaggua ug                                     22

<210> SEQ ID NO 40
<211> LENGTH: 21
<212> TYPE: RNA
<213> ORGANISM: Artificial Sequence
<220> FEATURE:
<223> OTHER INFORMATION: Synthetic hsa-miR-101#-002143

<400> SEQUENCE: 40
uacaguacug ugauaacuga a                                      21

<210> SEQ ID NO 41
<211> LENGTH: 22
<212> TYPE: RNA
<213> ORGANISM: Artificial Sequence
<220> FEATURE:
<223> OTHER INFORMATION: Synthetic hsa-miR-101-4395364

<400> SEQUENCE: 41
caguuaucac agugcugaug cu                                     22

<210> SEQ ID NO 42
<211> LENGTH: 23
<212> TYPE: RNA
<213> ORGANISM: Artificial Sequence
<220> FEATURE:
<223> OTHER INFORMATION: Synthetic hsa-miR-105-4395278

<400> SEQUENCE: 42
ucaaaugcuc agacuccugu ggu                                    23

<210> SEQ ID NO 43
<211> LENGTH: 22
<212> TYPE: RNA
<213> ORGANISM: Artificial Sequence
<220> FEATURE:
<223> OTHER INFORMATION: Synthetic hsa-miR-106b#-002380

<400> SEQUENCE: 43
ccgcacugug gguacuugcu gc                                     22

<210> SEQ ID NO 44

```
<211> LENGTH: 23
<212> TYPE: RNA
<213> ORGANISM: Artificial Sequence
<220> FEATURE:
<223> OTHER INFORMATION: Synthetic hsa-miR-107-4373154

<400> SEQUENCE: 44
agcagcauug uacagggcua uca                                              23

<210> SEQ ID NO 45
<211> LENGTH: 23
<212> TYPE: RNA
<213> ORGANISM: Artificial Sequence
<220> FEATURE:
<223> OTHER INFORMATION: Synthetic hsa-miR-10b-4395329

<400> SEQUENCE: 45
uacccuguag aaccgaauuu gug                                              23

<210> SEQ ID NO 46
<211> LENGTH: 27
<212> TYPE: RNA
<213> ORGANISM: Artificial Sequence
<220> FEATURE:
<223> OTHER INFORMATION: Synthetic hsa-miR-1183-002841

<400> SEQUENCE: 46
cacuguaggu gauggugaga gugggca                                          27

<210> SEQ ID NO 47
<211> LENGTH: 24
<212> TYPE: RNA
<213> ORGANISM: Artificial Sequence
<220> FEATURE:
<223> OTHER INFORMATION: Synthetic hsa-miR-1201-002781

<400> SEQUENCE: 47
agccugauua aacacaugcu cuga                                             24

<210> SEQ ID NO 48
<211> LENGTH: 22
<212> TYPE: RNA
<213> ORGANISM: Artificial Sequence
<220> FEATURE:
<223> OTHER INFORMATION: Synthetic hsa-miR-122-4395356

<400> SEQUENCE: 48
uggaguguga caaugguguu ug                                               22

<210> SEQ ID NO 49
<211> LENGTH: 21
<212> TYPE: RNA
<213> ORGANISM: Artificial Sequence
<220> FEATURE:
<223> OTHER INFORMATION: Synthetic hsa-miR-1224-3P-002752

<400> SEQUENCE: 49
ccccaccucc ucucuccuca g                                                21

<210> SEQ ID NO 50
<211> LENGTH: 26
<212> TYPE: RNA
<213> ORGANISM: Artificial Sequence
<220> FEATURE:
<223> OTHER INFORMATION: Synthetic hsa-miR-1226#-002758

<400> SEQUENCE: 50
```

```
gugagggcau gcaggccugg augggg                                              26

<210> SEQ ID NO 51
<211> LENGTH: 20
<212> TYPE: RNA
<213> ORGANISM: Artificial Sequence
<220> FEATURE:
<223> OTHER INFORMATION: Synthetic hsa-miR-1227-002769

<400> SEQUENCE: 51
cgugccaccc uuuucccag                                                      20

<210> SEQ ID NO 52
<211> LENGTH: 20
<212> TYPE: RNA
<213> ORGANISM: Artificial Sequence
<220> FEATURE:
<223> OTHER INFORMATION: Synthetic hsa-miR-1233-002768

<400> SEQUENCE: 52
ugagcccugu ccucccgcag                                                     20

<210> SEQ ID NO 53
<211> LENGTH: 20
<212> TYPE: RNA
<213> ORGANISM: Artificial Sequence
<220> FEATURE:
<223> OTHER INFORMATION: Synthetic hsa-miR-1238-002927

<400> SEQUENCE: 53
cuuccucguc ugucugcccc                                                     20

<210> SEQ ID NO 54
<211> LENGTH: 26
<212> TYPE: RNA
<213> ORGANISM: Artificial Sequence
<220> FEATURE:
<223> OTHER INFORMATION: Synthetic hsa-miR-1244-002791

<400> SEQUENCE: 54
aaguaguugg uuuguaugag augguu                                              26

<210> SEQ ID NO 55
<211> LENGTH: 22
<212> TYPE: RNA
<213> ORGANISM: Artificial Sequence
<220> FEATURE:
<223> OTHER INFORMATION: Synthetic hsa-miR-124-4373295

<400> SEQUENCE: 55
uuaaggcacg cggugaaugc ca                                                  22

<210> SEQ ID NO 56
<211> LENGTH: 27
<212> TYPE: RNA
<213> ORGANISM: Artificial Sequence
<220> FEATURE:
<223> OTHER INFORMATION: Synthetic hsa-miR-1248-002870

<400> SEQUENCE: 56
accuucuugu auaagcacug ugcuaaa                                             27

<210> SEQ ID NO 57
<211> LENGTH: 22
<212> TYPE: RNA
```

<213> ORGANISM: Artificial Sequence
<220> FEATURE:
<223> OTHER INFORMATION: Synthetic hsa-miR-1255B-002801

<400> SEQUENCE: 57
cggaugagca aagaaagugg uu                                              22

<210> SEQ ID NO 58
<211> LENGTH: 22
<212> TYPE: RNA
<213> ORGANISM: Artificial Sequence
<220> FEATURE:
<223> OTHER INFORMATION: Synthetic hsa-miR-1256-002850

<400> SEQUENCE: 58
aggcauugac uucucacuag cu                                              22

<210> SEQ ID NO 59
<211> LENGTH: 24
<212> TYPE: RNA
<213> ORGANISM: Artificial Sequence
<220> FEATURE:
<223> OTHER INFORMATION: Synthetic hsa-miR-125a-5p-4395309

<400> SEQUENCE: 59
ucccugagac ccuuuaaccu guga                                            24

<210> SEQ ID NO 60
<211> LENGTH: 22
<212> TYPE: RNA
<213> ORGANISM: Artificial Sequence
<220> FEATURE:
<223> OTHER INFORMATION: Synthetic hsa-miR-125b2#-002158

<400> SEQUENCE: 60
ucacaaguca ggcucuuggg ac                                              22

<210> SEQ ID NO 61
<211> LENGTH: 22
<212> TYPE: RNA
<213> ORGANISM: Artificial Sequence
<220> FEATURE:
<223> OTHER INFORMATION: Synthetic hsa-miR-125b-4373148

<400> SEQUENCE: 61
ucccugagac ccuaacuugu ga                                              22

<210> SEQ ID NO 62
<211> LENGTH: 21
<212> TYPE: RNA
<213> ORGANISM: Artificial Sequence
<220> FEATURE:
<223> OTHER INFORMATION: Synthetichsa-miR-126#-000451

<400> SEQUENCE: 62
cauuauuacu uuugguacgc g                                               21

<210> SEQ ID NO 63
<211> LENGTH: 18
<212> TYPE: RNA
<213> ORGANISM: Artificial Sequence
<220> FEATURE:
<223> OTHER INFORMATION: Synthetic hsa-miR-1260-002896

<400> SEQUENCE: 63
aucccaccuc ugccacca                                                   18

```
<210> SEQ ID NO 64
<211> LENGTH: 23
<212> TYPE: RNA
<213> ORGANISM: Artificial Sequence
<220> FEATURE:
<223> OTHER INFORMATION: Synthetic hsa-miR-1264-002799

<400> SEQUENCE: 64
caagucuuau uugagcaccu guu                                              23

<210> SEQ ID NO 65
<211> LENGTH: 22
<212> TYPE: RNA
<213> ORGANISM: Artificial Sequence
<220> FEATURE:
<223> OTHER INFORMATION: Synthetic hsa-miR-1269-002789

<400> SEQUENCE: 65
cuggacugag ccgugcuacu gg                                               22

<210> SEQ ID NO 66
<211> LENGTH: 23
<212> TYPE: RNA
<213> ORGANISM: Artificial Sequence
<220> FEATURE:
<223> OTHER INFORMATION: Synthetic hsa-miR-1270-002807

<400> SEQUENCE: 66
cuggagauau ggaagagcug ugu                                              23

<210> SEQ ID NO 67
<211> LENGTH: 22
<212> TYPE: RNA
<213> ORGANISM: Artificial Sequence
<220> FEATURE:
<223> OTHER INFORMATION: Synthetic hsa-miR-1271-002779

<400> SEQUENCE: 67
cuuggcaccu agcaagcacu ca                                               22

<210> SEQ ID NO 68
<211> LENGTH: 22
<212> TYPE: RNA
<213> ORGANISM: Artificial Sequence
<220> FEATURE:
<223> OTHER INFORMATION: Synthetic hsa-miR-127-5p-4395340

<400> SEQUENCE: 68
cugaagcuca gagggcucug au                                               22

<210> SEQ ID NO 69
<211> LENGTH: 20
<212> TYPE: RNA
<213> ORGANISM: Artificial Sequence
<220> FEATURE:
<223> OTHER INFORMATION: Synthetic hsa-miR-1282-002803

<400> SEQUENCE: 69
ucguuugccu uuucugcuu                                                   20

<210> SEQ ID NO 70
<211> LENGTH: 19
<212> TYPE: RNA
<213> ORGANISM: Artificial Sequence
<220> FEATURE:
```

```
<223> OTHER INFORMATION: Synthetic hsa-miR-1290-002863

<400> SEQUENCE: 70
uggauuuuug gaucaggga                                                   19

<210> SEQ ID NO 71
<211> LENGTH: 24
<212> TYPE: RNA
<213> ORGANISM: Artificial Sequence
<220> FEATURE:
<223> OTHER INFORMATION: Synthetic hsa-miR-1291-002838

<400> SEQUENCE: 71
uggcccugac ugaagaccag cagu                                             24

<210> SEQ ID NO 72
<211> LENGTH: 22
<212> TYPE: RNA
<213> ORGANISM: Artificial Sequence
<220> FEATURE:
<223> OTHER INFORMATION: Synthetic hsa-miR-129-3p-4373297

<400> SEQUENCE: 72
aagcccuuac cccaaaaagu au                                               22

<210> SEQ ID NO 73
<211> LENGTH: 22
<212> TYPE: RNA
<213> ORGANISM: Artificial Sequence
<220> FEATURE:
<223> OTHER INFORMATION: Synthetic hsa-miR-1298-002861

<400> SEQUENCE: 73
uucauucggc uguccagaug ua                                               22

<210> SEQ ID NO 74
<211> LENGTH: 18
<212> TYPE: RNA
<213> ORGANISM: Artificial Sequence
<220> FEATURE:
<223> OTHER INFORMATION: Synthetic hsa-miR-1300-002902

<400> SEQUENCE: 74
uugagaagga ggcugcug                                                    18

<210> SEQ ID NO 75
<211> LENGTH: 24
<212> TYPE: RNA
<213> ORGANISM: Artificial Sequence
<220> FEATURE:
<223> OTHER INFORMATION: Synthetic hsa-miR-1301-002827

<400> SEQUENCE: 75
uugcagcugc cugggaguga cuuc                                             24

<210> SEQ ID NO 76
<211> LENGTH: 22
<212> TYPE: RNA
<213> ORGANISM: Artificial Sequence
<220> FEATURE:
<223> OTHER INFORMATION: Synthetic hsa-miR-1303-002792

<400> SEQUENCE: 76
uuuagagacg gggucuugcu cu                                               22
```

```
<210> SEQ ID NO 77
<211> LENGTH: 22
<212> TYPE: RNA
<213> ORGANISM: Artificial Sequence
<220> FEATURE:
<223> OTHER INFORMATION: Synthetic hsa-miR-130a-4373145

<400> SEQUENCE: 77
cagugcaaug uuaaaagggc au                                              22

<210> SEQ ID NO 78
<211> LENGTH: 22
<212> TYPE: RNA
<213> ORGANISM: Artificial Sequence
<220> FEATURE:
<223> OTHER INFORMATION: Synthetic hsa-miR-130b-4373144

<400> SEQUENCE: 78
cagugcaaug augaaagggc au                                              22

<210> SEQ ID NO 79
<211> LENGTH: 22
<212> TYPE: RNA
<213> ORGANISM: Artificial Sequence
<220> FEATURE:
<223> OTHER INFORMATION: Synthetic hsa-miR-132-4373143

<400> SEQUENCE: 79
uaacagucua cagccauggu cg                                              22

<210> SEQ ID NO 80
<211> LENGTH: 23
<212> TYPE: RNA
<213> ORGANISM: Artificial Sequence
<220> FEATURE:
<223> OTHER INFORMATION: Synthetic hsa-miR-135a-4373140

<400> SEQUENCE: 80
uauggcuuuu uauuccuaug uga                                             23

<210> SEQ ID NO 81
<211> LENGTH: 22
<212> TYPE: RNA
<213> ORGANISM: Artificial Sequence
<220> FEATURE:
<223> OTHER INFORMATION: Synthetic hsa-miR-135b#-002159

<400> SEQUENCE: 81
auguagggcu aaaagccaug gg                                              22

<210> SEQ ID NO 82
<211> LENGTH: 23
<212> TYPE: RNA
<213> ORGANISM: Artificial Sequence
<220> FEATURE:
<223> OTHER INFORMATION: Synthetic hsa-miR-135b-4395372

<400> SEQUENCE: 82
uauggcuuuu cauuccuaug uga                                             23

<210> SEQ ID NO 83
<211> LENGTH: 22
<212> TYPE: RNA
<213> ORGANISM: Artificial Sequence
<220> FEATURE:
<223> OTHER INFORMATION: Synthetic hsa-miR-136#-002100
```

<400> SEQUENCE: 83
caucaucguc ucaaaugagu cu                                    22

<210> SEQ ID NO 84
<211> LENGTH: 22
<212> TYPE: RNA
<213> ORGANISM: Artificial Sequence
<220> FEATURE:
<223> OTHER INFORMATION: Synthetic hsa-miR-137-4373301

<400> SEQUENCE: 84
uauugcuuaa gaauacgcgu ag                                    22

<210> SEQ ID NO 85
<211> LENGTH: 23
<212> TYPE: RNA
<213> ORGANISM: Artificial Sequence
<220> FEATURE:
<223> OTHER INFORMATION: Synthetic hsa-miR-138-2#-002144

<400> SEQUENCE: 85
agcugguguu gugaaucagg ccg                                   23

<210> SEQ ID NO 86
<211> LENGTH: 22
<212> TYPE: RNA
<213> ORGANISM: Artificial Sequence
<220> FEATURE:
<223> OTHER INFORMATION: Synthetic hsa-miR-138-4395395

<400> SEQUENCE: 86
gcuauuucac gacaccaggg uu                                    22

<210> SEQ ID NO 87
<211> LENGTH: 22
<212> TYPE: RNA
<213> ORGANISM: Artificial Sequence
<220> FEATURE:
<223> OTHER INFORMATION: Synthetic hsa-miR-141-4373137

<400> SEQUENCE: 87
uaacacuguc ugguaaagau gg                                    22

<210> SEQ ID NO 88
<211> LENGTH: 23
<212> TYPE: RNA
<213> ORGANISM: Artificial Sequence
<220> FEATURE:
<223> OTHER INFORMATION: Synthetic hsa-miR-142-3p-4373136

<400> SEQUENCE: 88
uguaguguuu ccuacuuuau gga                                   23

<210> SEQ ID NO 89
<211> LENGTH: 21
<212> TYPE: RNA
<213> ORGANISM: Artificial Sequence
<220> FEATURE:
<223> OTHER INFORMATION: Synthetic hsa-miR-143-4395360

<400> SEQUENCE: 89
ugagaugaag cacuguagcu c                                     21

<210> SEQ ID NO 90
<211> LENGTH: 21

```
<212> TYPE: RNA
<213> ORGANISM: Artificial Sequence
<220> FEATURE:
<223> OTHER INFORMATION: Synthetic hsa-miR-1-4395333

<400> SEQUENCE: 90
uggaauguaa agaaguaugu a                                              21

<210> SEQ ID NO 91
<211> LENGTH: 22
<212> TYPE: RNA
<213> ORGANISM: Artificial Sequence
<220> FEATURE:
<223> OTHER INFORMATION: Synthetic hsa-miR-144#-002148

<400> SEQUENCE: 91
ggauaucauc auauacugua ag                                             22

<210> SEQ ID NO 92
<211> LENGTH: 20
<212> TYPE: RNA
<213> ORGANISM: Artificial Sequence
<220> FEATURE:
<223> OTHER INFORMATION: Synthetic hsa-miR-144-002676

<400> SEQUENCE: 92
uacaguauag augauguacu                                                20

<210> SEQ ID NO 93
<211> LENGTH: 22
<212> TYPE: RNA
<213> ORGANISM: Artificial Sequence
<220> FEATURE:
<223> OTHER INFORMATION: Synthetic hsa-miR-145#-002149

<400> SEQUENCE: 93
ggauuccugg aaauacuguu cu                                             22

<210> SEQ ID NO 94
<211> LENGTH: 23
<212> TYPE: RNA
<213> ORGANISM: Artificial Sequence
<220> FEATURE:
<223> OTHER INFORMATION: Synthetic hsa-miR-145-4395389

<400> SEQUENCE: 94
guccaguuuu cccaggaauc ccu                                            23

<210> SEQ ID NO 95
<211> LENGTH: 22
<212> TYPE: RNA
<213> ORGANISM: Artificial Sequence
<220> FEATURE:
<223> OTHER INFORMATION: Synthetic hsa-miR-146a#-002163

<400> SEQUENCE: 95
ccucugaaau ucaguucuuc ag                                             22

<210> SEQ ID NO 96
<211> LENGTH: 22
<212> TYPE: RNA
<213> ORGANISM: Artificial Sequence
<220> FEATURE:
<223> OTHER INFORMATION: Synthetic hsa-miR-146b-5p-4373178

<400> SEQUENCE: 96
```
ugagaacuga auuccauagg cu                                           22

<210> SEQ ID NO 97
<211> LENGTH: 22
<212> TYPE: RNA
<213> ORGANISM: Artificial Sequence
<220> FEATURE:
<223> OTHER INFORMATION: Synthetic hsa-miR-148a-4373130

<400> SEQUENCE: 97
ucagugcacu acagaacuuu gu                                           22

<210> SEQ ID NO 98
<211> LENGTH: 22
<212> TYPE: RNA
<213> ORGANISM: Artificial Sequence
<220> FEATURE:
<223> OTHER INFORMATION: Synthetic hsa-miR-148b#-002160

<400> SEQUENCE: 98
aaguucuguu auacacucag gc                                           22

<210> SEQ ID NO 99
<211> LENGTH: 21
<212> TYPE: RNA
<213> ORGANISM: Artificial Sequence
<220> FEATURE:
<223> OTHER INFORMATION: Synthetic hsa-miR-149#-002164

<400> SEQUENCE: 99
agggagggac gggggcugug c                                            21

<210> SEQ ID NO 100
<211> LENGTH: 21
<212> TYPE: RNA
<213> ORGANISM: Artificial Sequence
<220> FEATURE:
<223> OTHER INFORMATION: Synthetic hsa-miR-151-5P-002642

<400> SEQUENCE: 100
ucgaggagcu cacagucuag u                                            21

<210> SEQ ID NO 101
<211> LENGTH: 20
<212> TYPE: RNA
<213> ORGANISM: Artificial Sequence
<220> FEATURE:
<223> OTHER INFORMATION: Synthetic hsa-miR-153-4373305

<400> SEQUENCE: 101
uugcauaguc acaaaaguga                                              20

<210> SEQ ID NO 102
<211> LENGTH: 22
<212> TYPE: RNA
<213> ORGANISM: Artificial Sequence
<220> FEATURE:
<223> OTHER INFORMATION: Synthetic hsa-miR-154#-000478

<400> SEQUENCE: 102
aaucauacac gguugaccua uu                                           22

<210> SEQ ID NO 103
<211> LENGTH: 22
<212> TYPE: RNA
<213> ORGANISM: Artificial Sequence

```
<220> FEATURE:
<223> OTHER INFORMATION: Synthetic hsa-miR-15a-4373123

<400> SEQUENCE: 103
uagcagcaca uaaugguuug ug                                              22

<210> SEQ ID NO 104
<211> LENGTH: 22
<212> TYPE: RNA
<213> ORGANISM: Artificial Sequence
<220> FEATURE:
<223> OTHER INFORMATION: Synthetic hsa-miR-181a2#-002317

<400> SEQUENCE: 104
accacugacc guugacugua cc                                              22

<210> SEQ ID NO 105
<211> LENGTH: 23
<212> TYPE: RNA
<213> ORGANISM: Artificial Sequence
<220> FEATURE:
<223> OTHER INFORMATION: Synthetic hsa-miR-181a-4373117

<400> SEQUENCE: 105
aacauucaac gcugucggug agu                                             23

<210> SEQ ID NO 106
<211> LENGTH: 22
<212> TYPE: RNA
<213> ORGANISM: Artificial Sequence
<220> FEATURE:
<223> OTHER INFORMATION: Synthetic hsa-miR-183#-002270

<400> SEQUENCE: 106
uauggcacug guagaauuca cu                                              22

<210> SEQ ID NO 107
<211> LENGTH: 22
<212> TYPE: RNA
<213> ORGANISM: Artificial Sequence
<220> FEATURE:
<223> OTHER INFORMATION: Synthetic hsa-miR-183-4395380

<400> SEQUENCE: 107
gugaauuacc gaagggccau aa                                              22

<210> SEQ ID NO 108
<211> LENGTH: 22
<212> TYPE: RNA
<213> ORGANISM: Artificial Sequence
<220> FEATURE:
<223> OTHER INFORMATION: Synthetic hsa-miR-184-4373113

<400> SEQUENCE: 108
uggacggaga acugauaagg gu                                              22

<210> SEQ ID NO 109
<211> LENGTH: 23
<212> TYPE: RNA
<213> ORGANISM: Artificial Sequence
<220> FEATURE:
<223> OTHER INFORMATION: Synthetic hsa-miR-18a-4395533

<400> SEQUENCE: 109
uaaggugcau cuagugcaga uag                                             23
```

<210> SEQ ID NO 110
<211> LENGTH: 22
<212> TYPE: RNA
<213> ORGANISM: Artificial Sequence
<220> FEATURE:
<223> OTHER INFORMATION: Synthetic hsa-miR-191#-002678

<400> SEQUENCE: 110
gcugcgcuug gauuucgucc cc                                              22

<210> SEQ ID NO 111
<211> LENGTH: 21
<212> TYPE: RNA
<213> ORGANISM: Artificial Sequence
<220> FEATURE:
<223> OTHER INFORMATION: Synthetic hsa-miR-192-4373108

<400> SEQUENCE: 111
cugaccuaug aauugacagc c                                               21

<210> SEQ ID NO 112
<211> LENGTH: 22
<212> TYPE: RNA
<213> ORGANISM: Artificial Sequence
<220> FEATURE:
<223> OTHER INFORMATION: Synthetic hsa-miR-193a-5p-4395392

<400> SEQUENCE: 112
ugggucuuug cgggcgagau ga                                              22

<210> SEQ ID NO 113
<211> LENGTH: 21
<212> TYPE: RNA
<213> ORGANISM: Artificial Sequence
<220> FEATURE:
<223> OTHER INFORMATION: Synthetic hsa-miR-195-4373105

<400> SEQUENCE: 113
uagcagcaca gaaauauugg c                                               21

<210> SEQ ID NO 114
<211> LENGTH: 22
<212> TYPE: RNA
<213> ORGANISM: Artificial Sequence
<220> FEATURE:
<223> OTHER INFORMATION: Synthetic hsa-miR-196b-4395326

<400> SEQUENCE: 114
uagguaguuu ccuguuguug gg                                              22

<210> SEQ ID NO 115
<211> LENGTH: 22
<212> TYPE: RNA
<213> ORGANISM: Artificial Sequence
<220> FEATURE:
<223> OTHER INFORMATION: Synthetic hsa-miR-197-4373102

<400> SEQUENCE: 115
uucaccaccu ucuccaccca gc                                              22

<210> SEQ ID NO 116
<211> LENGTH: 22
<212> TYPE: RNA
<213> ORGANISM: Artificial Sequence
<220> FEATURE:
<223> OTHER INFORMATION: Synthetic hsa-miR-198-4395384

```
<400> SEQUENCE: 116
gguccagagg ggagauaggu uc                                              22

<210> SEQ ID NO 117
<211> LENGTH: 23
<212> TYPE: RNA
<213> ORGANISM: Artificial Sequence
<220> FEATURE:
<223> OTHER INFORMATION: Synthetic hsa-miR-199a-5p-4373272

<400> SEQUENCE: 117
cccaguguuc agacuaccug uuc                                             23

<210> SEQ ID NO 118
<211> LENGTH: 23
<212> TYPE: RNA
<213> ORGANISM: Artificial Sequence
<220> FEATURE:
<223> OTHER INFORMATION: Synthetic hsa-miR-19b-4373098

<400> SEQUENCE: 118
ugugcaaauc caugcaaaac uga                                             23

<210> SEQ ID NO 119
<211> LENGTH: 22
<212> TYPE: RNA
<213> ORGANISM: Artificial Sequence
<220> FEATURE:
<223> OTHER INFORMATION: Synthetic hsa-miR-200b-4395362

<400> SEQUENCE: 119
uaauacugcc ugguaaugau ga                                              22

<210> SEQ ID NO 120
<211> LENGTH: 20
<212> TYPE: RNA
<213> ORGANISM: Artificial Sequence
<220> FEATURE:
<223> OTHER INFORMATION: Synthetic hsa-miR-202-4395474

<400> SEQUENCE: 120
agagguauag ggcaugggaa                                                 20

<210> SEQ ID NO 121
<211> LENGTH: 22
<212> TYPE: RNA
<213> ORGANISM: Artificial Sequence
<220> FEATURE:
<223> OTHER INFORMATION: Synthetic hsa-miR-203-4373095

<400> SEQUENCE: 121
gugaaauguu uaggaccacu ag                                              22

<210> SEQ ID NO 122
<211> LENGTH: 22
<212> TYPE: RNA
<213> ORGANISM: Artificial Sequence
<220> FEATURE:
<223> OTHER INFORMATION: Synthetic hsa-miR-206-000510

<400> SEQUENCE: 122
uggaauguaa ggaagugugu gg                                              22

<210> SEQ ID NO 123
```

```
<211> LENGTH: 22
<212> TYPE: RNA
<213> ORGANISM: Artificial Sequence
<220> FEATURE:
<223> OTHER INFORMATION: Synthetic hsa-miR-211-4373088

<400> SEQUENCE: 123
uucccuuugu cauccuucgc cu                                            22

<210> SEQ ID NO 124
<211> LENGTH: 21
<212> TYPE: RNA
<213> ORGANISM: Artificial Sequence
<220> FEATURE:
<223> OTHER INFORMATION: Synthetic hsa-miR-212-4373087

<400> SEQUENCE: 124
uaacagucuc cagucacggc c                                             21

<210> SEQ ID NO 125
<211> LENGTH: 22
<212> TYPE: RNA
<213> ORGANISM: Artificial Sequence
<220> FEATURE:
<223> OTHER INFORMATION: Synthetic hsa-miR-213-000516

<400> SEQUENCE: 125
accaucgacc guugauugua cc                                            22

<210> SEQ ID NO 126
<211> LENGTH: 22
<212> TYPE: RNA
<213> ORGANISM: Artificial Sequence
<220> FEATURE:
<223> OTHER INFORMATION: Synthetic hsa-miR-21-4373090

<400> SEQUENCE: 126
uagcuuauca gacugauguu ga                                            22

<210> SEQ ID NO 127
<211> LENGTH: 23
<212> TYPE: RNA
<213> ORGANISM: Artificial Sequence
<220> FEATURE:
<223> OTHER INFORMATION: Synthetic hsa-miR-217-4395448

<400> SEQUENCE: 127
uacugcauca ggaacugauu gga                                           23

<210> SEQ ID NO 128
<211> LENGTH: 21
<212> TYPE: RNA
<213> ORGANISM: Artificial Sequence
<220> FEATURE:
<223> OTHER INFORMATION: Synthetic hsa-miR-218-4373081

<400> SEQUENCE: 128
uugugcuuga ucuaaccaug u                                             21

<210> SEQ ID NO 129
<211> LENGTH: 22
<212> TYPE: RNA
<213> ORGANISM: Artificial Sequence
<220> FEATURE:
<223> OTHER INFORMATION: Synthetic hsa-miR-219-2-3p-4395501

<400> SEQUENCE: 129
```
agaauugugg cuggacaucu gu                                              22

<210> SEQ ID NO 130
<211> LENGTH: 22
<212> TYPE: RNA
<213> ORGANISM: Artificial Sequence
<220> FEATURE:
<223> OTHER INFORMATION: Synthetic hsa-miR-22#-002301

<400> SEQUENCE: 130
aguucuucag uggcaagcuu ua                                              22

<210> SEQ ID NO 131
<211> LENGTH: 21
<212> TYPE: RNA
<213> ORGANISM: Artificial Sequence
<220> FEATURE:
<223> OTHER INFORMATION: Synthetic hsa-miR-220b-4395317

<400> SEQUENCE: 131
ccaccaccgu gucugacacu u                                               21

<210> SEQ ID NO 132
<211> LENGTH: 22
<212> TYPE: RNA
<213> ORGANISM: Artificial Sequence
<220> FEATURE:
<223> OTHER INFORMATION: Synthetic hsa-miR-222#-002097

<400> SEQUENCE: 132
cucaguagcc aguguagauc cu                                              22

<210> SEQ ID NO 133
<211> LENGTH: 22
<212> TYPE: RNA
<213> ORGANISM: Artificial Sequence
<220> FEATURE:
<223> OTHER INFORMATION: Synthetic hsa-miR-223-4395406

<400> SEQUENCE: 133
ugucaguuug ucaaauaccc ca                                              22

<210> SEQ ID NO 134
<211> LENGTH: 21
<212> TYPE: RNA
<213> ORGANISM: Artificial Sequence
<220> FEATURE:
<223> OTHER INFORMATION: Synthetic hsa-miR-23a-4373074

<400> SEQUENCE: 134
aucacauugc cagggauuuc c                                               21

<210> SEQ ID NO 135
<211> LENGTH: 22
<212> TYPE: RNA
<213> ORGANISM: Artificial Sequence
<220> FEATURE:
<223> OTHER INFORMATION: Synthetic hsa-miR-24-1#-002440

<400> SEQUENCE: 135
ugccuacuga gcugauauca gu                                              22

<210> SEQ ID NO 136
<211> LENGTH: 22
<212> TYPE: RNA

```
<213> ORGANISM: Artificial Sequence
<220> FEATURE:
<223> OTHER INFORMATION: Synthetic hsa-miR-25-4373071

<400> SEQUENCE: 136
cauugcacuu gucucggucu ga                                              22

<210> SEQ ID NO 137
<211> LENGTH: 22
<212> TYPE: RNA
<213> ORGANISM: Artificial Sequence
<220> FEATURE:
<223> OTHER INFORMATION: Synthetic hsa-miR-26a-2#-002115

<400> SEQUENCE: 137
ccuauucuug auuacuuguu uc                                              22

<210> SEQ ID NO 138
<211> LENGTH: 22
<212> TYPE: RNA
<213> ORGANISM: Artificial Sequence
<220> FEATURE:
<223> OTHER INFORMATION: Synthetic hsa-miR-26b#-002444

<400> SEQUENCE: 138
ccuguucucc auuacuuggc uc                                              22

<210> SEQ ID NO 139
<211> LENGTH: 22
<212> TYPE: RNA
<213> ORGANISM: Artificial Sequence
<220> FEATURE:
<223> OTHER INFORMATION: Synthetic hsa-miR-27a#-002445

<400> SEQUENCE: 139
agggcuuagc ugcuugugag ca                                              22

<210> SEQ ID NO 140
<211> LENGTH: 21
<212> TYPE: RNA
<213> ORGANISM: Artificial Sequence
<220> FEATURE:
<223> OTHER INFORMATION: Synthetic hsa-miR-27b-4373068

<400> SEQUENCE: 140
uucacagugg cuaaguucug c                                               21

<210> SEQ ID NO 141
<211> LENGTH: 22
<212> TYPE: RNA
<213> ORGANISM: Artificial Sequence
<220> FEATURE:
<223> OTHER INFORMATION: Synthetic hsa-miR-28-3p-4395557

<400> SEQUENCE: 141
cacuagauug ugagcuccug ga                                              22

<210> SEQ ID NO 142
<211> LENGTH: 22
<212> TYPE: RNA
<213> ORGANISM: Artificial Sequence
<220> FEATURE:
<223> OTHER INFORMATION: Synthetic hsa-miR-296-3p-4395212

<400> SEQUENCE: 142
gaggguuggg uggaggcucu cc                                              22
```

<210> SEQ ID NO 143
<211> LENGTH: 21
<212> TYPE: RNA
<213> ORGANISM: Artificial Sequence
<220> FEATURE:
<223> OTHER INFORMATION: Synthetic hsa-miR-296-5p-4373066

<400> SEQUENCE: 143 agggccccc cucaauccug u                                      21

<210> SEQ ID NO 144
<211> LENGTH: 22
<212> TYPE: RNA
<213> ORGANISM: Artificial Sequence
<220> FEATURE:
<223> OTHER INFORMATION: Synthetic hsa-miR-29a#-002447

<400> SEQUENCE: 144
acugauuucu uuggguguuc ag                                    22

<210> SEQ ID NO 145
<211> LENGTH: 22
<212> TYPE: RNA
<213> ORGANISM: Artificial Sequence
<220> FEATURE:
<223> OTHER INFORMATION: Synthetic hsa-miR-29a-4395223

<400> SEQUENCE: 145
uagcaccauc ugaaaucggu ua                                    22

<210> SEQ ID NO 146
<211> LENGTH: 22
<212> TYPE: RNA
<213> ORGANISM: Artificial Sequence
<220> FEATURE:
<223> OTHER INFORMATION: Synthetic hsa-miR-29c-4395171

<400> SEQUENCE: 146
uagcaccauu ugaaaucggu ua                                    22

<210> SEQ ID NO 147
<211> LENGTH: 23
<212> TYPE: RNA
<213> ORGANISM: Artificial Sequence
<220> FEATURE:
<223> OTHER INFORMATION: Synthetic hsa-miR-302a-4378070

<400> SEQUENCE: 147
uaagugcuuc cauguuuugg uga                                   23

<210> SEQ ID NO 148
<211> LENGTH: 23
<212> TYPE: RNA
<213> ORGANISM: Artificial Sequence
<220> FEATURE:
<223> OTHER INFORMATION: Synthetic hsa-miR-302d-000535

<400> SEQUENCE: 148
uaagugcuuc cauguuugag ugu                                   23

<210> SEQ ID NO 149
<211> LENGTH: 22
<212> TYPE: RNA
<213> ORGANISM: Artificial Sequence
<220> FEATURE:

<223> OTHER INFORMATION: Synthetic hsa-miR-30a-3p-000416

<400> SEQUENCE: 149
cuuucagucg gauguuugca gc                                                    22

<210> SEQ ID NO 150
<211> LENGTH: 22
<212> TYPE: RNA
<213> ORGANISM: Artificial Sequence
<220> FEATURE:
<223> OTHER INFORMATION: Synthetic hsa-miR-30b-4373290

<400> SEQUENCE: 150
uguaaacauc cuacacucag cu                                                    22

<210> SEQ ID NO 151
<211> LENGTH: 22
<212> TYPE: RNA
<213> ORGANISM: Artificial Sequence
<220> FEATURE:
<223> OTHER INFORMATION: Synthetic hsa-miR-30c-1#-002108

<400> SEQUENCE: 151
cugggagagg guuguuuacu cc                                                    22

<210> SEQ ID NO 152
<211> LENGTH: 22
<212> TYPE: RNA
<213> ORGANISM: Artificial Sequence
<220> FEATURE:
<223> OTHER INFORMATION: Synthetic hsa-miR-30e-3p-000422

<400> SEQUENCE: 152
cuuucagucg gauguuuaca gc                                                    22

<210> SEQ ID NO 153
<211> LENGTH: 22
<212> TYPE: RNA
<213> ORGANISM: Artificial Sequence
<220> FEATURE:
<223> OTHER INFORMATION: Synthetic hsa-miR-31#-002113

<400> SEQUENCE: 153
ugcuaugcca acauauugcc au                                                    22

<210> SEQ ID NO 154
<211> LENGTH: 21
<212> TYPE: RNA
<213> ORGANISM: Artificial Sequence
<220> FEATURE:
<223> OTHER INFORMATION: Synthetic hsa-miR-31-4395390

<400> SEQUENCE: 154
aggcaagaug cuggcauagc u                                                     21

<210> SEQ ID NO 155
<211> LENGTH: 22
<212> TYPE: RNA
<213> ORGANISM: Artificial Sequence
<220> FEATURE:
<223> OTHER INFORMATION: Synthetic hsa-miR-320B-002844

<400> SEQUENCE: 155
aaaagcuggg uugagagggc aa                                                    22

```
<210> SEQ ID NO 156
<211> LENGTH: 23
<212> TYPE: RNA
<213> ORGANISM: Artificial Sequence
<220> FEATURE:
<223> OTHER INFORMATION: Synthetic hsa-miR-324-5p-4373052

<400> SEQUENCE: 156
cgcauccccu agggcauugg ugu                                              23

<210> SEQ ID NO 157
<211> LENGTH: 20
<212> TYPE: RNA
<213> ORGANISM: Artificial Sequence
<220> FEATURE:
<223> OTHER INFORMATION: Synthetic hsa-miR-326-4373050

<400> SEQUENCE: 157
ccucugggcc cuuccuccag                                                  20

<210> SEQ ID NO 158
<211> LENGTH: 22
<212> TYPE: RNA
<213> ORGANISM: Artificial Sequence
<220> FEATURE:
<223> OTHER INFORMATION: Synthetic hsa-miR-328-4373049

<400> SEQUENCE: 158
cuggcccucu cugcccuucc gu                                               22

<210> SEQ ID NO 159
<211> LENGTH: 22
<212> TYPE: RNA
<213> ORGANISM: Artificial Sequence
<220> FEATURE:
<223> OTHER INFORMATION: Synthetic hsa-miR-330-5p-4395341

<400> SEQUENCE: 159
ucucugggcc ugugucuuag gc                                               22

<210> SEQ ID NO 160
<211> LENGTH: 22
<212> TYPE: RNA
<213> ORGANISM: Artificial Sequence
<220> FEATURE:
<223> OTHER INFORMATION: Synthetic hsa-miR-337-3p-002157

<400> SEQUENCE: 160
cuccuauaug augccuuucu uc                                               22

<210> SEQ ID NO 161
<211> LENGTH: 22
<212> TYPE: RNA
<213> ORGANISM: Artificial Sequence
<220> FEATURE:
<223> OTHER INFORMATION: Synthetic hsa-miR-338-3p-4395363

<400> SEQUENCE: 161
uccagcauca gugauuuugu ug                                               22

<210> SEQ ID NO 162
<211> LENGTH: 23
<212> TYPE: RNA
<213> ORGANISM: Artificial Sequence
<220> FEATURE:
<223> OTHER INFORMATION: Synthetic hsa-miR-339-5p-4395368
```

```
<400> SEQUENCE: 162
ucccuguccu ccaggagcuc acg                                              23

<210> SEQ ID NO 163
<211> LENGTH: 20
<212> TYPE: RNA
<213> ORGANISM: Artificial Sequence
<220> FEATURE:
<223> OTHER INFORMATION: Synthetic hsa-miR-33b-4395196

<400> SEQUENCE: 163
gugcauugcu guugcauugc                                                  20

<210> SEQ ID NO 164
<211> LENGTH: 22
<212> TYPE: RNA
<213> ORGANISM: Artificial Sequence
<220> FEATURE:
<223> OTHER INFORMATION: Synthetic hsa-miR-340#-002259

<400> SEQUENCE: 164
uccgucucag uuacuuuaua gc                                               22

<210> SEQ ID NO 165
<211> LENGTH: 22
<212> TYPE: RNA
<213> ORGANISM: Artificial Sequence
<220> FEATURE:
<223> OTHER INFORMATION: Synthetic hsa-miR-340-4395369

<400> SEQUENCE: 165
uuauaaagca augagacuga uu                                               22

<210> SEQ ID NO 166
<211> LENGTH: 22
<212> TYPE: RNA
<213> ORGANISM: Artificial Sequence
<220> FEATURE:
<223> OTHER INFORMATION: Synthetic hsa-miR-345-4395297

<400> SEQUENCE: 166
gcugacuccu aguccagggc uc                                               22

<210> SEQ ID NO 167
<211> LENGTH: 22
<212> TYPE: RNA
<213> ORGANISM: Artificial Sequence
<220> FEATURE:
<223> OTHER INFORMATION: Synthetic hsa-miR-34a#-002316

<400> SEQUENCE: 167
caaucagcaa guauacugcc cu                                               22

<210> SEQ ID NO 168
<211> LENGTH: 22
<212> TYPE: RNA
<213> ORGANISM: Artificial Sequence
<220> FEATURE:
<223> OTHER INFORMATION: Synthetic hsa-miR-34a-4395168

<400> SEQUENCE: 168
uggcaguguc uuagcugguu gu                                               22

<210> SEQ ID NO 169
<211> LENGTH: 23
```

```
<212> TYPE: RNA
<213> ORGANISM: Artificial Sequence
<220> FEATURE:
<223> OTHER INFORMATION: Synthetic hsa-miR-34b-000427

<400> SEQUENCE: 169
uaggcagugu cauuagcuga uug                                          23

<210> SEQ ID NO 170
<211> LENGTH: 23
<212> TYPE: RNA
<213> ORGANISM: Artificial Sequence
<220> FEATURE:
<223> OTHER INFORMATION: Synthetic hsa-miR-34c-5p-4373036

<400> SEQUENCE: 170
aggcagugua guuagcugau ugc                                          23

<210> SEQ ID NO 171
<211> LENGTH: 24
<212> TYPE: RNA
<213> ORGANISM: Artificial Sequence
<220> FEATURE:
<223> OTHER INFORMATION: Synthetic hsa-miR-362-5p-4378092

<400> SEQUENCE: 171
aauccuugga accuaggugu gagu                                         24

<210> SEQ ID NO 172
<211> LENGTH: 22
<212> TYPE: RNA
<213> ORGANISM: Artificial Sequence
<220> FEATURE:
<223> OTHER INFORMATION: Synthetic hsa-miR-363#-001283

<400> SEQUENCE: 172
cggguggauc acgaugcaau uu                                           22

<210> SEQ ID NO 173
<211> LENGTH: 22
<212> TYPE: RNA
<213> ORGANISM: Artificial Sequence
<220> FEATURE:
<223> OTHER INFORMATION: Synthetic hsa-miR-363-4378090

<400> SEQUENCE: 173
aauugcacgg uauccaucug ua                                           22

<210> SEQ ID NO 174
<211> LENGTH: 22
<212> TYPE: RNA
<213> ORGANISM: Artificial Sequence
<220> FEATURE:
<223> OTHER INFORMATION: Synthetic hsa-miR-365-4373194

<400> SEQUENCE: 174
uaaugcsccu aaaaauccuu au                                           22

<210> SEQ ID NO 175
<211> LENGTH: 22
<212> TYPE: RNA
<213> ORGANISM: Artificial Sequence
<220> FEATURE:
<223> OTHER INFORMATION: Synthetic hsa-miR-367-4373034

<400> SEQUENCE: 175
```
aauugcacuu uagcaauggu ga                                                  22

<210> SEQ ID NO 176
<211> LENGTH: 23
<212> TYPE: RNA
<213> ORGANISM: Artificial Sequence
<220> FEATURE:
<223> OTHER INFORMATION: Synthetic hsa-miR-373-4378073

<400> SEQUENCE: 176
gaagugcuuc gauuuugggg ugu                                                 23

<210> SEQ ID NO 177
<211> LENGTH: 22
<212> TYPE: RNA
<213> ORGANISM: Artificial Sequence
<220> FEATURE:
<223> OTHER INFORMATION: Synthetic hsa-miR-374b#-002391

<400> SEQUENCE: 177
cuuagcaggu uguauuauca uu                                                  22

<210> SEQ ID NO 178
<211> LENGTH: 22
<212> TYPE: RNA
<213> ORGANISM: Artificial Sequence
<220> FEATURE:
<223> OTHER INFORMATION: Synthetic hsa-miR-374b-4381045

<400> SEQUENCE: 178
auauaauaca accugcuaag ug                                                  22

<210> SEQ ID NO 179
<211> LENGTH: 21
<212> TYPE: RNA
<213> ORGANISM: Artificial Sequence
<220> FEATURE:
<223> OTHER INFORMATION: Synthetic hsa-miR-376c-4395233

<400> SEQUENCE: 179
aacauagagg aaauuccacg u                                                   21

<210> SEQ ID NO 180
<211> LENGTH: 22
<212> TYPE: RNA
<213> ORGANISM: Artificial Sequence
<220> FEATURE:
<223> OTHER INFORMATION: Synthetic hsa-miR-378-000567

<400> SEQUENCE: 180
cuccugacuc cagguccugu gu                                                  22

<210> SEQ ID NO 181
<211> LENGTH: 22
<212> TYPE: RNA
<213> ORGANISM: Artificial Sequence
<220> FEATURE:
<223> OTHER INFORMATION: Synthetic hsa-miR-380-5p-000570

<400> SEQUENCE: 181
ugguugacca uagaacaugc gc                                                  22

<210> SEQ ID NO 182
<211> LENGTH: 22
<212> TYPE: RNA
<213> ORGANISM: Artificial Sequence

```
<220> FEATURE:
<223> OTHER INFORMATION: Synthetic hsa-miR-381-4373020

<400> SEQUENCE: 182
uauacaaggg caagcucucu gu                                              22

<210> SEQ ID NO 183
<211> LENGTH: 22
<212> TYPE: RNA
<213> ORGANISM: Artificial Sequence
<220> FEATURE:
<223> OTHER INFORMATION: Synthetic hsa-miR-382-4373019

<400> SEQUENCE: 183
gaaguuguuc gugguggauu cg                                              22

<210> SEQ ID NO 184
<211> LENGTH: 22
<212> TYPE: RNA
<213> ORGANISM: Artificial Sequence
<220> FEATURE:
<223> OTHER INFORMATION: Synthetic hsa-miR-383-4373018

<400> SEQUENCE: 184
agaucagaag gugauugugg cu                                              22

<210> SEQ ID NO 185
<211> LENGTH: 22
<212> TYPE: RNA
<213> ORGANISM: Artificial Sequence
<220> FEATURE:
<223> OTHER INFORMATION: Synthetic hsa-miR-409-3p-002332

<400> SEQUENCE: 185
gaauguugcu cggugaaccc cu                                              22

<210> SEQ ID NO 186
<211> LENGTH: 21
<212> TYPE: RNA
<213> ORGANISM: Artificial Sequence
<220> FEATURE:
<223> OTHER INFORMATION: Synthetic hsa-miR-411-4381013

<400> SEQUENCE: 186
uaguagaccg uauagcguac g                                               21

<210> SEQ ID NO 187
<211> LENGTH: 21
<212> TYPE: RNA
<213> ORGANISM: Artificial Sequence
<220> FEATURE:
<223> OTHER INFORMATION: Synthetic hsa-miR-424#-002309

<400> SEQUENCE: 187
caaaacguga ggcgcugcua u                                               21

<210> SEQ ID NO 188
<211> LENGTH: 22
<212> TYPE: RNA
<213> ORGANISM: Artificial Sequence
<220> FEATURE:
<223> OTHER INFORMATION: Synthetic hsa-miR-424-4373201

<400> SEQUENCE: 188
cagcagcaau ucauguuuug aa                                              22
```

```
<210> SEQ ID NO 189
<211> LENGTH: 21
<212> TYPE: RNA
<213> ORGANISM: Artificial Sequence
<220> FEATURE:
<223> OTHER INFORMATION: Synthetic hsa-miR-431-4395173

<400> SEQUENCE: 189
ugucuugcag gccgucaugc a                                              21

<210> SEQ ID NO 190
<211> LENGTH: 23
<212> TYPE: RNA
<213> ORGANISM: Artificial Sequence
<220> FEATURE:
<223> OTHER INFORMATION: Synthetic hsa-miR-432-001026

<400> SEQUENCE: 190
ucuuggagua ggucauuggg ugg                                            23

<210> SEQ ID NO 191
<211> LENGTH: 22
<212> TYPE: RNA
<213> ORGANISM: Artificial Sequence
<220> FEATURE:
<223> OTHER INFORMATION: Synthetic hsa-miR-448-4373206

<400> SEQUENCE: 191
uugcauaugu aggauguccc au                                             22

<210> SEQ ID NO 192
<211> LENGTH: 22
<212> TYPE: RNA
<213> ORGANISM: Artificial Sequence
<220> FEATURE:
<223> OTHER INFORMATION: Synthetic hsa-miR-449b-4381011

<400> SEQUENCE: 192
aggcagugua uuguuagcug gc                                             22

<210> SEQ ID NO 193
<211> LENGTH: 22
<212> TYPE: RNA
<213> ORGANISM: Artificial Sequence
<220> FEATURE:
<223> OTHER INFORMATION: Synthetic hsa-miR-450a-4395414

<400> SEQUENCE: 193
uuuugcgaug uguuccuaau au                                             22

<210> SEQ ID NO 194
<211> LENGTH: 23
<212> TYPE: RNA
<213> ORGANISM: Artificial Sequence
<220> FEATURE:
<223> OTHER INFORMATION: Synthetic hsa-miR-454-4395434

<400> SEQUENCE: 194
uagugcaaua uugcuuauag ggu                                            23

<210> SEQ ID NO 195
<211> LENGTH: 21
<212> TYPE: RNA
<213> ORGANISM: Artificial Sequence
<220> FEATURE:
<223> OTHER INFORMATION: Synthetic hsa-miR-483-3p-002339
```

-continued

<400> SEQUENCE: 195
ucacuccucu ccucccgucu u                                             21

<210> SEQ ID NO 196
<211> LENGTH: 22
<212> TYPE: RNA
<213> ORGANISM: Artificial Sequence
<220> FEATURE:
<223> OTHER INFORMATION: Synthetic hsa-miR-484-4381032

<400> SEQUENCE: 196
ucaggcucag uccccucccg au                                            22

<210> SEQ ID NO 197
<211> LENGTH: 22
<212> TYPE: RNA
<213> ORGANISM: Artificial Sequence
<220> FEATURE:
<223> OTHER INFORMATION: Synthetic hsa-miR-486-5p-4378096

<400> SEQUENCE: 197
uccuguacug agcugccccg ag                                            22

<210> SEQ ID NO 198
<211> LENGTH: 21
<212> TYPE: RNA
<213> ORGANISM: Artificial Sequence
<220> FEATURE:
<223> OTHER INFORMATION: Synthetic hsa-miR-488-4395468

<400> SEQUENCE: 198
uugaaaggcu auuucuuggu c                                             21

<210> SEQ ID NO 199
<211> LENGTH: 22
<212> TYPE: RNA
<213> ORGANISM: Artificial Sequence
<220> FEATURE:
<223> OTHER INFORMATION: Synthetic hsa-miR-489-4395469

<400> SEQUENCE: 199
gugacaucac auauacggca gc                                            22

<210> SEQ ID NO 200
<211> LENGTH: 21
<212> TYPE: RNA
<213> ORGANISM: Artificial Sequence
<220> FEATURE:
<223> OTHER INFORMATION: Synthetic hsa-miR-497-001043

<400> SEQUENCE: 200
cagcagcaca cugugguuug u                                             21

<210> SEQ ID NO 201
<211> LENGTH: 23
<212> TYPE: RNA
<213> ORGANISM: Artificial Sequence
<220> FEATURE:
<223> OTHER INFORMATION: Synthetic hsa-miR-499-5p-4381047

<400> SEQUENCE: 201
uuaagacuug cagugauguu uaa                                           23

<210> SEQ ID NO 202

```
<211> LENGTH: 22
<212> TYPE: RNA
<213> ORGANISM: Artificial Sequence
<220> FEATURE:
<223> OTHER INFORMATION: Synthetic hsa-miR-500-001046

<400> SEQUENCE: 202
augcaccugg gcaaggauuc ug                                                  22

<210> SEQ ID NO 203
<211> LENGTH: 21
<212> TYPE: RNA
<213> ORGANISM: Artificial Sequence
<220> FEATURE:
<223> OTHER INFORMATION: Synthetic hsa-miR-511-4373236

<400> SEQUENCE: 203
gugucuuuug cucugcaguc a                                                   21

<210> SEQ ID NO 204
<211> LENGTH: 18
<212> TYPE: RNA
<213> ORGANISM: Artificial Sequence
<220> FEATURE:
<223> OTHER INFORMATION: Synthetic hsa-miR-516-3p-001149

<400> SEQUENCE: 204
ugcuuccuuu cagagggu                                                       18

<210> SEQ ID NO 205
<211> LENGTH: 22
<212> TYPE: RNA
<213> ORGANISM: Artificial Sequence
<220> FEATURE:
<223> OTHER INFORMATION: Synthetic hsa-miR-516b-4395172

<400> SEQUENCE: 205
aucuggaggu aagaagcacu uu                                                  22

<210> SEQ ID NO 206
<211> LENGTH: 22
<212> TYPE: RNA
<213> ORGANISM: Artificial Sequence
<220> FEATURE:
<223> OTHER INFORMATION: Synthetichsa-miR-517#-001113

<400> SEQUENCE: 206
ccucuagaug gaagcacugu cu                                                  22

<210> SEQ ID NO 207
<211> LENGTH: 22
<212> TYPE: RNA
<213> ORGANISM: Artificial Sequence
<220> FEATURE:
<223> OTHER INFORMATION: Synthetic hsa-miR-518a-3p-4395508

<400> SEQUENCE: 207
gaaagcgcuu cccuuugcug ga                                                  22

<210> SEQ ID NO 208
<211> LENGTH: 22
<212> TYPE: RNA
<213> ORGANISM: Artificial Sequence
<220> FEATURE:
<223> OTHER INFORMATION: Synthetic hsa-miR-518b-4373246

<400> SEQUENCE: 208
```

```
caaagcgcuc cccuuuagag gu                                          22
```

<210> SEQ ID NO 209
<211> LENGTH: 22
<212> TYPE: RNA
<213> ORGANISM: Artificial Sequence
<220> FEATURE:
<223> OTHER INFORMATION: Synthetic hsa-miR-519a-4395526

<400> SEQUENCE: 209

```
aaagugcauc cuuuagagu gu                                           22
```

<210> SEQ ID NO 210
<211> LENGTH: 22
<212> TYPE: RNA
<213> ORGANISM: Artificial Sequence
<220> FEATURE:
<223> OTHER INFORMATION: Synthetic hsa-miR-520c-3p-002400

<400> SEQUENCE: 210

```
aaagugcuuc cuuuagagg gu                                           22
```

<210> SEQ ID NO 211
<211> LENGTH: 22
<212> TYPE: RNA
<213> ORGANISM: Artificial Sequence
<220> FEATURE:
<223> OTHER INFORMATION: Synthetic hsa-miR-520D-3P-002743

<400> SEQUENCE: 211

```
aaagugcuuc ucuuuggugg gu                                          22
```

<210> SEQ ID NO 212
<211> LENGTH: 24
<212> TYPE: RNA
<213> ORGANISM: Artificial Sequence
<220> FEATURE:
<223> OTHER INFORMATION: Synthetic hsa-miR-520g-4373257

<400> SEQUENCE: 212

```
acaaagugcu ucccuuuaga gugu                                        24
```

<210> SEQ ID NO 213
<211> LENGTH: 22
<212> TYPE: RNA
<213> ORGANISM: Artificial Sequence
<220> FEATURE:
<223> OTHER INFORMATION: Synthetic hsa-miR-521-4373259

<400> SEQUENCE: 213

```
aacgcacuuc ccuuuagagu gu                                          22
```

<210> SEQ ID NO 214
<211> LENGTH: 22
<212> TYPE: RNA
<213> ORGANISM: Artificial Sequence
<220> FEATURE:
<223> OTHER INFORMATION: Synthetic hsa-miR-539-4378103

<400> SEQUENCE: 214

```
ggagaaauua uccuuggugu gu                                          22
```

<210> SEQ ID NO 215
<211> LENGTH: 22
<212> TYPE: RNA

```
<213> ORGANISM: Artificial Sequence
<220> FEATURE:
<223> OTHER INFORMATION: Synthetic hsa-miR-541-4395312

<400> SEQUENCE: 215
uggugggcac agaaucugga cu                                              22

<210> SEQ ID NO 216
<211> LENGTH: 22
<212> TYPE: RNA
<213> ORGANISM: Artificial Sequence
<220> FEATURE:
<223> OTHER INFORMATION: Synthetic hsa-miR-543-002376

<400> SEQUENCE: 216
aaacauucgc ggugcacuuc uu                                              22

<210> SEQ ID NO 217
<211> LENGTH: 22
<212> TYPE: RNA
<213> ORGANISM: Artificial Sequence
<220> FEATURE:
<223> OTHER INFORMATION: Synthetic hsa-miR-545-4395378

<400> SEQUENCE: 217
ucagcaaaca uuuauugugu gc                                              22

<210> SEQ ID NO 218
<211> LENGTH: 22
<212> TYPE: RNA
<213> ORGANISM: Artificial Sequence
<220> FEATURE:
<223> OTHER INFORMATION: Synthetic hsa-miR-548b-5p-4395519

<400> SEQUENCE: 218
aaaaguaauu gugguuuugg cc                                              22

<210> SEQ ID NO 219
<211> LENGTH: 22
<212> TYPE: RNA
<213> ORGANISM: Artificial Sequence
<220> FEATURE:
<223> OTHER INFORMATION: Synthetic hsa-miR-548c-5p-4395540

<400> SEQUENCE: 219
aaaaguaauu gcgguuuuug cc                                              22

<210> SEQ ID NO 220
<211> LENGTH: 22
<212> TYPE: RNA
<213> ORGANISM: Artificial Sequence
<220> FEATURE:
<223> OTHER INFORMATION: Synthetic hsa-miR-548I-002909

<400> SEQUENCE: 220
aaaaguaauu gcggauuuug cc                                              22

<210> SEQ ID NO 221
<211> LENGTH: 22
<212> TYPE: RNA
<213> ORGANISM: Artificial Sequence
<220> FEATURE:
<223> OTHER INFORMATION: Synthetic hsa-miR-551b#-002346

<400> SEQUENCE: 221
gaaaucaagc gugggugaga cc                                              22
```

```
<210> SEQ ID NO 222
<211> LENGTH: 21
<212> TYPE: RNA
<213> ORGANISM: Artificial Sequence
<220> FEATURE:
<223> OTHER INFORMATION: Synthetic hsa-miR-552-001520

<400> SEQUENCE: 222
aacaggugac ugguuagaca a                                             21

<210> SEQ ID NO 223
<211> LENGTH: 21
<212> TYPE: RNA
<213> ORGANISM: Artificial Sequence
<220> FEATURE:
<223> OTHER INFORMATION: Synthetic hsa-miR-559-001527

<400> SEQUENCE: 223
uaaaguaaau augcaccaaa a                                             21

<210> SEQ ID NO 224
<211> LENGTH: 19
<212> TYPE: RNA
<213> ORGANISM: Artificial Sequence
<220> FEATURE:
<223> OTHER INFORMATION: Synthetic hsa-miR-566-001533

<400> SEQUENCE: 224
gggcgccugu gaucccaac                                                19

<210> SEQ ID NO 225
<211> LENGTH: 21
<212> TYPE: RNA
<213> ORGANISM: Artificial Sequence
<220> FEATURE:
<223> OTHER INFORMATION: Synthetic hsa-miR-571-001613

<400> SEQUENCE: 225
ugaguuggcc aucugaguga g                                             21

<210> SEQ ID NO 226
<211> LENGTH: 22
<212> TYPE: RNA
<213> ORGANISM: Artificial Sequence
<220> FEATURE:
<223> OTHER INFORMATION: Synthetic hsa-miR-574-3p-4395460

<400> SEQUENCE: 226
cacgcucaug cacacaccca ca                                            22

<210> SEQ ID NO 227
<211> LENGTH: 21
<212> TYPE: RNA
<213> ORGANISM: Artificial Sequence
<220> FEATURE:
<223> OTHER INFORMATION: Synthetic hsa-miR-577-002675

<400> SEQUENCE: 227
uagauaaaau auugguaccu g                                             21

<210> SEQ ID NO 228
<211> LENGTH: 22
<212> TYPE: RNA
<213> ORGANISM: Artificial Sequence
<220> FEATURE:
```

```
<223> OTHER INFORMATION: Synthetic hsa-miR-582-3p-4395510

<400> SEQUENCE: 228
uaacugguug aacaacugaa cc                                              22

<210> SEQ ID NO 229
<211> LENGTH: 24
<212> TYPE: RNA
<213> ORGANISM: Artificial Sequence
<220> FEATURE:
<223> OTHER INFORMATION: Synthetic hsa-miR-589-001543

<400> SEQUENCE: 229
ucagaacaaa ugccgguucc caga                                            24

<210> SEQ ID NO 230
<211> LENGTH: 21
<212> TYPE: RNA
<213> ORGANISM: Artificial Sequence
<220> FEATURE:
<223> OTHER INFORMATION: Synthetic hsa-miR-590-3P-002677

<400> SEQUENCE: 230
uaauuuuaug uauaagcuag u                                               21

<210> SEQ ID NO 231
<211> LENGTH: 22
<212> TYPE: RNA
<213> ORGANISM: Artificial Sequence
<220> FEATURE:
<223> OTHER INFORMATION: Synthetic hsa-miR-590-5p-4395176

<400> SEQUENCE: 231
gagcuuauuc auaaaagugc ag                                              22

<210> SEQ ID NO 232
<211> LENGTH: 22
<212> TYPE: RNA
<213> ORGANISM: Artificial Sequence
<220> FEATURE:
<223> OTHER INFORMATION: Synthetic hsa-miR-592-001546

<400> SEQUENCE: 232
uugugucaau augcgaugau gu                                              22

<210> SEQ ID NO 233
<211> LENGTH: 25
<212> TYPE: RNA
<213> ORGANISM: Artificial Sequence
<220> FEATURE:
<223> OTHER INFORMATION: Synthetic hsa-miR-593-001547

<400> SEQUENCE: 233
aggcaccagc caggcauugc ucagc                                           25

<210> SEQ ID NO 234
<211> LENGTH: 22
<212> TYPE: RNA
<213> ORGANISM: Artificial Sequence
<220> FEATURE:
<223> OTHER INFORMATION: Synthetic hsa-miR-597-4380960

<400> SEQUENCE: 234
ugugucacuc gaugaccacu gu                                              22
```

```
<210> SEQ ID NO 235
<211> LENGTH: 22
<212> TYPE: RNA
<213> ORGANISM: Artificial Sequence
<220> FEATURE:
<223> OTHER INFORMATION: Synthetic hsa-miR-601-001558

<400> SEQUENCE: 235
uggucuagga uuguuggagg ag                                                   22

<210> SEQ ID NO 236
<211> LENGTH: 19
<212> TYPE: RNA
<213> ORGANISM: Artificial Sequence
<220> FEATURE:
<223> OTHER INFORMATION: Synthetic hsa-miR-604-001567

<400> SEQUENCE: 236
aggcugcgga auucaggac                                                      19

<210> SEQ ID NO 237
<211> LENGTH: 25
<212> TYPE: RNA
<213> ORGANISM: Artificial Sequence
<220> FEATURE:
<223> OTHER INFORMATION: Synthetic hsa-miR-608-001571

<400> SEQUENCE: 237 aggggguggug uugggacagc uccgu                                              25

<210> SEQ ID NO 238
<211> LENGTH: 22
<212> TYPE: RNA
<213> ORGANISM: Artificial Sequence
<220> FEATURE:
<223> OTHER INFORMATION: Synthetic hsa-miR-616-4395525

<400> SEQUENCE: 238
agucauugga ggguuugagc ag                                                   22

<210> SEQ ID NO 239
<211> LENGTH: 22
<212> TYPE: RNA
<213> ORGANISM: Artificial Sequence
<220> FEATURE:
<223> OTHER INFORMATION: Synthetic hsa-miR-617-001591

<400> SEQUENCE: 239
agacuuccca uuugaaggug gc                                                   22

<210> SEQ ID NO 240
<211> LENGTH: 23
<212> TYPE: RNA
<213> ORGANISM: Artificial Sequence
<220> FEATURE:
<223> OTHER INFORMATION: Synthetic hsa-miR-618-4380996

<400> SEQUENCE: 240
aaacucuacu uguccuucug agu                                                  23

<210> SEQ ID NO 241
<211> LENGTH: 21
<212> TYPE: RNA
<213> ORGANISM: Artificial Sequence
<220> FEATURE:
<223> OTHER INFORMATION: Synthetic hsa-miR-622-001553
```

```
<400> SEQUENCE: 241
acagucugcu gagguuggag c                                              21

<210> SEQ ID NO 242
<211> LENGTH: 22
<212> TYPE: RNA
<213> ORGANISM: Artificial Sequence
<220> FEATURE:
<223> OTHER INFORMATION: Synthetic hsa-miR-625#-002432

<400> SEQUENCE: 242
gacuauagaa cuuuccccu ca                                              22

<210> SEQ ID NO 243
<211> LENGTH: 19
<212> TYPE: RNA
<213> ORGANISM: Artificial Sequence
<220> FEATURE:
<223> OTHER INFORMATION: Synthetic hsa-miR-626-001559

<400> SEQUENCE: 243
agcugucuga aaaugucuu                                                 19

<210> SEQ ID NO 244
<211> LENGTH: 21
<212> TYPE: RNA
<213> ORGANISM: Artificial Sequence
<220> FEATURE:
<223> OTHER INFORMATION: Synthetic hsa-miR-628-3p-002434

<400> SEQUENCE: 244
ucuaguaaga guggcagucg a                                              21

<210> SEQ ID NO 245
<211> LENGTH: 22
<212> TYPE: RNA
<213> ORGANISM: Artificial Sequence
<220> FEATURE:
<223> OTHER INFORMATION: Synthetic hsa-miR-628-5p-4395544

<400> SEQUENCE: 245
augcugacau auuuacuaga gg                                             22

<210> SEQ ID NO 246
<211> LENGTH: 21
<212> TYPE: RNA
<213> ORGANISM: Artificial Sequence
<220> FEATURE:
<223> OTHER INFORMATION: Synthetic hsa-miR-629-001562

<400> SEQUENCE: 246
uggguuuacg uugggagaac u                                              21

<210> SEQ ID NO 247
<211> LENGTH: 22
<212> TYPE: RNA
<213> ORGANISM: Artificial Sequence
<220> FEATURE:
<223> OTHER INFORMATION: Synthetic hsa-miR-630-001563

<400> SEQUENCE: 247
aguauucugu accagggaag gu                                             22

<210> SEQ ID NO 248
<211> LENGTH: 23
```

```
<212> TYPE: RNA
<213> ORGANISM: Artificial Sequence
<220> FEATURE:
<223> OTHER INFORMATION: Synthetic hsa-miR-635-001578

<400> SEQUENCE: 248
acuugggcac ugaaacaaug ucc                                          23

<210> SEQ ID NO 249
<211> LENGTH: 25
<212> TYPE: RNA
<213> ORGANISM: Artificial Sequence
<220> FEATURE:
<223> OTHER INFORMATION: Synthetic hsa-miR-638-001582

<400> SEQUENCE: 249
agggaucgcg ggcggguggc ggccu                                        25

<210> SEQ ID NO 250
<211> LENGTH: 23
<212> TYPE: RNA
<213> ORGANISM: Artificial Sequence
<220> FEATURE:
<223> OTHER INFORMATION: Synthetic hsa-miR-639-001583

<400> SEQUENCE: 250
aucgcugcgg uugcgagcgc ugu                                          23

<210> SEQ ID NO 251
<211> LENGTH: 24
<212> TYPE: RNA
<213> ORGANISM: Artificial Sequence
<220> FEATURE:
<223> OTHER INFORMATION: Synthetic hsa-miR-641-001585

<400> SEQUENCE: 251
aaagacauag gauagaguca ccuc                                         24

<210> SEQ ID NO 252
<211> LENGTH: 19
<212> TYPE: RNA
<213> ORGANISM: Artificial Sequence
<220> FEATURE:
<223> OTHER INFORMATION: Synthetic hsa-miR-644-001596

<400> SEQUENCE: 252
aguguggcuu ucuuagagc                                               19

<210> SEQ ID NO 253
<211> LENGTH: 22
<212> TYPE: RNA
<213> ORGANISM: Artificial Sequence
<220> FEATURE:
<223> OTHER INFORMATION: Synthetic hsa-miR-649-001602

<400> SEQUENCE: 253
aaaccugugu uguucaagag uc                                           22

<210> SEQ ID NO 254
<211> LENGTH: 21
<212> TYPE: RNA
<213> ORGANISM: Artificial Sequence
<220> FEATURE:
<223> OTHER INFORMATION: Synthetic hsa-miR-652-4395463

<400> SEQUENCE: 254
```

-continued aauggcgcca cuaggguugu g                                       21

<210> SEQ ID NO 255
<211> LENGTH: 22
<212> TYPE: RNA
<213> ORGANISM: Artificial Sequence
<220> FEATURE:
<223> OTHER INFORMATION: Synthetic hsa-miR-654-3p-4395350

<400> SEQUENCE: 255
uaugucugcu gaccaucacc uu                                      22

<210> SEQ ID NO 256
<211> LENGTH: 22
<212> TYPE: RNA
<213> ORGANISM: Artificial Sequence
<220> FEATURE:
<223> OTHER INFORMATION: Synthetic hsa-miR-659-001514

<400> SEQUENCE: 256
cuugguucag ggagggcccc ca                                      22

<210> SEQ ID NO 257
<211> LENGTH: 22
<212> TYPE: RNA
<213> ORGANISM: Artificial Sequence
<220> FEATURE:
<223> OTHER INFORMATION: Synthetic hsa-miR-660-4380925

<400> SEQUENCE: 257
uacccauugc auacggagu ug                                       22

<210> SEQ ID NO 258
<211> LENGTH: 24
<212> TYPE: RNA
<213> ORGANISM: Artificial Sequence
<220> FEATURE:
<223> OTHER INFORMATION: Synthetic hsa-miR-661-001606

<400> SEQUENCE: 258
ugccuggguc ucuggccugc gcgu                                    24

<210> SEQ ID NO 259
<211> LENGTH: 22
<212> TYPE: RNA
<213> ORGANISM: Artificial Sequence
<220> FEATURE:
<223> OTHER INFORMATION: Synthetic hsa-miR-663B-002857

<400> SEQUENCE: 259
gguggcccgg ccgugccuga gg                                      22

<210> SEQ ID NO 260
<211> LENGTH: 23
<212> TYPE: RNA
<213> ORGANISM: Artificial Sequence
<220> FEATURE:
<223> OTHER INFORMATION: Synthetic hsa-miR-664-002897

<400> SEQUENCE: 260
uauucauuua uccccagccu aca                                     23

<210> SEQ ID NO 261
<211> LENGTH: 21
<212> TYPE: RNA
<213> ORGANISM: Artificial Sequence

```
<220> FEATURE:
<223> OTHER INFORMATION: Synthetic hsa-miR-671-3p-4395433

<400> SEQUENCE: 261
uccgguucuc agggcuccac c                                              21

<210> SEQ ID NO 262
<211> LENGTH: 23
<212> TYPE: RNA
<213> ORGANISM: Artificial Sequence
<220> FEATURE:
<223> OTHER INFORMATION: Synthetic hsa-miR-708-4395452

<400> SEQUENCE: 262
aaggagcuua caaucuagcu ggg                                            23

<210> SEQ ID NO 263
<211> LENGTH: 17
<212> TYPE: RNA
<213> ORGANISM: Artificial Sequence
<220> FEATURE:
<223> OTHER INFORMATION: Synthetic hsa-miR-720-002895

<400> SEQUENCE: 263
ucucgcuggg gccucca                                                   17

<210> SEQ ID NO 264
<211> LENGTH: 22
<212> TYPE: RNA
<213> ORGANISM: Artificial Sequence
<220> FEATURE:
<223> OTHER INFORMATION: Synthetic hsa-miR-758-4395180

<400> SEQUENCE: 264
uuugugaccu gguccacuaa cc                                             22

<210> SEQ ID NO 265
<211> LENGTH: 23
<212> TYPE: RNA
<213> ORGANISM: Artificial Sequence
<220> FEATURE:
<223> OTHER INFORMATION: Synthetic hsa-miR-767-5p-001993

<400> SEQUENCE: 265
ugcaccaugg uugucugagc aug                                            23

<210> SEQ ID NO 266
<211> LENGTH: 22
<212> TYPE: RNA
<213> ORGANISM: Artificial Sequence
<220> FEATURE:
<223> OTHER INFORMATION: Synthetic hsa-miR-769-5p-001998

<400> SEQUENCE: 266
ugagaccucu gguucugag cu                                              22

<210> SEQ ID NO 267
<211> LENGTH: 21
<212> TYPE: RNA
<213> ORGANISM: Artificial Sequence
<220> FEATURE:
<223> OTHER INFORMATION: Synthetic hsa-miR-873-4395467

<400> SEQUENCE: 267
gcaggaacuu gugagucucc u                                              21
```

-continued

```
<210> SEQ ID NO 268
<211> LENGTH: 22
<212> TYPE: RNA
<213> ORGANISM: Artificial Sequence
<220> FEATURE:
<223> OTHER INFORMATION: Synthetic hsa-miR-876-3p-4395336

<400> SEQUENCE: 268
uggugguuua caaaguaauu ca                                                22

<210> SEQ ID NO 269
<211> LENGTH: 22
<212> TYPE: RNA
<213> ORGANISM: Artificial Sequence
<220> FEATURE:
<223> OTHER INFORMATION: Synthetic hsa-miR-885-5p-4395407

<400> SEQUENCE: 269
uccauuacac uacccugccu cu                                                22

<210> SEQ ID NO 270
<211> LENGTH: 21
<212> TYPE: RNA
<213> ORGANISM: Artificial Sequence
<220> FEATURE:
<223> OTHER INFORMATION: Synthetic hsa-miR-886-3p-4395305

<400> SEQUENCE: 270
cgcgggugcu uacugacccu u                                                 21

<210> SEQ ID NO 271
<211> LENGTH: 23
<212> TYPE: RNA
<213> ORGANISM: Artificial Sequence
<220> FEATURE:
<223> OTHER INFORMATION: Synthetic hsa-miR-886-5p-4395304

<400> SEQUENCE: 271
cgggucggag uuagcucaag cgg                                               23

<210> SEQ ID NO 272
<211> LENGTH: 22
<212> TYPE: RNA
<213> ORGANISM: Artificial Sequence
<220> FEATURE:
<223> OTHER INFORMATION: Synthetic hsa-miR-9#-002231

<400> SEQUENCE: 272
auaaagcuag auaaccgaaa gu                                                22

<210> SEQ ID NO 273
<211> LENGTH: 20
<212> TYPE: RNA
<213> ORGANISM: Artificial Sequence
<220> FEATURE:
<223> OTHER INFORMATION: Synthetic hsa-miR-920-002150

<400> SEQUENCE: 273
ggggagcugu ggaagcagua                                                   20

<210> SEQ ID NO 274
<211> LENGTH: 23
<212> TYPE: RNA
<213> ORGANISM: Artificial Sequence
<220> FEATURE:
<223> OTHER INFORMATION: Synthetic hsa-miR-922-002152
```

```
-continued

<400> SEQUENCE: 274
gcagcagaga auaggacuac guc                                           23

<210> SEQ ID NO 275
<211> LENGTH: 23
<212> TYPE: RNA
<213> ORGANISM: Artificial Sequence
<220> FEATURE:
<223> OTHER INFORMATION: Synthetic hsa-miR-92a-1#-002137

<400> SEQUENCE: 275
agguugggau cgguugcaau gcu                                           23

<210> SEQ ID NO 276
<211> LENGTH: 22
<212> TYPE: RNA
<213> ORGANISM: Artificial Sequence
<220> FEATURE:
<223> OTHER INFORMATION: Synthetic hsa-miR-92a-4395169

<400> SEQUENCE: 276
uauugcacuu gucccggccu gu                                            22

<210> SEQ ID NO 277
<211> LENGTH: 23
<212> TYPE: RNA
<213> ORGANISM: Artificial Sequence
<220> FEATURE:
<223> OTHER INFORMATION: Synthetic hsa-miR-9-4373285

<400> SEQUENCE: 277
ucuuugguua ucuagcugua uga                                           23

<210> SEQ ID NO 278
<211> LENGTH: 22
<212> TYPE: RNA
<213> ORGANISM: Artificial Sequence
<220> FEATURE:
<223> OTHER INFORMATION: Synthetic hsa-miR-98-4373009

<400> SEQUENCE: 278
ugagguagua aguuguauug uu                                            22

<210> SEQ ID NO 279
<211> LENGTH: 22
<212> TYPE: RNA
<213> ORGANISM: Artificial Sequence
<220> FEATURE:
<223> OTHER INFORMATION: Synthetic hsa-miR-99a#-002141

<400> SEQUENCE: 279
caagcucgcu ucuauggguc ug                                            22

<210> SEQ ID NO 280
<211> LENGTH: 22
<212> TYPE: RNA
<213> ORGANISM: Artificial Sequence
<220> FEATURE:
<223> OTHER INFORMATION: Synthetic hsa-miR-99b-4373007

<400> SEQUENCE: 280
cacccguaga accgaccuug cg                                            22

<210> SEQ ID NO 281
```

```
<211> LENGTH: 22
<212> TYPE: RNA
<213> ORGANISM: Artificial Sequence
<220> FEATURE:
<223> OTHER INFORMATION: Synthetic mmu-let-7d#-001178

<400> SEQUENCE: 281
cuauacgacc ugcugccuuu cu                                              22

<210> SEQ ID NO 282
<211> LENGTH: 22
<212> TYPE: RNA
<213> ORGANISM: Artificial Sequence
<220> FEATURE:
<223> OTHER INFORMATION: Synthetic rno-miR-29c#-001818

<400> SEQUENCE: 282
ugaccgauuu cuccuggugu uc                                              22

<210> SEQ ID NO 283
<211> LENGTH: 22
<212> TYPE: RNA
<213> ORGANISM: Artificial Sequence
<220> FEATURE:
<223> OTHER INFORMATION: Synthetic rno-miR-7#-001338

<400> SEQUENCE: 283
caacaaauca cagucugcca ua                                              22
```